US008481736B2

(12) United States Patent
Koenemann et al.

(10) Patent No.: US 8,481,736 B2
(45) Date of Patent: Jul. 9, 2013

(54) LIQUID CRYSTALLINE RYLENE TETRACARBOXYLIC ACID DERIVATIVES AND USE THEREOF

(75) Inventors: Martin Koenemann, Mannheim (DE); Neil Gregory Pschirer, Mainz (DE); Klaus Muellen, Cologne (DE); Fabian Nolde, Hannover (DE); Wojciech Pisula, Mainz (DE); Sibylle Mueller, Toronto (CA); Christopher Kohl, Mainz (DE)

(73) Assignees: BASF SE, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 579 days.

(21) Appl. No.: 12/296,312

(22) PCT Filed: Apr. 4, 2007

(86) PCT No.: PCT/EP2007/053330
§ 371 (c)(1),
(2), (4) Date: Nov. 8, 2010

(87) PCT Pub. No.: WO2007/116001
PCT Pub. Date: Oct. 18, 2007

(65) Prior Publication Data
US 2011/0042651 A1    Feb. 24, 2011

(30) Foreign Application Priority Data

Apr. 7, 2006 (EP) ..................................... 06007415

(51) Int. Cl.
C07D 471/08 (2006.01)
H01L 29/00 (2006.01)
H01L 51/00 (2006.01)

(52) U.S. Cl.
USPC ................................ 546/26; 257/40; 313/498

(58) Field of Classification Search
USPC ................................ 546/26; 257/40; 313/498
See application file for complete search history.

(56) References Cited

U.S. PATENT DOCUMENTS

| 4,667,036 | A | | 5/1987 | Iden et al. |
|---|---|---|---|---|
| 5,693,808 | A | | 12/1997 | Langhals |
| 5,986,099 | A | * | 11/1999 | Mullen et al. .................... 546/26 |
| 6,326,494 | B1 | | 12/2001 | Bohm et al. |
| 6,806,368 | B2 | | 10/2004 | Wuerthner et al. |
| 7,358,362 | B2 | | 4/2008 | Koenemann et al. |
| 2003/0181721 | A1 | | 9/2003 | Wuerthner et al. |
| 2005/0017237 | A1 | | 1/2005 | Ong et al. |
| 2005/0176970 | A1 | | 8/2005 | Marks et al. |
| 2005/0222416 | A1 | | 10/2005 | Bohm et al. |
| 2005/0224905 | A1 | | 10/2005 | Forrest et al. |
| 2006/0014128 | A1 | | 1/2006 | Mizuno |
| 2007/0155968 | A1 | | 7/2007 | Konemann et al. |
| 2009/0236591 | A1 | | 9/2009 | Konemann et al. |

FOREIGN PATENT DOCUMENTS

| DE | 3235526 | 3/1984 |
|---|---|---|
| DE | 34 34 059 | 3/1985 |
| DE | 19512773 | 10/1996 |
| DE | 195 47 209 | 6/1997 |
| DE | 10212358 | 10/2003 |
| DE | 102 25 595 | 12/2003 |
| DE | 10233179 | 2/2004 |
| DE | 10233955 | 6/2004 |
| DE | 10 2004 003 735 | 8/2005 |
| DE | 102004024909 | 12/2005 |
| EP | 0 711 812 | 5/1996 |
| JP | 2003 138154 | 5/2003 |
| JP | 2005-45266 | 2/2005 |
| WO | 2005 070895 | 8/2005 |
| WO | 2005 076383 | 8/2005 |
| WO | WO 2005/076815 | 8/2005 |
| WO | 2005 124453 | 12/2005 |
| WO | 2006 093965 | 9/2006 |

OTHER PUBLICATIONS

U.S. Appl. No. 12/673,908, filed Feb. 17, 2010, Koenemann, et al.
Rohr, Ulrike et al., "Liquid crystalline coronene derivatives", J. of Mater. Chem., vol. 11, pp. 1789-1799, XP-002397609, (2001).
Langhals, Heinz et al., "Persistent Fluorescence of Perylene Dyes by Steric Inhibition of Aggregation", Tetrahedron, Pergamon, vol. 56, No. 30, pp. 5435-5441, XP004210209, (2000).
Petritsch, K. et al., "Liquid Crystalline Phthalocyanines in Organic Solar Cells", Synthetic Metals, Elsevier, vol. 102, No. 1/3, pp. 1776-1777, (1999).
Nolde, Fabian et al., "Synthesis and Self-Organization of Core-Extended Perylene Tetracarboxdiimides with Branched Alkyl Substituents", Chem. Mater. vol. 18, pp. 3715-3725, XP-002450049, (2006).
Langhals, H. et al. "Farbstoffe fuer Fluoreszenz-Solarkollektoren", Nachr. Chem. Tech. Lab., vol. 28, No. 10, pp. 716-718, (1980).
Langhals, Heinz et al., "Novel Fluorescent Dyes by the Extension of the Core of Perylenetetracarboxylic Bisimides", Eur J. Org. Chem, pp. 365-380, (2000).
Ahrens, Michael J. et al., "Cyanated Perylene-3,4-dicarboximides and Perylene-3,4:9,10-bis(dicarboximide): Facile Chromophoric Oxidants for Organic Photonics and Electronics", Chem. Mater., vol. 15, No. 14, pp. 2684-2686, (2003).
Jones, Brooks A. et al., "High-Mobility Air-Stable n-Type Semiconductors with Processing Versatility: Dicyanoperylene-3,4:9,10-bis(dicarboximides)", Angew. Chem., vol. 116, pp. 6523-6526, (2004).

(Continued)

Primary Examiner — Charanjit Aulakh
(74) Attorney, Agent, or Firm — Oblon, Spivak, McClelland, Maier & Neustadt, L.L.P.

(57) ABSTRACT

The present invention relates to liquid-crystalline rylene tetracarboxylic acid derivatives, to processes for their preparation and to their use as n-type organic semiconductors for producing organic field-effect transistors and solar cells.

22 Claims, 9 Drawing Sheets

OTHER PUBLICATIONS

Chen, Zhijian et al., "Tetrachloro-substituted Perylene Bisimide Dyes as Promising n-Type Organic Semiconductors: Studies on Structural, Electrochemical and Charge Transport Properties", Chemphyschem, vol. 5, pp. 137-140, (2004).

Debije, Michael G. et al., "Dramatic increase in charge carrier lifetime in a liquid crystalline perylene bisimide derivative upon bay substitution with chlorine", J. Mater. Chem., vol. 15, pp. 1270-1276, (2005).

Shin, Won Suk et al., "Effects of functional groups at perylene diimide derivatives on organic photovoltaic device application", J. Mater. Chem., vol. 16, pp. 384-390, (2006).

U.S. Appl. No. 12/212,199, filed Sep. 17, 2008, Koenemann, et al.
U.S. Appl. No. 12/668,975, filed Jan. 13, 2010, Pschirer, et al.
U.S. Appl. No. 12/738,947, filed Apr. 20, 2010, Koenemann, et al.
P. Miskiewicz, et al.; "Photogeneration and transport in thin films of p- and n-type discotic liquid crystals;" Synthetic Metals, 2003, vol. 137, pp. 905-906.
U.S. Appl. No. 12/666,127, filed Dec. 22, 2009, Koenemann, et al.
A. Rybak, et al., "Charge carrier transport in layers of discotic liquid crystals as studied by transient photocurrents", Synthetic Metals, vol. 156, Jan. 23, 2006, pp. 302-309.

* cited by examiner

Current-voltage characteristic of B) on CuPc

Power-voltage characteristic of B) on CuPc

Current-voltage characteristic of C) on CuPc

Power-voltage characteristic of C) on CuPc

LIQUID CRYSTALLINE RYLENE TETRACARBOXYLIC ACID DERIVATIVES AND USE THEREOF

The present invention relates to liquid-crystalline rylenetetracarboxylic acid derivatives, to processes for their preparation and to their use as n-type organic semiconductors for producing organic field-effect transistors and solar cells.

It is expected that, in the future, not only the conventional inorganic semiconductors but increasingly also organic semiconductors based on low molecular weight or polymeric materials will be used in many sectors of the electronics industry. In many cases, these organic semiconductors have advantages over the conventional inorganic semiconductors, for example better substrate compatibility and better processibility of the semiconductor components based on them. They allow processing on flexible substrates and enable their interface orbital energies to be adjusted precisely to the particular application sector by the methods of molecular modeling. The significantly reduced costs of such components have brought a renaissance to the field of organic electronics. "Organic electronics" is concerned principally with the development of novel materials and manufacturing processes for the production of electronic components based on organic semiconductor layers. These include in particular organic field-effect transistors (OFETs) and organic light-emitting diodes (OLEDs; for example for use in displays) and organic photovoltaics. Great potential for development is also ascribed to organic field-effect transistors, for example in memory elements and integrated optoelectronic devices. There is therefore a great need for organic compounds which are suitable as organic semiconductors, especially n-type semiconductors, and specifically for use in organic field-effect transistors and solar cells.

The direct conversion of solar energy to electrical energy in solar cells is based on the internal photoeffect of a semiconductor material, i.e. the generation of electron-hole pairs by absorption of photons and the separation of the negative and positive charge carriers at a p-n transition or a Schottky contact. The photovoltage thus generated, in an external circuit, can bring about a photocurrent through which the solar cell releases its power.

The semiconductor can absorb only those photons which have an energy which is greater than its band gap. The size of the semiconductor band gap thus determines the proportion of sunlight which can be converted to electrical energy. It is expected that, in the future, organic solar cells will outperform the conventional solar cells based on silicon owing to lower costs, a lighter weight, the possibility of producing flexible and/or colored cells, the greater possibility of fine adjustment of the band gap. There is thus a great need for organic semiconductors which are suitable for producing organic solar cells.

Solar cells normally consist of two absorbent materials with different band gaps, in order to utilize the solar energy with maximum efficiency. The first organic solar cells consisted of a two-layer system composed of a copper phthalocyanine as the p-conductor and PTCBI as the n-conductor, and exhibited an efficiency of 1%. In order to utilize as many incident photons as possible, relatively high layer thicknesses are used (e.g. 100 nm). In order to generate electricity, the excited state generated by the absorbed photons must, however, reach a p-n junction, in order to generate a hole and an electron, which then flow to the anode and cathode. However, most organic semiconductors only have diffusion lengths for the excited state of up to 10 nm. Even by virtue of the best production processes known to date, the distance over which the excited state has to be transmitted can be reduced to at least 10 to 30 nm.

US 2005/0224905 describes organic photovoltaic cells with two organic layers, the thickness of the layers, as a result of production, being no more than 0.8 characteristic transport length.

WO 2005/076383 describes phthalocyanine derivatives, the use thereof as homeotropically oriented layers in electronic components and a process for the production thereof.

DE-A-19512773 describes quaterrylenetetracarboximides which, on the imide nitrogens, have so-called "swallowtail" substituents and the use thereof as fluorescent dyes. Specifically described is the synthesis of N,N'-di(1-hexylheptyl)bis(dicarboximide). Among a multitude of possible fields of use, none of which are demonstrated by working examples, use as dyes for material testing, for example in the production of semiconductor circuits, for analysis of microstructures of integrated semiconductor units and in fluorescence solar collectors, is also described. With regard to the latter use, reference is made to H. Langhals, Nachr. Chem. Tech. Lab. 28 (1980), page 716. According to this, a fluorescence solar collector is an apparatus which is capable of concentrating diffuse light radiation by predominant total reflection in the device. A possible use of the compounds mentioned as n-semiconductors is not disclosed.

DE-A-10212358 describes bichromophoric perylene derivatives in which one imide nitrogen is substituted by an acceptor chromophore, for example a swallowtail radical, and the other amide nitrogen by a donor chromophore, for example an aromatic, and the use thereof. Use as a dye in fluorescence solar collectors, for material testing, for example in the production of semiconductor circuits, and for the analysis of microstructures of integrated semiconductor units, is also mentioned.

DE-A-10233179 describes perylenetetracarboximides in which one of the imide nitrogens bears a swallowtail radical and the other an ethylenically unsaturated radical.

DE-A-102004024909 describes perylenetetracarboximides with relatively highly branched, optionally substituted alkyl substituents on the imide nitrogen atoms. These are said to be suitable, inter alia, as dyes of fluorescent dyes as part of an integrated semiconductor circuit which comprises the dyes as such or in conjunction with other semiconductors, for example in the form of an epitaxy. A specific ability of these compounds to be used as n-semiconductors in organic field-effect transistors and solar cells is not described, let alone demonstrated.

JP-2003138154 describes terrylenetetracarboximides with n-alkyl substituents on the imide nitrogens. However, such compounds are generally not liquid-crystalline.

EP-A-0711812 describes polychromophoric peryleneimides in which at least two perylenetetracarboximide units are bonded to a bridging group via one of their imide nitrogens, and to the use thereof in solar collectors among other applications.

DE-A-10225595 describes 1,6,9,14-tetrasubstituted terrylenetetracarboximides and the use thereof in photovoltaics among other applications. Use as an n-semiconductor for producing solar cells is not described.

DE-A-32 35 526 describes perylene-3,4,9,10-tetracarboximides in which the aromatic ring may be substituted by at least one group selected from alkoxy, alkylthio, aryloxy, arylthio, =SO$_2$ and —SO$_2$—R groups. In addition, the aromatic ring may be substituted by chlorine or bromine. Use as an n-semiconductor in organic field-effect transistors and solar cells is not described.

DE-A-34 34 059 describes chlorinated perylenetetracarboximides where the aromatic ring bears 2, 3, 5 or 6 chlorine atoms. The substituents on the imide nitrogens are selected from a) straight-chain or branched $C_1$-$C_{18}$-alkyl which is unsubstituted or substituted by cyano, hydroxyl, cycloalkyl, alkylcarbonyloxy, alkenylcarbonyloxy or cycloalkylcarbonyloxy, and where the alkyl chain may be interrupted by O or S, or b) $C_5$-$C_{18}$-cycloalkyl which is unsubstituted or substituted by alkyl, carboalkoxy or trifluoromethyl. Use as an n-semiconductor in organic field-effect transistors and solar cells is not described.

DE-A-195 47 209 describes 1,7-disubstituted perylene-3, 4,9,10-tetracarboxylic dianhydrides and perylene-3,4,9,10-tetracarboximides in which the aromatic ring is substituted by at least one group selected from unsubstituted or substituted aryloxy, arylthio, hetaryloxy or hetarylthio. Use as an n-semiconductor in organic field-effect transistors and solar cells is not described.

H. Langhals and S. Kirner describe, in Eur. J. Org. Chem. 2000, 365-380, fluorescent dyes based on perylenetetracarboximides with extensive substitution on the ring. Use as n-semiconductors in organic field-effect transistors and solar cells is not described.

M. J. Ahrens, M. J. Fuller and M. R. Wasielewski describe, in Chem. Mater. 2003, 15, pages 2684-2686, cyanated perylene-3,4-dicarboximides and perylen-3,4,9,10-bis(dicarboximides) as chromophoric oxidizing agents for "Organic photonics and electronics". Specific compounds which have branched groups on both imide nitrogens and which are liquid-crystalline are not described.

B. A. Jones et al. describe, in Angew. Chem. 2004, 116, pages 6523-6526, dicyanoperylene-3,4,9,10-bis(dicarboximides) as air-stable n-semiconductors. The radicals on the imide nitrogens are cyclohexyl and n-$CH_2C_3F_7$.

US 2005/0176970 A1 describes the use of perylene-3,4-dicarboximides and perylene-3,4,9,10-bis(dicarboxy)imides with one or more electron-withdrawing groups as n-semiconductors. Specific compounds which have branched groups on both imide nitrogens and which are liquid-crystalline are not described.

U.S. Pat. No. 6,806,368 describes perylenetetracarboximides with radicals which impart liquid-crystalline properties to the compounds. Their use in electronic components, in transistors, is mentioned, but the explicit use as n-semiconductors for producing organic field-effect transistors and solar cells is not described.

ChemPhysChem 2004, 5, 137-140 describes studies of the structural, electrochemical and charge transport properties of compounds of the formula

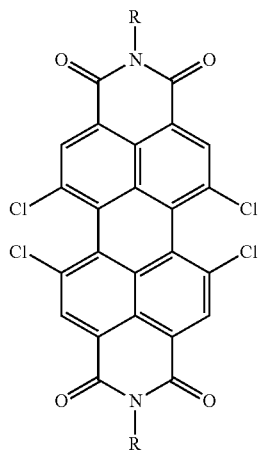

where R=n-$C_{12}H_{25}$, 4-(n-$C_{12}H_{25}$)$C_6H_4$, 2,6-(i-$C_3H_7$)$_2C_6H_3$. Organic field-effect transistors and solar cells are not described.

J. Mater. Chem., 2005, 15, 1270-1276, isotropic mobilities of liquid-crystalline rylenecarboximides of the formula

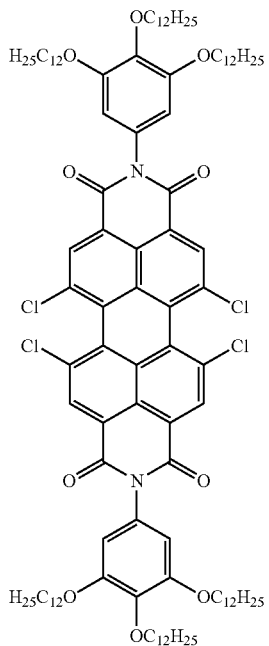

Organic field-effect transistors and solar cells are not described.

US 2003/0181721 A1 describes tetrasubstituted perylenetetracarboximides of the formula

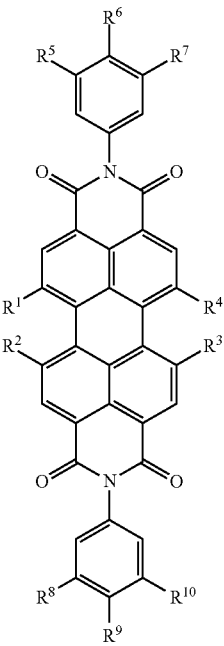

in which $R^1$, $R^2$, $R^3$ and $R^4$ are each independently hydrogen, chlorine, bromine, substituted or unsubstituted aryloxy, arylthio, arylamino, hetaryloxy or hetarylthio, $R^5$, $R^6$, $R^7$, $R^8$, $R^9$ and $R^{19}$ are each independently hydrogen or long-chain alkyl, alkoxy or alkylthio, with the proviso that at least four of these radicals are not hydrogen.

Organic field-effect transistors and solar cells are not described.

WO 2005/124453 describes the use of substituted perylenetetracarboximides as semiconductor material. The amide nitrogen atoms may be substituted by a large number of different groups. One specific embodiment is that of a perylentetracarboximide with unsubstituted aromatic base skeleton, where the amide nitrogens are substituted by (3,4,5-tridodecyloxy)benzyl groups. Further specific embodiments are perylenetetracarboximides with substituents bonded via acetylene groups in the 1 and 7 position of the aromatic base skeleton, the amide nitrogens being substituted by (2,5-diisopropyl)phenyl groups.

The subsequently published WO 2006/093965 describes coronenediimides as semiconductor material.

DE 102 33 955 A1 describes a process for preparing quaterrylenetetracarboximides substituted on the amide nitrogens. The only specific substituent disclosed is (1-hexyl) heptyl. They serve for use as dyes or fluorescent dyes. Although use as part of an integrated semiconductor circuit is disclosed in quite general terms, it remains entirely unclear what purpose the compounds are supposed to serve.

K. Petritsch et al. describe, in Synthetic Metals 102 (1999), 1776-1777, the use of perylenes of the formula

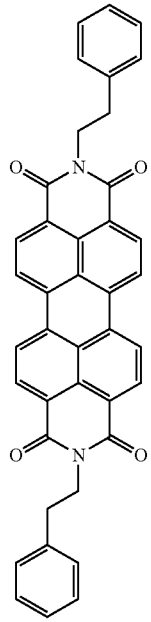 [SMILES: O=C1c2ccc3c4ccc5c6c(ccc(c7ccc(c2c37)C(=O)N1CCc1ccccc1)c64)C(=O)N(CCc1ccccc1)C5=O]

in organic solar cells. A disadvantage of these compounds is their complete insolubility in organic solvents, such that they can be processed only by conversion to the gas phase.

US 2005/0017237 describes the use of compounds of the formula

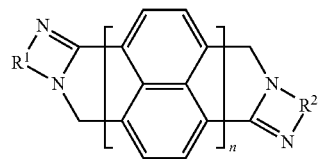

where $R^1$ and $R^2$, together with the nitrogen atoms to which they are bonded, form a carbo- or heterocycle, as semiconductors.

DE 10 2004 003 735 A1 describes a process for preparing compounds of the formula

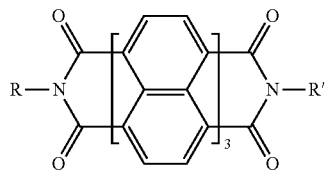

in which R and R' are each independently hydrogen or optionally substituted $C_1$-$C_{30}$-alkyl, $C_5$-$C_8$-cycloalkyl, aryl or hetaryl, by a Suzuki coupling reaction. Specifically disclosed is the synthesis of N-(2,6-diisopropylphenyl)-N'-cyclohexylterrylene-3,4:11,12-tetracarboximide.

WO 2005/070895 describes a process for preparing compounds of the formula

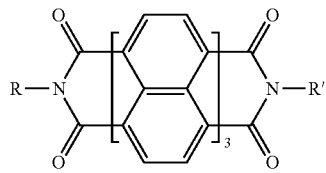

by base-catalyzed one-stage coupling. Specifically disclosed is the synthesis of N-(2,6-diisopropylphenyl)-N'-cyclohexylterrylene-3,4:11,12-tetracarboximide.

Organic Electronics 5 (2004), 237-249 compares the electrical properties of thin films of 1,6,7,12-tetrachloro-N,N'-dimethylperylene-3,4,9,10-biscarboximide with the unchlorinated compound.

W. S. Shin et al. describe, in J. Mater. Chem. 2006, 16, 384-390, effects of the functionalization of perylenediimides on their use in organic photovoltaics. Among other compounds, N,N'-di((1-nonyl)decyl)perylene-3,4:9,10-tetracarboximide is used.

Th. B. Singh et al. describe, in an article which was yet to be published at the priority date of the present application, in Organic Electronics 7 (2006), 480-489, the use of perylenetetracarboximides with branched alkyl radicals on the imide nitrogens as n-semiconductors for organic field-effect transistors.

K. Müllen et al. describe, in an article which was yet to be published at the priority date of the present application, in Chem. Mater. 2006, 18, 3715-3725, the use of rylenetetracarboximides and coronenetetracarboximides with branched alkyl radicals on the imide nitrogens as n-semiconductors for organic field-effect transistors and in photovoltaic cells.

It is an object of the present invention to provide compounds which are suitable as n-semiconductors, for example for use in organic field-effect transistors and solar cells. These should preferably be processible in the form of a solution, such that complicated processes for conversion to the gas phase are dispensed with.

None of the documents cited makes any statements regarding the arrangement of the compounds on the substrates. However, for suitability in OFETs and in solar cells, the correct arrangement of the molecules is important. It has now been found that, surprisingly, the inventive compounds can self-organize both in the "face-on" arrangement favorable for solar cells and in the "edge-on" arrangement favorable for OFETs. The type of arrangement can, if appropriate, be influenced by how the substrate surfaces are pretreated. It thus becomes clear for the first time that the (generally liquid-crystalline) compounds can indeed actually be used for OFETs and in photovoltaics.

This object is achieved by the use of compounds of the general formulae I and II

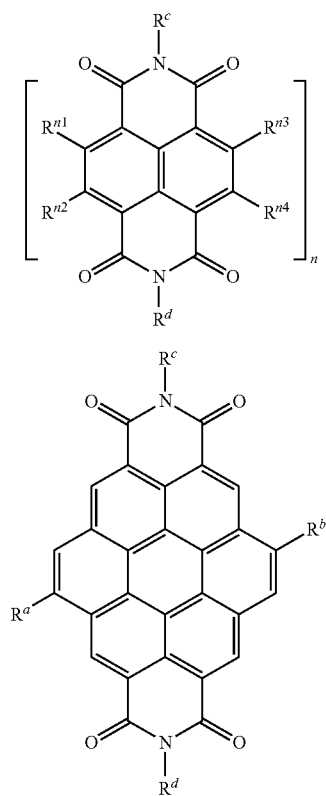

where n is 1, 2, 3 or 4, the $R^{n1}$, $R^{n2}$, $R^{n3}$ and $R^{n4}$ radicals when n=1 or 2 are each independently selected from hydrogen, F, Cl, Br and CN, and when n=3 or 4 are each independently selected from hydrogen, F, Cl and Br, the $R^a$ and $R^b$ radicals are each independently selected from hydrogen and alkyl, the $R^c$ and $R^d$ radicals are each independently selected from groups of the formulae II.1 to II.5:

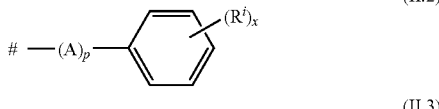

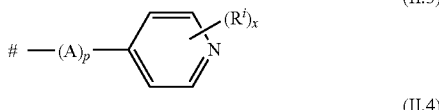

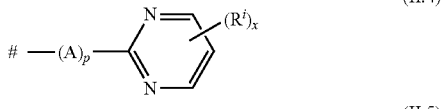

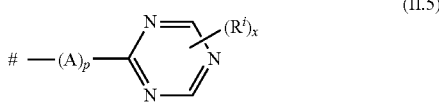

in which

\# represents the bonding site to the imide nitrogen atom, p is 0 or 1, x is 2 or 3, A where present, is a $C_1$-$C_{10}$-alkylene group which may be interrupted by one or more nonadjacent groups which are selected from —O— and —S—, where, in the case that x in the compounds of the formula II.1 is 2, the carbon atom which bears the $R^i$ radicals additionally bears a hydrogen atom, where x in the compounds of the formula II.5 is 2, the $R^i$ radicals are each independently selected from $C_4$-$C_{30}$-alkyl which may be interrupted by one or more nonadjacent oxygen atom(s), where at least one of the $R^i$ radicals in the compounds of the formula II.1 may also be $C_4$-$C_{30}$-alkyloxy or $C_4$-$C_{30}$-alkylthio, as n-semiconductors for organic field-effect transistors or solar cells, excluding the use of compounds of the formula (I) in which n is 2, the $R^{n1}$, $R^{n2}$, $R^{n3}$ and $R^{n4}$ radicals are all hydrogen and the $R^c$ and $R^d$ radicals are each $(C_9H_{19})_2CH$— (i.e. that of N,N'-di((1-nonyl)decyl)perylene-3,4:9,10-tetracarboximide).

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

Figure 1:
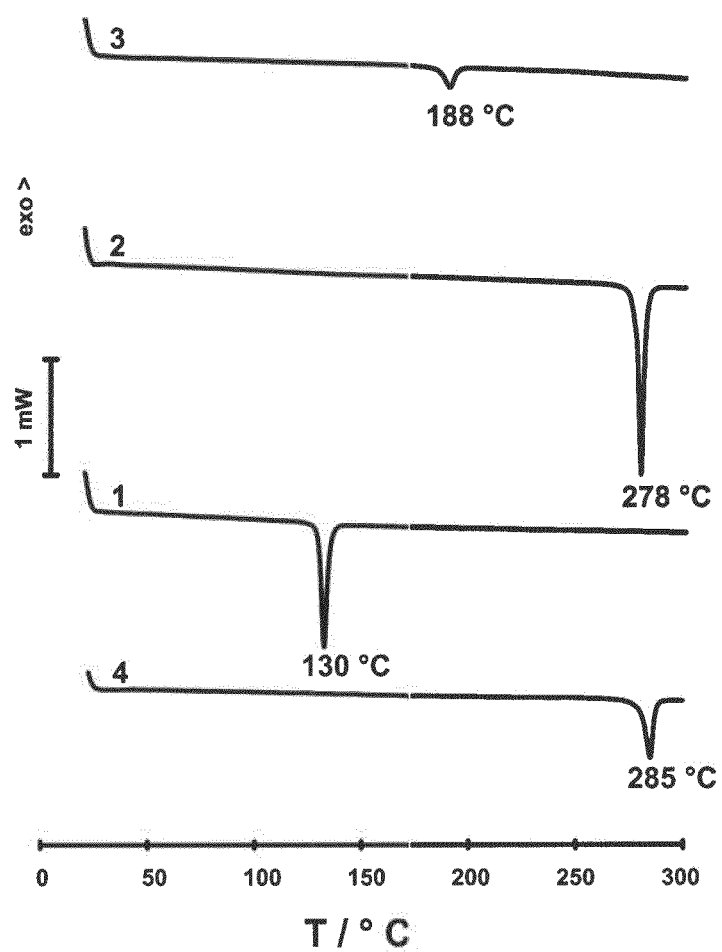
FIG. 1 shows the thermal behavior of compounds 1 to 4, determined by means of DSC (differential scanning calorimetry).

The compounds used in accordance with the invention are generally liquid-crystalline. Owing to the associated ability to form ordered phases (liquid-crystalline phases, also known as mesophases) which are between liquid and solid, and hence to the ability in principle to self-organize, they are particularly suitable for the intended use. The inventive compounds have, for example, a discotic structure which can have a nematic or columnar arrangement. They are generally notable for a high thermal stability and high phase transition temperatures for the conversion from the ordered to the isotropic state, the phase transition temperature rising with increasing size of the aromatic ring. They are thus also suitable, for example, for use in electronic components, such as displays, which are operated under climatically unfavorable conditions, for example in the case of outdoor use. Depending on their type (rylene or coronene) and, if appropriate, their substitution pattern, the compounds used in accordance with the invention can adopt a so-called "edge-on" arrangement, which is particularly advantageous in field-effect transistors, or a so-called "face-on" arrangement, which is particularly advantageous in the case of use in photovoltaics.

Owing to their high degree of order and the generally associated relatively high characteristic transport widths for excited states and relatively high charge mobilities, the organic semiconductor materials used in accordance with the invention are particularly advantageously suitable for use in solar cells. They are suitable especially for producing self-organizing biphasic and polyphasic photovoltaic cells with very good performance properties. With solar cells based on these semiconductors, it is generally possible to achieve very good quantum yields.

In the compounds of the formula I, n denotes the number of naphthalene units which are bonded in the peri position and form the base skeleton of the inventive rylene compounds. In the individual $R^{n1}$ to $R^{n4}$ radicals, n denotes the particular naphthalene group of the rylene skeleton to which the radicals are bonded. $R^{n1}$ to $R^{n4}$ radicals which are bonded to different naphthalene groups may each have identical or different definitions. Accordingly, the compounds of the general formula I may be naphthalene diimides, perylenediimides, terrylenediimides or quaterrylenediimides of the following formula:

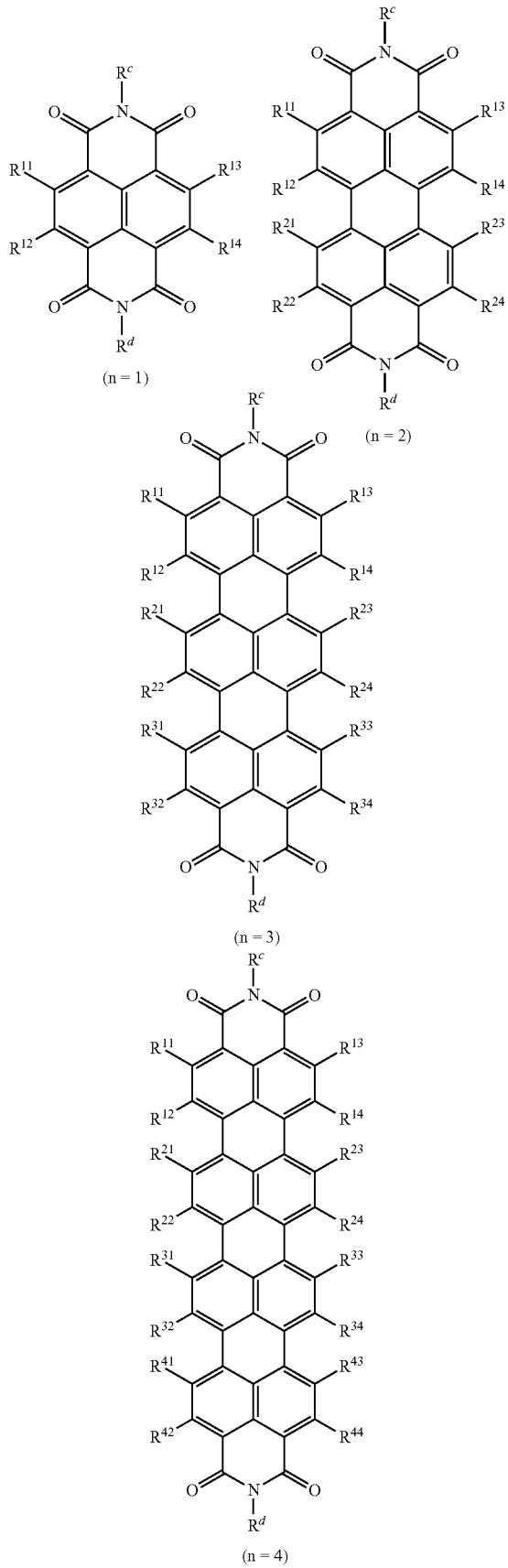

The inventive rylenes are compounds in which two or more alkyl chains proceed from two branching sites bonded directly or indirectly to the imide nitrogens. One embodiment is the use of compounds of the formula I where the $R^{n1}$, $R^{n2}$, $R^{n3}$ and $R^{n4}$ radicals are all hydrogen. A further embodiment is the use of compounds of the formula I where at least one of the $R^{n1}$, $R^{n2}$, $R^{n3}$ and $R^{n4}$ radicals is a radical other than hydrogen.

A preferred embodiment is the use of compounds of the formula I where n is 1, 3 or 4, especially 3 or 4.

In a compound of the formula I or II, the $R^c$ and $R^d$ groups may have identical or different definitions. The $R^c$ and $R^d$ groups in a compound of the formula I or II preferably have the same definition.

One embodiment of the invention is the use of compounds of the formula (I) where the groups the $R^c$ and $R^d$ groups are each groups of the formula (II.1) (so-called swallowtail radicals). In the groups of the formula (II.1), the $R^i$ radicals are preferably selected from $C_4$-$C_8$-alkyl, preferably $C_5$-$C_7$-alkyl. In that case, the $R^c$ and $R^d$ groups are preferably both a group of the formula

(II.1)

in which
represents the bonding site to the imide nitrogen atom, and the $R^i$ radicals are selected from $C_4$-$C_8$-alkyl, preferably $C_5$-$C_7$-alkyl. In that case, the $R^i$ radicals are especially linear alkyl radicals which are not interrupted by oxygen atoms.

A further embodiment of the invention is the use of compounds of the formula (I) where the $R^c$ and $R^d$ groups are each independently selected from groups of the formulae II.2 to II.5. A preferred embodiment is the use of compounds of the formula (I) where the $R^c$ and $R^d$ groups are each independently selected from groups of the formula II.2 and x in the groups of the formula II.2 is 3.

The different $R^i$ radicals may each have identical or different definitions. Preferably, all $R^i$ radicals in a compound of the formula I or II have the same definition.

The $R^i$ radicals are each independently selected from linear or branched $C_4$-$C_{30}$-alkyl which may be interrupted by one or more nonadjacent oxygen atom(s). Preference is given to linear alkyl radicals. Preference is further given to $C_4$-$C_{18}$-alkyl, especially $C_5$-$C_{12}$-alkyl.

In the compounds of the formulae II.2 to II.5, the $R^i$ radicals are not $C_4$-$C_{30}$-alkyloxy or $C_4$-$C_{30}$-alkylthio (i.e. the $R^i$ radicals are bonded to the aromatic or heteroaromatic ring via a carbon atom).

In the compounds of the formula II.1, one of the $R^i$ radicals may also be $C_4$-$C_{30}$-alkyloxy or $C_4$-$C_{30}$-alkylthio. However, in the compounds of the formula II.1, the $R^i$ radicals are preferably each $C_4$-$C_{30}$-alkyl which is not interrupted by oxygen atom(s) either.

In a preferred embodiment, the aforementioned $R^c$ and $R^d$ groups do not comprise an alkylene group A. In a further preferred embodiment, the aforementioned $R^c$ and $R^d$ groups comprise a $C_1$-$C_4$-alkylene group A which may be interrupted by 1, 2 or 3 nonadjacent groups selected from —O— and —S—.

In the context of the present invention, the expression "alkyl" comprises straight-chain or branched alkyl. It is preferably straight-chain or branched $C_1$-$C_{30}$-alkyl, especially $C_1$-$C_{20}$-alkyl and most preferably $C_1$-$C_{12}$-alkyl. Examples of alkyl groups are especially methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression "alkyl" also comprises alkyl radicals whose carbon chains may be interrupted by one or more nonadjacent groups which are selected from —O—, —S—, —$NR^e$—, —CO— and/or —$SO_2$—. $R^e$ is preferably hydrogen, alkyl, cycloalkyl, heterocycloalkyl, aryl or hetaryl. The expression "alkyl" also comprises substituted alkyl radicals.

The above remarks for alkyl also apply to the alkyl moieties in alkoxy, alkylamino, alkylthio, etc.

Alkylene is a linear saturated hydrocarbon chain having from 1 to 10 and especially from 1 to 4 carbon atoms, such as ethane-1,2-diyl, propane-1,3-diyl, butane-1,4-diyl, pentane-1,5-diyl or hexane-1,6-diyl.

Halogen is fluorine, chlorine, bromine or iodine.

Specific examples of suitable $R^c$ and $R^d$ groups include:
Radicals of the formula A

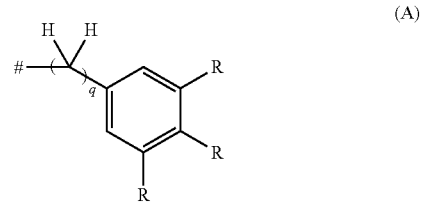

(A)

in which # is the bonding site to the imide nitrogen atom of the rylenetetracarboximide, q is an integer of 0, 1, 2, 3 or 4, and R is $C_4$-$C_{30}$-alkyl.

Radicals of the formula A comprise those in which q is 0, for example
3,4,5-tri(n-butyl)phenyl, 3,4,5-tri(n-pentyl)phenyl, 3,4,5-tri(n-hexyl)phenyl, 3,4,5-tri(n-heptyl)phenyl, 3,4,5-tri(n-octyl)phenyl, 3,4,5-tri(n-nonyl)phenyl, 3,4,5-tri(n-decyl) phenyl, 3,4,5-tri(n-undecyl)phenyl, 3,4,5-tri (n-dodecyl) phenyl, 3,4,5-tri(n-tridecyl)phenyl, 3,4,5-tri(n-tetradecyl) phenyl, 3,4,5-tri(n-pentadecyl)phenyl, 3,4,5-tri(n-hexadecyl)phenyl, 3,4,5-tri(n-heptadecyl)phenyl, 3,4,5-tri (n-octadecyl)phenyl, 3,4,5-tri(nonadecyl)phenyl, 3,4,5-tri (eicosyl)phenyl, 3,4,5-tri(docosanyl)phenyl, 3,4,5-tri (tricosanyl)phenyl, 3,4,5-tri(tetracosanyl)phenyl, 3,4,5-tri (octacosanyl)phenyl;
in which q is 1, for example 3,4,5-tri(n-butyl)benzyl, 3,4,5-tri(n-pentyl)benzyl, 3,4,5-tri(n-hexyl)benzyl, 3,4,5-tri(n-heptyl)benzyl, 3,4,5-tri(n-octyl)benzyl, 3,4,5-tri (n-nonyl)benzyl, 3,4,5-tri(n-decyl)benzyl, 3,4,5-tri(n-undecyl)benzyl, 3,4,5-tri (n-dodecyl)benzyl, 3,4,5-tri(n-tridecyl)benzyl, 3,4,5-tri(n-tetradecyl)benzyl, 3,4,5-tri(n-pentadecyl)benzyl, 3,4,5-tri(n-hexadecyl)benzyl, 3,4,5-tri (n-heptadecyl)benzyl, 3,4,5-tri(n-octadecyl)benzyl, 3,4,5-tri(nonadecyl)benzyl, 3,4,5-tri(eicosyl)benzyl, 3,4,5-tri (docosanyl)benzyl, 3,4,5-tri(tricosanyl)benzyl, 3,4,5-tri (tetracosanyl)benzyl, 3,4,5-tri(octacosanyl)benzyl;
in which q is 2, for example
3,4,5-tri(n-butyl)phenethyl, 3,4,5-tri(n-pentyl)phenethyl, 3,4,5-tri(n-hexyl)phenethyl, 3,4,5-tri(n-heptyl)phenethyl, 3,4,5-tri(n-octyl)phenethyl, 3,4,5-tri(n-nonyl)phenethyl, 3,4,5-tri(n-decyl)phenethyl, 3,4,5-tri(n-undecyl)phenethyl, 3,4,5-tri(n-dodecyl)phenethyl, 3,4,5-tri(n-tridecyl) phenethyl, 3,4,5-tri(n-tetradecyl)phenethyl, 3,4,5-tri(n-pentadecyl)phenethyl, 3,4,5-tri(n-hexadecyl)phenethyl, 3,4,5-tri(n-heptadecyl)phenethyl, 3,4,5-tri(n-octadecyl)phenethyl, 3,4,5-tri(nonadecyl)phenethyl, 3,4,5-tri(eicosyl)phenethyl, 3,4,5-tri(docosanyl)phenethyl, 3,4,5-tri(tricosanyl)phenethyl, 3,4,5-tri(tetracosanyl)phenethyl, 3,4,5-tri(octacosanyl)phenethyl;

in which q is 3, for example
3-(3,4,5-tri(n-butyl)phenyl)propyl, 3-(3,4,5-tri(n-pentyl)phenyl)propyl, 3-(3,4,5-tri(n-hexyl)phenyl)propyl, 3-(3,4,5-tri(n-heptyl)phenyl)propyl, 3-(3,4,5-tri(n-octyl)phenyl)propyl, 3-(3,4,5-tri(n-nonyl)phenyl)propyl, 3-(3,4,5-tri(n-decyl)phenyl)propyl, 3-(3,4,5-tri(n-undecyl)phenyl)propyl, 3-(3,4,5-tri(n-dodecyl)phenyl)propyl, 3-(3,4,5-tri(n-tridecyl)phenyl)propyl, 3-(3,4,5-tri(n-tetradecyl)phenyl)propyl, 3-(3,4,5-tri(n-pentadecyl)phenyl)propyl, 3-(3,4,5-tri(n-hexadecyl)phenyl)propyl, 3-(3,4,5-tri(n-heptadecyl)phenyl)propyl, 3-(3,4,5-tri(n-octadecyl)phenyl)propyl, 3-(3,4,5-tri(nonadecyl)phenyl)propyl, 3-(3,4,5-tri(eicosyl)phenyl)propyl, 3-(3,4,5-tri(docosanyl)phenyl)propyl, 3-(3,4,5-tri(tricosanyl)phenyl)propyl, 3-(3,4,5-tri(tetracosanyl)phenyl)propyl, 3-(3,4,5-tri(octacosanyl)phenyl)propyl;

in which q is 4, for example
4-(3,4,5-tri(n-butyl)phenyl)butyl, 4-(3,4,5-tri(n-pentyl)phenyl)butyl, 4-(3,4,5-tri(n-hexyl)phenyl)butyl, 4-(3,4,5-tri(n-heptyl)phenyl)butyl, 4-(3,4,5-tri(n-octyl)phenyl)butyl, 4-(3,4,5-tri(n-nonyl)phenyl)butyl, 4-(3,4,5-tri(n-decyl)phenyl)butyl, 4-(3,4,5-tri(n-undecyl)phenyl)butyl, 4-(3,4,5-tri(n-dodecyl)phenyl)butyl, 4-(3,4,5-tri(n-tridecyl)phenyl)butyl, 4-(3,4,5-tri(n-tetradecyl)phenyl)butyl, 4-(3,4,5-tri(n-pentadecyl)phenyl)butyl, 4-(3,4,5-tri(n-hexadecyl)phenyl)butyl, 4-(3,4,5-tri(n-heptadecyl)phenyl)butyl, 4-(3,4,5-tri(n-octadecyl)phenyl)butyl, 4-(3,4,5-tri(nonadecyl)phenyl)butyl, 4-(3,4,5-tri(eicosyl)phenyl)butyl, 4-(3,4,5-tri(docosanyl)phenyl)butyl, 4-(3,4,5-tri(tricosanyl)phenyl)butyl, 4-(3,4,5-tri(tetracosanyl)phenyl)butyl, 4-(3,4,5-tri(octacosanyl)phenyl)butyl;

and additionally radicals of the formula B

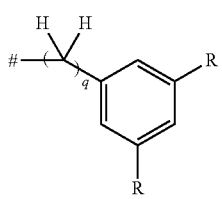

(B)

in which # represents the bonding site to the imide nitrogen atom of the rylenetetracarboximide, q is an integer of 0, 1, 2, 3 or 4, and R is $C_4$-$C_{30}$-alkyl.

Examples of radicals of the formula B comprise those in which q is 0, for example
3,5-di(n-butyl)phenyl, 3,5-di(n-pentyl)phenyl, 3,5-di(n-hexyl)phenyl, 3,4,5-di(n-heptyl)phenyl, 3,5-di(n-octyl)phenyl, 3,5-di(n-nonyl)phenyl, 3,5-di(n-decyl)phenyl, 3,5-di(n-undecyl)phenyl, 3,5-di(n-dodecyl)phenyl, 3,5-di(n-tridecyl)phenyl, 3,5-di(n-tetradecyl)phenyl, 3,5-di(n-pentadecyl)phenyl, 3,5-di(n-hexadecyl)phenyl, 3,5-di(n-heptadecyl)phenyl, 3,5-di(n-octadecyl)phenyl, 3,5-di(nonadecyl)phenyl, 3,5-di(eicosyl)phenyl, 3,5-di(docosanyl)phenyl, 3,5-di(tricosanyl)phenyl, 3,5-di(tetracosanyl)phenyl, 3,5-di(octacosanyl)phenyl;

in which q is 1, for example
3,5-di(n-butyl)benzyl, 3,5-di(n-pentyl)benzyl, 3,5-di(n-hexyl)benzyl, 3,4,5-di(n-heptyl)benzyl, 3,5-di(n-octyl)benzyl, 3,5-di(n-nonyl)benzyl, 3,5-di(n-decyl)benzyl, 3,5-di(n-undecyl)benzyl, 3,5-di(n-dodecyl)benzyl, 3,5-di(n-tridecyl)benzyl, 3,5-di(n-tetradecyl)benzyl, 3,5-di(n-pentadecyl)benzyl, 3,5-di(n-hexadecyl)benzyl, 3,5-di(n-heptadecyl)benzyl, 3,5-di(n-octadecyl)benzyl, 3,5-di(nonadecyl)benzyl, 3,5-di(eicosyl)benzyl, 3,5-di(docosanyl)benzyl, 3,5-di(tricosanyl)benzyl, 3,5-di(tetracosanyl)benzyl, 3,5-di(octacosanyl)benzyl;

in which q is 2, for example
3,5-di(n-butyl)phenethyl, 3,5-di(n-pentyl)phenethyl, 3,5-di(n-hexyl)phenethyl, 3,4,5-di(n-heptyl)phenethyl, 3,5-di(n-octyl)phenethyl, 3,5-di(n-nonyl)phenethyl, 3,5-di(n-decyl)phenethyl, 3,5-di(n-undecyl)phenethyl, 3,5-di(n-dodecyl)phenethyl, 3,5-di(n-tridecyl)phenethyl, 3,5-di(n-tetradecyl)phenethyl, 3,5-di(n-pentadecyl)phenethyl, 3,5-di(n-hexadecyl)phenethyl, 3,5-di(n-heptadecyl)phenethyl, 3,5-di(n-octadecyl)phenethyl, 3,5-di(nonadecyl)phenethyl, 3,5-di(eicosyl)phenethyl, 3,5-di(docosanyl)phenethyl, 3,5-di(tricosanyl)phenethyl, 3,5-di(tetracosanyl)phenethyl, 3,5-di(octacosanyl)phenethyl;

in which q is 3, for example
4-(3,5-di(n-butyl)phenyl)propyl, 4-(3,5-di(n-pentyl)phenyl)propyl, 4-(3,5-di(n-hexyl)phenyl)propyl, 4-(3,5-di(n-heptyl)phenyl)propyl, 4-(3,5-di(n-octyl)phenyl)propyl, 4-(3,5-di(n-nonyl)phenyl)propyl, 4-(3,5-di(n-decyl)phenyl)propyl, 4-(3,5-di(n-undecyl)phenyl)propyl, 4-(3,5-di(n-dodecyl)phenyl)propyl, 4-(3,5-di(n-tridecyl)phenyl)propyl, 4-(3,5-di(n-tetradecyl)phenyl)propyl, 4-(3,5-di(n-pentadecyl)phenyl)propyl, 4-(3,5-di(n-hexadecyl)phenyl)propyl, 4-(3,5-di(n-heptadecyl)phenyl)propyl, 4-(3,5-di(n-octadecyl)phenyl)propyl, 4-(3,5-di(nonadecyl)phenyl)propyl, 4-(3,5-di(eicosyl)phenyl)propyl, 4-(3,5-di(docosanyl)phenyl)propyl, 4-(3,5-di(tricosanyl)phenyl)propyl, 4-(3,5-di(tetracosanyl)phenyl)propyl, 4-(3,5-di(octacosanyl)phenyl)propyl;

in which q is 4, for example
4-(3,5-di(n-butyl)phenyl)butyl, 4-(3,5-di(n-pentyl)phenyl)butyl, 4-(3,5-di(n-hexyl)phenyl)butyl, 4-(3,5-di(n-heptyl)phenyl)butyl, 4-(3,5-di(n-octyl)phenyl)butyl, 4-(3,5-di(n-nonyl)phenyl)butyl, 4-(3,5-di(n-decyl)phenyl)butyl, 4-(3,5-di(n-undecyl)phenyl)butyl, 4-(3,5-di(n-dodecyl)phenyl)butyl, 4-(3,5-di(n-tridecyl)phenyl)butyl, 4-(3,5-di(n-tetradecyl)phenyl)butyl, 4-(3,5-di(n-pentadecyl)phenyl)butyl, 4-(3,5-di(n-hexadecyl)phenyl)butyl, 4-(3,5-di(n-heptadecyl)phenyl)butyl, 4-(3,5-di(n-octadecyl)phenyl)butyl, 4-(3,5-di(nonadecyl)phenyl)butyl, 4-(3,5-di(eicosyl)phenyl)butyl, 4-(3,5-di(docosanyl)phenyl)butyl, 4-(3,5-di(tricosanyl)phenyl)butyl, 4-(3,5-di(tetracosanyl)phenyl)butyl, 4-(3,5-di(octacosanyl)phenyl)butyl;

and additionally radicals of the formula C

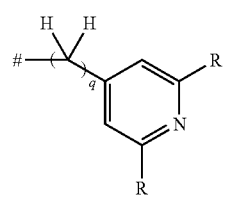

(C)

in which # represents the bonding site to the imide nitrogen atom of the rylenetetracarboximide, q is an integer of 0, 1, 2, 3 or 4, and R is $C_4$-$C_{30}$-alkyl.

Radicals of the formula C comprise those in which q is 0, for example 2,6-di(n-butyl)pyridin-4-yl, 2,6-di(n-pentyl)pyridin-4-yl, 2,6-di(n-hexyl)pyridin-4-yl, 2,6-di(n-heptyl)pyridin-4-yl, 2,6-di(n-octyl)pyridin-4-yl, 2,6-di(n-nonyl)pyridin-4-yl, 2,6-di(n-decyl)pyridin-4-yl, 2,6-di(n-undecyl)pyridin-4-yl, 2,6-di(n-dodecyl)pyridin-4-yl, 2,6-di(n-tridecyl)pyridin-4-yl, 2,6-di(n-tetradecyl)pyridin-4-yl, 2,6-di(n-pentadecyl)pyridin-4-yl, 2,6-di(n-hexadecyl)pyridin-4-yl, 2,6-di(n-heptadecyl)pyridin-4-yl, 2,6-di(n-octadecyl)pyridin-4-yl, 2,6-di(nonadecyl)pyridin-4-yl, 2,6-di(eicosyl)pyridin-4-yl, 2,6-di(docosanyl)pyridin-4-yl, 2,6-di(tricosanyl)pyridin-4-yl, 2,6-di(tetracosanyl)pyridin-4-yl, 2,6-di(octacosanyl)pyridin-4-yl;

in which q is 1, for example
2,6-di(n-butyl)pyridin-4-yl-methyl, 2,6-di(n-pentyl)pyridin-4-yl-methyl, 2,6-di(n-hexyl)pyridin-4-yl-methyl, 2,6-di(n-heptyl)pyridin-4-yl-methyl, 2,6-di(n-octyl)pyridin-4-yl-methyl, 2,6-di(n-nonyl)pyridin-4-yl-methyl, 2,6-di(n-decyl)pyridin-4-yl-methyl, 2,6-di(n-undecyl)pyridin-4-yl-methyl, 2,6-di(n-dodecyl)pyridin-4-yl-methyl, 2,6-di(n-tridecyl)pyridin-4-yl-methyl, 2,6-di(n-tetradecyl)pyridin-4-yl-methyl, 2,6-di(n-pentadecyl)pyridin-4-yl-methyl, 2,6-di(n-hexadecyl)pyridin-4-yl-methyl, 2,6-di(n-heptadecyl)pyridin-4-yl-methyl, 2,6-di(n-octadecyl)pyridin-4-yl-methyl, 2,6-di(nonadecyl)pyridin-4-yl-methyl, 2,6-di(eicosyl)pyridin-4-yl-methyl, 2,6-di(docosanyl)pyridin-4-yl-methyl, 2,6-di(tricosanyl)pyridin-4-yl-methyl, 2,6-di(tetracosanyl)pyridin-4-yl-methyl, 2,6-di(octacosanyl)pyridin-4-yl-methyl;

in which q is 2, for example
2,6-di(n-butyl)pyridin-4-yl-ethyl, 2,6-di(n-pentyl)pyridin-4-yl-ethyl, 2,6-di(n-hexyl)pyridin-4-yl-ethyl, 2,6-di(n-heptyl)pyridin-4-yl-ethyl, 2,6-di(n-octyl)pyridin-4-yl-ethyl, 2,6-di(n-nonyl)pyridin-4-yl-ethyl, 2,6-di(n-decyl)pyridin-4-yl-ethyl, 2,6-di(n-undecyl)pyridin-4-yl-ethyl, 2,6-di(n-dodecyl)pyridin-4-yl-ethyl, 2,6-di(n-tridecyl)pyridin-4-yl-ethyl, 2,6-di(n-tetradecyl)pyridin-4-yl-ethyl, 2,6-di(n-pentadecyl)pyridin-4-yl-ethyl, 2,6-di(n-hexadecyl)pyridin-4-yl-ethyl, 2,6-di(n-heptadecyl)pyridin-4-yl-ethyl, 2,6-di(n-octadecyl)pyridin-4-yl-ethyl, 2,6-di(nonadecyl)pyridin-4-yl-ethyl, 2,6-di(eicosyl)pyridin-4-yl-ethyl, 2,6-di(docosanyl)pyridin-4-yl-ethyl, 2,6-di(tricosanyl)pyridin-4-yl-ethyl, 2,6-di(tetracosanyl)pyridin-4-yl-ethyl, 2,6-di(octacosanyl)pyridin-4-yl-ethyl;

in which q is 3, for example
3-(2,6-di(n-butyl)pyridin-4-yl)-propyl, 3-(2,6-di (n-pentyl)pyridin-4-yl)-propyl, 3-(2,6-di(n-hexyl)pyridin-4-yl)-propyl, 3-(2,6-di (n-heptyl)pyridin-4-yl)-propyl, 3-(2,6-di(n-octyl)pyridin-4-yl)-propyl, 3-(2,6-di(n-nonyl) pyridin-4-yl)-propyl, 3-(2,6-di(n-decyl)pyridin-4-yl)-propyl, 3-(2,6-di (n-undecyl)pyridin-4-yl)-propyl, 3-(2,6-di(n-dodecyl)pyridin-4-yl)-propyl, 3-(2,6-di (n-tridecyl)pyridin-4-yl)-propyl, 3-(2,6-di(n-tetradecyl)pyridin-4-yl)-propyl, 3-(2,6-di (n-pentadecyl)pyridin-4-yl)-propyl, 3-(2,6-di(n-hexadecyl)pyridin-4-yl)-propyl, 3-(2,6-di (n-heptadecyl)pyridin-4-yl)-propyl, 3-(2,6-di(n-octadecyl)pyridin-4-yl)-propyl, 3-(2,6-di(nonadecyl)pyridin-4-yl)-propyl, 3-(2,6-di(eicosyl)pyridin-4-yl)-propyl, 3-(2,6-di(docosanyl)pyridin-4-yl)-propyl, 3-(2,6-di(tricosanyl)pyridin-4-yl)-propyl, 3-(2,6-di(tetracosanyl)pyridin-4-yl)-propyl, 3-(2,6-di(octacosanyl)pyridin-4-yl)-propyl;

in which q is 4, for example
4-(2,6-di(n-butyl)pyridin-4-yl)-butyl, 4-(2,6-di (n-pentyl)pyridin-4-yl)-butyl, 4-(2,6-di(n-hexyl)pyridin-4-yl)-butyl, 4-(2,6-di(n-heptyl) pyridin-4-yl)-butyl, 4-(2,6-di(n-octyl)pyridin-4-yl)-butyl, 4-(2,6-di(n-nonyl)pyridin-4-yl)-butyl, 4-(2,6-di(n-decyl)pyridin-4-yl)-butyl, 4-(2,6-di(n-undecyl) pyridin-4-yl)-butyl, 4-(2,6-di(n-dodecyl)pyridin-4-yl)-butyl, 4-(2,6-di (n-tridecyl)pyridin-4-yl)-butyl, 4-(2,6-di(n-tetradecyl)pyridin-4-yl)-butyl, 4-(2,6-di (n-pentadecyl)pyridin-4-yl)-butyl, 4-(2,6-di(n-hexadecyl)pyridin-4-yl)-butyl, 4-(2,6-di (n-heptadecyl)pyridin-4-yl)-butyl, 4-(2,6-di(n-octadecyl)pyridin-4-yl)-butyl, 4-(2,6-di (nonadecyl)pyridin-4-yl)-butyl, 4-(2,6-di(eicosyl)pyridin-4-yl)-butyl, 4-(2,6-di(docosanyl) pyridin-4-yl)-butyl, 4-(2, 6-di(tricosanyl)pyridin-4-yl)-butyl, 4-(2,6-di (tetracosanyl)pyridin-4-yl)-butyl, 4-(2,6-di(octacosanyl) pyridin-4-yl)-butyl;

and additionally radicals of the formula D

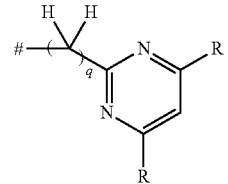

in which # is the bonding site to the imide nitrogen atom of the rylenetetracarboximide, q is an integer of 0, 1, 2, 3 or 4, and R is $C_4$-$C_{30}$-alkyl.

Radicals of the formula D comprise those in which q is 0, for example
4,6-di(n-butyl)pyrimidin-2-yl, 4,6-di(n-pentyl)pyrimidin-2-yl, 4,6-di(n-hexyl)pyrimidin-2-yl, 4,6-di(n-heptyl)pyrimidin-2-yl, 4,6-di(n-octyl)pyrimidin-2-yl, 4,6-di(n-nonyl)pyrimidin-2-yl, 4,6-di(n-decyl)pyrimidin-2-yl, 4,6-di(n-undecyl)pyrimidin-2-yl, 4,6-di(n-dodecyl)pyrimidin-2-yl, 4,6-di(n-tridecyl)pyrimidin-2-yl, 4,6-di(n-tetradecyl)pyrimidin-2-yl, 4,6-di(n-pentadecyl)pyrimidin-2-yl, 4,6-di(n-hexadecyl)pyrimidin-2-yl, 4,6-di(n-heptadecyl)pyrimidin-2-yl, 4,6-di(n-octadecyl)pyrimidin-2-yl, 4,6-di(nonadecyl)pyrimidin-2-yl, 4,6-di(eicosyl)pyrimidin-2-yl, 4,6-di(docosanyl)pyrimidin-2-yl, 4,6-di(tricosanyl)pyrimidin-2-yl, 4,6-di(tetracosanyl)pyrimidin-2-yl, 4,6-di(octacosanyl)pyrimidin-2-yl;

in which q is 1, for example
4,6-di(n-butyl)pyrimidin-2-yl-methyl, 4,6-di(n-pentyl)pyrimidin-2-yl-methyl, 4,6-di(n-hexyl)pyrimidin-2-yl-methyl, 4,6-di(n-heptyl)pyrimidin-2-yl-methyl, 4,6-di(n-octyl)pyrimidin-2-yl-methyl, 4,6-di(n-nonyl)pyrimidin-2-yl-methyl, 4,6-di(n-decyl)pyrimidin-2-yl-methyl, 4,6-di(n-undecyl)pyrimidin-2-yl-methyl, 4,6-di(n-dodecyl)pyrimidin-2-yl-methyl, 4,6-di(n-tridecyl)pyrimidin-2-yl-methyl, 4,6-di(n-tetradecyl)pyrimidin-2-yl-methyl, 4,6-di(n-pentadecyl)pyrimidin-2-yl-methyl, 4,6-di(n-hexadecyl)pyrimidin-2-yl-methyl, 4,6-di(n-heptadecyl)pyrimidin-2-yl-methyl, 4,6-di(n-octadecyl)pyrimidin-2-yl-methyl, 4,6-di(nonadecyl)pyrimidin-2-yl-methyl, 4,6-di(eicosyl)pyrimidin-2-yl-methyl, 4,6-di(docosanyl)pyrimidin-2-yl-methyl, 4,6-di(tricosanyl)pyrimidin-2-yl-methyl, 4,6-di(tetracosanyl)pyrimidin-2-yl-methyl, 4,6-di(octacosanyl)pyrimidin-2-yl-methyl;

in which q is 2, for example
4,6-di(n-butyl)pyrimidin-2-yl-ethyl, 4,6-di(n-pentyl)pyrimidin-2-yl-ethyl, 4,6-di(n-hexyl)pyrimidin-2-yl-ethyl, 4,6-di(n-heptyl)pyrimidin-2-yl-ethyl, 4,6-di(n-octyl)pyrimidin-2-yl-ethyl, 4,6-di(n-nonyl)pyrimidin-2-yl-ethyl, 4,6-di(n-decyl)pyrimidin-2-yl-ethyl, 4,6-di(n-undecyl)pyrimidin-2-yl-ethyl, 4,6-di(n-dodecyl)pyrimidin-2-yl-ethyl, 4,6-di(n-tridecyl)pyrimidin-2-yl-ethyl, 4,6-di(n-tetradecyl)pyrimidin-2-yl-ethyl, 4,6-di(n-pentadecyl)pyrimidin-2-ylethyl, 4,6-di(n-hexadecyl)pyrimidin-2-yl-ethyl, 4,6-di(n-heptadecyl)pyrimidin-2-yl-ethyl, 4,6-di(n-octadecyl)pyrimidin-2-yl-ethyl, 4,6-di(nonadecyl)pyrimidin-2-yl-ethyl, 4,6-di(eicosyl)pyrimidin-2-yl-ethyl, 4,6-di(docosanyl)pyrimidin-2-yl-ethyl, 4,6-di(tricosanyl)pyrimidin-2-yl-ethyl, 4,6-di(tetracosanyl)pyrimidin-2-yl-ethyl, 4,6-di(octacosanyl)pyrimidin-2-yl-ethyl;

in which q is 3, for example 3-(4,6-di(n-butyl)pyrimidin-2-yl)-propyl, 3-(4,6-di(n-pentyl)pyrimidin-2-yl)-propyl, 3-(4,6-di(n-hexyl)pyrimidin-2-yl)-propyl, 3-(4,6-di(n-heptyl)pyrimidin-2-yl)-propyl, 3-(4,6-di(n-octyl)pyrimidin-2-yl)-propyl, 3-(4,6-di(n-nonyl)pyrimidin-2-yl)-propyl, 3-(4,6-di(n-decyl)pyrimidin-2-yl)-propyl, 3-(4,6-di(n-undecyl)pyrimidin-2-yl)-propyl, 3-(4,6-di(n-dodecyl)pyrimidin-2-yl)-propyl, 3-(4,6-di(n-tridecyl)pyrimidin-2-yl)-propyl, 3-(4,6-di(n-tetradecyl)pyrimidin-2-yl)-propyl, 3-(4,6-di(n-pentadecyl)pyrimidin-2-yl)-propyl, 3-(4,6-di(n-hexadecyl)pyrimidin-2-yl)-propyl, 3-(4,6-di(n-heptadecyl)pyrimidin-2-yl)-propyl, 3-(4,6-di(n-octadecyl)pyrimidin-2-yl)-propyl, 3-(4,6-di(nonadecyl)pyrimidin-2-yl)-propyl, 3-(4,6-di(eicosyl)pyrimidin-2-yl)-propyl, 3-(4,6-di(docosanyl)pyrimidin-2-yl)-propyl, 3-(4,6-di(tricosanyl)pyrimidin-2-yl)-propyl, 3-(4,6-di(tetracosanyl)pyrimidin-2-yl)-propyl, 3-(4,6-di(octacosanyl)pyrimidin-2-yl)-propyl;

in which q is 4, for example 4-(4,6-di(n-butyl)pyrimidin-2-yl)-butyl, 4-(4,6-di(n-pentyl)pyrimidin-2-yl)-butyl, 4-(4,6-di(n-hexyl)pyrimidin-2-yl)-butyl, 4-(4,6-di(n-heptyl)pyrimidin-2-yl)-butyl, 4-(4,6-di(n-octyl)pyrimidin-2-yl)-butyl, 4-(4,6-di(n-nonyl)pyrimidin-2-yl)-butyl, 4-(4,6-di(n-decyl)pyrimidin-2-yl)-butyl, 4-(4,6-di(n-undecyl)pyrimidin-2-yl)-butyl, 4-(4,6-di(n-dodecyl)pyrimidin-2-yl)-butyl, 4-(4,6-di(n-tridecyl)pyrimidin-2-yl)-butyl, 4-(4,6-di(n-tetradecyl)pyrimidin-2-yl)-butyl, 4-(4,6-di(n-pentadecyl)pyrimidin-2-yl)-butyl, 4-(4,6-di(n-hexadecyl)pyrimidin-2-yl)-butyl, 4-(4,6-di(n-heptadecyl)pyrimidin-2-yl)-butyl, 4-(4,6-di(n-octadecyl)pyrimidin-2-yl)-butyl, 4-(4,6-di(nonadecyl)pyrimidin-2-yl)-butyl, 4-(4,6-di(eicosyl)pyrimidin-2-yl)-butyl, 4-(4,6-di(docosanyl)pyrimidin-2-yl)-butyl, 4-(4,6-di(tricosanyl)pyrimidin-2-yl)-butyl, 4-(4,6-di(tetracosanyl)pyrimidin-2-yl)-butyl, 4-(4,6-di(octacosanyl)pyrimidin-2-yl)-butyl;

and additionally radicals of the formula E

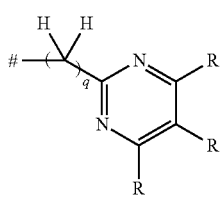

(E)

in which # is the bonding site to the imide nitrogen atom of the rylenetetracarboximide, q is an integer of 0, 1, 2, 3 or 4, and R is $C_4$-$C_{30}$-alkyl.

Radicals of the formula E comprise those in which q is 0, for example 4,5,6-tri(n-butyl)pyrimidin-2-yl, 4,5,6-tri(n-pentyl)pyrimidin-2-yl, 4,5,6-tri(n-hexyl)pyrimidin-2-yl, 4,5,6-tri(n-heptyl)pyrimidin-2-yl, 4,5,6-tri(n-octyl)pyrimidin-2-yl, 4,5,6-tri(n-nonyl)pyrimidin-2-yl, 4,5,6-tri(n-decyl)pyrimidin-2-yl, 4,5,6-tri(n-undecyl)pyrimidin-2-yl, 4,5,6-tri(n-dodecyl)pyrimidin-2-yl, 4,5,6-tri(n-tridecyl)pyrimidin-2-yl, 4,5,6-tri(n-tetradecyl)pyrimidin-2-yl, 4,5,6-tri(n-pentadecyl)pyrimidin-2-yl, 4,5,6-tri(n-hexadecyl)pyrimidin-2-yl, 4,5,6-tri(n-heptadecyl)pyrimidin-2-yl, 4,5,6-tri(n-octadecyl)pyrimidin-2-yl, 4,5,6-tri(nonadecyl)pyrimidin-2-yl, 4,5,6-tri(eicosyl)pyrimidin-2-yl, 4,5,6-tri(docosanyl)pyrimidin-2-yl, 4,5,6-tri(tricosanyl)pyrimidin-2-yl, 4,5,6-tri(tetracosanyl)pyrimidin-2-yl, 4,5,6-tri(octacosanyl)pyrimidin-2-yl;

in which q is 1, for example 4,5,6-tri(n-butyl)pyrimidin-2-yl-methyl, 4,5,6-tri(n-pentyl)pyrimidin-2-yl-methyl, 4,5,6-tri(n-hexyl)pyrimidin-2-yl-methyl, 4,5,6-tri(n-heptyl)pyrimidin-2-yl-methyl, 4,5,6-tri(n-octyl)pyrimidin-2-yl-methyl, 4,5,6-tri(n-nonyl)pyrimidin-2-yl-methyl, 4,5,6-tri(n-decyl)pyrimidin-2-yl-methyl, 4,5,6-tri(n-undecyl)pyrimidin-2-yl-methyl, 4,5,6-tri(n-dodecyl)pyrimidin-2-yl-methyl, 4,5,6-tri(n-tridecyl)pyrimidin-2-yl-methyl, 4,5,6-tri(n-tetradecyl)pyrimidin-2-yl-methyl, 4,5,6-tri(n-pentadecyl)pyrimidin-2-yl-methyl, 4,5,6-tri(n-hexadecyl)pyrimidin-2-yl-methyl, 4,5,6-tri(n-heptadecyl)pyrimidin-2-yl-methyl, 4,5,6-tri(n-octadecyl)pyrimidin-2-yl-methyl, 4,5,6-tri(nonadecyl)pyrimidin-2-yl-methyl, 4,5,6-tri(eicosyl)pyrimidin-2-yl-methyl, 4,5,6-tri(docosanyl)pyrimidin-2-yl-methyl, 4,5,6-tri(tricosanyl)pyrimidin-2-yl-methyl, 4,5,6-tri(tetracosanyl)pyrimidin-2-yl-methyl, 4,5,6-tri(octacosanyl)pyrimidin-2-yl-methyl;

in which q is 2, for example 4,5,6-tri(n-butyl)pyrimidin-2-yl-ethyl, 4,5,6-tri(n-pentyl)pyrimidin-2-yl-ethyl, 4,5,6-tri(n-hexyl)pyrimidin-2-yl-ethyl, 4,5,6-tri(n-heptyl)pyrimidin-2-yl-ethyl, 4,5,6-tri(n-octyl)pyrimidin-2-yl-ethyl, 4,5,6-tri(n-nonyl)pyrimidin-2-yl-ethyl, 4,5,6-tri(n-decyl)pyrimidin-2-yl-ethyl, 4,5,6-tri(n-undecyl)pyrimidin-2-yl-ethyl, 4,5,6-tri(n-dodecyl)pyrimidin-2-yl-ethyl, 4,5,6-tri(n-tridecyl)pyrimidin-2-yl-ethyl, 4,5,6-tri(n-tetradecyl)pyrimidin-2-yl-ethyl, 4,5,6-tri(n-pentadecyl)pyrimidin-2-yl-ethyl, 4,5,6-tri(n-hexadecyl)pyrimidin-2-yl-ethyl, 4,5,6-tri(n-heptadecyl)pyrimidin-2-yl-ethyl, 4,5,6-tri(n-octadecyl)pyrimidin-2-yl-ethyl, 4,5,6-tri(nonadecyl)pyrimidin-2-yl-ethyl, 4,5,6-tri(eicosyl)pyrimidin-2-yl-ethyl, 4,5,6-tri(docosanyl)pyrimidin-2-yl-ethyl, 4,5,6-tri(tricosanyl)pyrimidin-2-yl-ethyl, 4,5,6-tri(tetracosanyl)pyrimidin-2-yl-ethyl, 4,5,6-tri(octacosanyl)pyrimidin-2-yl-ethyl;

in which q is 3, for example 3-(4,5,6-tri(n-butyl)pyrimidin-2-yl)-propyl, 3-(4,5,6-tri(n-pentyl)pyrimidin-2-yl)-propyl, 3-(4,5,6-tri(n-hexyl)pyrimidin-2-yl)-propyl, 3-(4,5,6-tri(n-heptyl)pyrimidin-2-yl)-propyl, 3-(4,5,6-tri(n-octyl)pyrimidin-2-yl)-propyl, 3-(4,5,6-tri(n-nonyl)pyrimidin-2-yl)-propyl, 3-(4,5,6-tri(n-decyl)pyrimidin-2-yl)-propyl, 3-(4,5,6-tri(n-undecyl)pyrimidin-2-yl)-propyl, 3-(4,5,6-tri(n-dodecyl)pyrimidin-2-yl)-propyl, 3-(4,5,6-tri(n-tridecyl)pyrimidin-2-yl)-propyl, 3-(4,5,6-tri(n-tetradecyl)pyrimidin-2-yl)-propyl, 3-(4,5,6-tri(n-pentadecyl)pyrimidin-2-yl)-propyl, 3-(4,5,6-tri(n-hexadecyl)pyrimidin-2-yl)-propyl, 3-(4,5,6-tri(n-heptadecyl)pyrimidin-2-yl)-propyl, 3-(4,5,6-tri(n-octadecyl)pyrimidin-2-yl)-propyl, 3-(4,5,6-tri(nonadecyl)pyrimidin-2-yl)-propyl, 3-(4,5,6-tri(eicosyl)pyrimidin-2-yl)-propyl, 3-(4,5,6-tri(docosanyl)pyrimidin-2-yl)-propyl, 3-(4,5,6-tri(tricosanyl)pyrimidin-2-yl)-propyl, 3-(4,5,6-tri(tetracosanyl)pyrimidin-2-yl)-propyl, 3-(4,5,6-tri(octacosanyl)pyrimidin-2-yl)-propyl;

in which q is 4, for example 4-(4,5,6-tri(n-butyl)pyrimidin-2-yl)-butyl, 4-(4,5,6-tri(n-pentyl)pyrimidin-2-yl)-butyl, 4-(4,5,6-tri(n-hexyl)pyrimidin-2-yl)-butyl, 4-(4,5,6-tri(n-heptyl)pyrimidin-2-yl)-butyl, 4-(4,5,6-tri(n-octyl)pyrimidin-2-yl)-butyl, 4-(4,5,6-tri (n-nonyl)pyrimidin-2-yl)-butyl, 4-(4,5,6-tri(n-decyl) pyrimidin-2-yl)-butyl, 4-(4,5,6-tri(n-undecyl)pyrimidin-2-yl)-butyl, 4-(4,5,6-tri(n-dodecyl)pyrimidin-2-yl)-butyl, 4-(4,5,6-tri(n-tridecyl)pyrimidin-2-yl)-butyl, 4-(4,5,6-tri(n-tetradecyl)pyrimidin-2-yl)-butyl, 4-(4,5,6-tri(n-pentadecyl)pyrimidin-2-yl)-butyl, 4-(4,5,6-tri(n-hexadecyl)pyrimidin-2-yl)-butyl, 4-(4,5,6-tri(n-heptadecyl)pyrimidin-2-yl)-butyl, 4-(4,5,6-tri(n-octadecyl)pyrimidin-2-yl)-butyl, 4-(4,5,6-tri(nonadecyl)pyrimidin-2-yl)-butyl, 4-(4,5,6-tri(eicosyl)pyrimidin-2-yl)-butyl, 4-(4,5,6-tri(docosanyl)pyrimidin-2-yl)-butyl, 4-(4,5,6-tri(tricosanyl)pyrimidin-2-yl)-butyl, 4-(4,5,6-tri(tetracosanyl)pyrimidin-2-yl)-butyl, 4-(4,5,6-tri(octacosanyl)pyrimidin-2-yl)-butyl;

and additionally radicals of the formula F

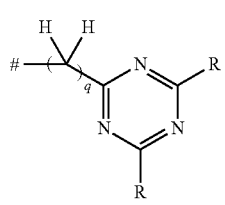

(F)

in which # is the bonding site to the imide nitrogen atom of the rylenetetracarboximide, q is an integer of 0, 1, 2, 3 or 4, and R is $C_4$-$C_{30}$-alkyl.

Radicals of the formula F comprise those in which q is 0, for example 4,6-di(n-butyl)-1,3,5-triazin-2-yl, 4,6-di(n-pentyl)-1,3,5-triazin-2-yl, 4,6-di(n-hexyl)-1,3,5-triazin-2-yl, 4,6-di(n-heptyl)-1,3,5-triazin-2-yl, 4,6-di(n-octyl)-1,3,5-triazin-2-yl, 4,6-di(n-nonyl)-1,3,5-triazin-2-yl, 4,6-di(n-decyl)-1,3,5-triazin-2-yl, 4,6-di(n-undecyl)-1,3,5-triazin-2-yl, 4,6-di(n-dodecyl)-1,3,5-triazin-2-yl, 4,6-di(n-tridecyl)-1,3,5-triazin-2-yl, 4,6-di(n-tetradecyl)-1,3,5-triazin-2-yl, 4,6-di(n-pentadecyl)-1,3,5-triazin-2-yl, 4,6-di(n-hexadecyl)-1,3,5-triazin-2-yl, 4,6-di(n-heptadecyl)-1,3,5-triazin-2-yl, 4,6-di(n-octadecyl)-1,3,5-triazin-2-yl, 4,6-di(nonadecyl)-1,3,5-triazin-2-yl, 4,6-di(eicosyl)-1,3,5-triazin-2-yl, 4,6-di(docosanyl)-1,3,5-triazin-2-yl, 4,6-di(tricosanyl)-1,3,5-triazin-2-yl, 4,6-di(tetracosanyl)-1,3,5-triazin-2-yl, 4,6-di(octacosanyl)-1,3,5-triazin-2-yl;

in which q is 1, for example 4,6-di(n-butyl)-1,3,5-triazin-2-yl-methyl, 4,6-di(n-pentyl)-1,3,5-triazin-2-yl-methyl, 4,6-di(n-hexyl)-1,3,5-triazin-2-yl-methyl, 4,6-di(n-heptyl)-1,3,5-triazin-2-yl-methyl, 4,6-di(n-octyl)-1,3,5-triazin-2-yl-methyl, 4,6-di(n-nonyl)-1,3,5-triazin-2-yl-methyl, 4,6-di(n-decyl)-1,3,5-triazin-2-yl-methyl, 4,6-di(n-undecyl)-1,3,5-triazin-2-yl-methyl, 4,6-di(n-dodecyl)-1,3,5-triazin-2-yl-methyl, 4,6-di(n-tridecyl)-1,3,5-triazin-2-yl-methyl, 4,6-di(n-tetradecyl)-1,3,5-triazin-2-yl-methyl, 4,6-di(n-pentadecyl)-1,3,5-triazin-2-yl-methyl, 4,6-di(n-hexadecyl)-1,3,5-triazin-2-yl-methyl, 4,6-di(n-heptadecyl)-1,3,5-triazin-2-yl-methyl, 4,6-di(n-octadecyl)-1,3,5-triazin-2-yl-methyl, 4,6-di(nonadecyl)-1,3,5-triazin-2-yl-methyl, 4,6-di(eicosyl)-1,3,5-triazin-2-yl-methyl, 4,6-di(docosanyl)-1,3,5-triazin-2-yl-methyl, 4,6-di(tricosanyl)-1,3,5-triazin-2-yl-methyl, 4,6-di(tetracosanyl)-1,3,5-triazin-2-yl-methyl, 4,6-di(octacosanyl)-1,3,5-triazin-2-yl-methyl;

in which q is 2, for example 4,6-di(n-butyl)-1,3,5-triazin-2-yl-ethyl, 4,6-di(n-pentyl)-1,3,5-triazin-2-yl-ethyl, 4,6-di(n-hexyl)-1,3,5-triazin-2-yl-ethyl, 4,6-di(n-heptyl)-1,3,5-triazin-2-yl-ethyl, 4,6-di(n-octyl)-1,3,5-triazin-2-yl-ethyl, 4,6-di(n-nonyl)-1,3,5-triazin-2-yl-ethyl, 4,6-di(n-decyl)-1,3,5-triazin-2-yl-ethyl, 4,6-di(n-undecyl)-1,3,5-triazin-2-yl-ethyl, 4,6-di(n-dodecyl)-1,3,5-triazin-2-yl-ethyl, 4,6-di(n-tridecyl)-1,3,5-triazin-2-yl-ethyl, 4,6-di(n-tetradecyl)-1,3,5-triazin-2-yl-ethyl, 4,6-di(n-pentadecyl)-1,3,5-triazin-2-yl-ethyl, 4,6-di(n-hexadecyl)-1,3,5-triazin-2-yl-ethyl, 4,6-di(n-heptadecyl)-1,3,5-triazin-2-yl-ethyl, 4,6-di(n-octadecyl)-1,3,5-triazin-2-yl-ethyl, 4,6-di(nonadecyl)-1,3,5-triazin-2-yl-ethyl, 4,6-di(eicosyl)-1,3,5-triazin-2-yl-ethyl, 4,6-di(docosanyl)-1,3,5-triazin-2-yl-ethyl, 4,6-di(tricosanyl)-1,3,5-triazin-2-yl-ethyl, 4,6-di(tetracosanyl)-1,3,5-triazin-2-yl-ethyl, 4,6-di(octacosanyl)-1,3,5-triazin-2-yl-ethyl;

in which q is 3, for example 3-(4,6-di(n-butyl)-1,3,5-triazin-2-yl)-propyl, 3-(4,6-di(n-pentyl)-1,3,5-triazin-2-yl)-propyl, 3-(4,6-di(n-hexyl)-1,3,5-triazin-2-yl)-propyl, 3-(4,6-di(n-heptyl)-1,3,5-triazin-2-yl)-propyl, 3-(4,6-di(n-octyl)-1,3,5-triazin-2-yl)-propyl, 3-(4,6-di(n-nonyl)-1,3,5-triazin-2-yl)-propyl, 3-(4,6-di(n-decyl)-1,3,5-triazin-2-yl)-propyl, 3-(4,6-di(n-undecyl)-1,3,5-triazin-2-yl)-propyl, 3-(4,6-di(n-dodecyl)-1,3,5-triazin-2-yl)-propyl, 3-(4,6-di(n-tridecyl)-1,3,5-triazin-2-yl)-propyl, 3-(4,6-di(n-tetradecyl)-1,3,5-triazin-2-yl)-propyl, 3-(4,6-di(n-pentadecyl)-1,3,5-triazin-2-yl)-propyl, 3-(4,6-di(n-hexadecyl)-1,3,5-triazin-2-yl)-propyl, 3-(4,6-di(n-heptadecyl)-1,3,5-triazin-2-yl)-propyl, 3-(4,6-di(n-octadecyl)-1,3,5-triazin-2-yl)-propyl, 3-(4,6-di(nonadecyl)-1,3,5-triazin-2-yl)-propyl, 3-(4,6-di(eicosyl)-1,3,5-triazin-2-yl)-propyl, 3-(4,6-di(docosanyl)-1,3,5-triazin-2-yl)-propyl, 3-(4,6-di(tricosanyl)-1,3,5-triazin-2-yl)-propyl, 3-(4,6-di(tetracosanyl)-1,3,5-triazin-2-yl)-propyl, 3-(4,6-di(octacosanyl)-1,3,5-triazin-2-yl)-propyl;

in which q is 4, for example 4-(4,6-di(n-butyl)-1,3,5-triazin-2-yl)-butyl, 4-(4,6-di(n-pentyl)-1,3,5-triazin-2-yl)-butyl, 4-(4,6-di(n-hexyl)-1,3,5-triazin-2-yl)-butyl, 4-(4,6-di(n-heptyl)-1,3,5-triazin-2-yl)-butyl, 4-(4,6-di(n-octyl)-1,3,5-triazin-2-yl)-butyl, 4-(4,6-di(n-nonyl)-1,3,5-triazin-2-yl)-butyl, 4-(4,6-di(n-decyl)-1,3,5-triazin-2-yl)-butyl, 4-(4,6-di(n-undecyl)-1,3,5-triazin-2-yl)-butyl, 4-(4,6-di(n-dodecyl)-1,3,5-triazin-2-yl)-butyl, 4-(4,6-di(n-tridecyl)-1,3,5-triazin-2-yl)-butyl, 4-(4,6-di(n-tetradecyl)-1,3,5-triazin-2-yl)-butyl, 4-(4,6-di(n-pentadecyl)-1,3,5-triazin-2-yl)-butyl, 4-(4,6-di(n-hexadecyl)-1,3,5-triazin-2-yl)-butyl, 4-(4,6-di(n-heptadecyl)-1,3,5-triazin-2-yl)-butyl, 4-(4,6-di(n-octadecyl)-1,3,5-triazin-2-yl)-butyl, 4-(4,6-di(nonadecyl)-1,3,5-triazin-2-yl)-butyl, 4-(4,6-di(eicosyl)-1,3,5-triazin-2-yl)-butyl, 4-(4,6-di(docosanyl)-1,3,5-triazin-2-yl)-butyl, 4-(4,6-di(tricosanyl)-1,3,5-triazin-2-yl)-butyl, 4-(4,6-di(tetracosanyl)-1,3,5-triazin-2-yl)-butyl, 4-(4,6-di(octacosanyl)-1,3,5-triazin-2-yl)-butyl;

and additionally radicals of the formula G

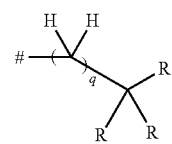

(G)

in which # is the bonding site to the imide nitrogen atom of the rylenetetracarboximide, q is an integer of 0, 1, 2, 3, 4, 5 or 6, and R is $C_4$-$C_{30}$-alkyl.

Examples of suitable radicals of the formula G comprise the formulae G-0.a, G-0.b, G-0.c, G-1.a, G-1.b, G-1.c, G-2.a, G-2.b, G-2.c, G-3.a, G-3.b, G-3.c, G-4.a, G-4.b, G-4.c, G-5.a, G-5.b, G-5.c, G-6.a, G-6.b, G-6.c

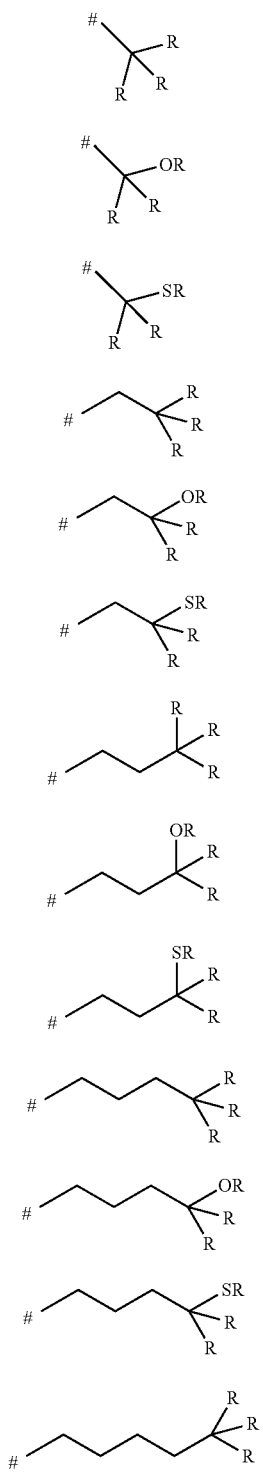

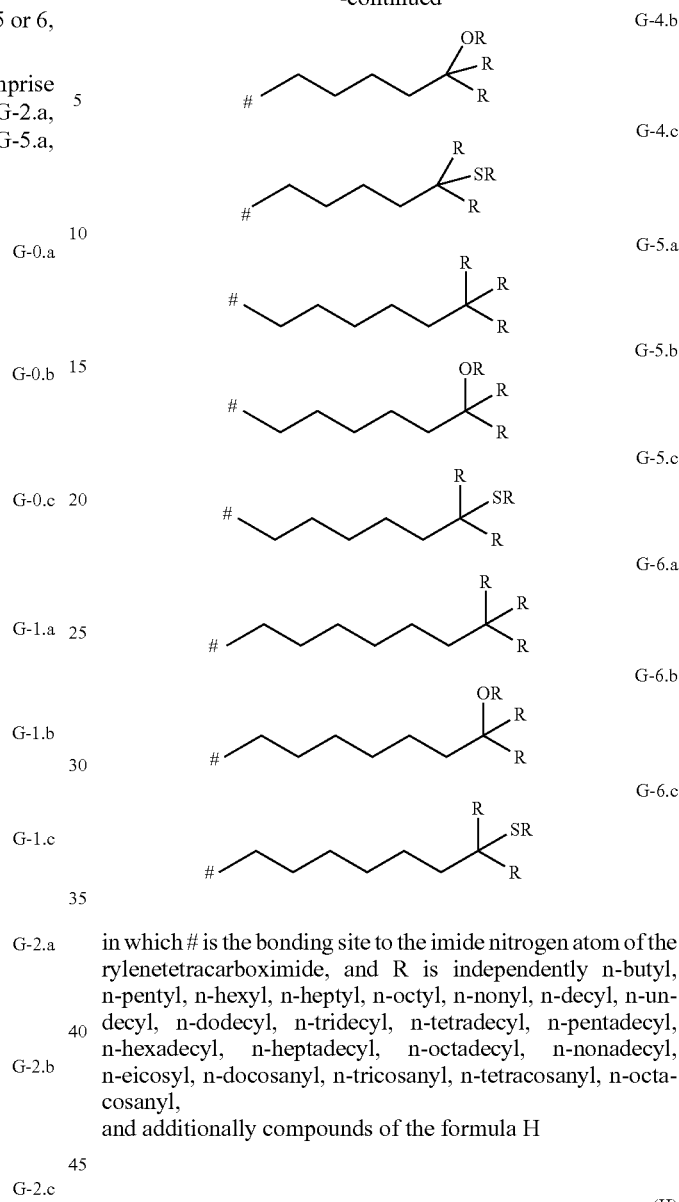

in which # is the bonding site to the imide nitrogen atom of the rylenetetracarboximide, and R is independently n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-docosanyl, n-tricosanyl, n-tetracosanyl, n-octacosanyl, and additionally compounds of the formula H

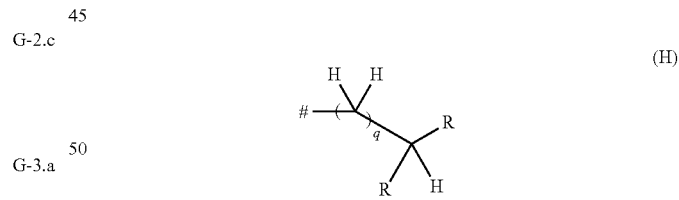

(H)

in which # is the bonding site to the imide nitrogen atom of the rylenetetracarboximide, q is an integer of 0, 1, 2, 3, 4, 5 or 6, and R is $C_4$-$C_{30}$-alkyl, $C_4$-$C_{30}$-alkylthio or $C_4$-$C_{30}$-alkoxy.

Radicals of the formula H comprise those in which q is 0, for example 1-ethylpropyl, 1-methylpropyl, 1-propylbutyl, 1-ethylbutyl, 1-methylbutyl, 1-butylpentyl, 1-propylpentyl, 1-ethylpentyl, 1-methylpentyl, 1-pentylhexyl, 1-butylhexyl, 1-propylhexyl, 1-ethylhexyl, 1-methylhexyl, 1-hexylheptyl, 1-pentylheptyl, 1-butylheptyl, 1-propylheptyl, 1-ethylheptyl, 1-methylheptyl, 1-heptyloctyl, 1-hexyloctyl, 1-pentyloctyl, 1-butyloctyl, 1-propyloctyl, 1-ethyloctyl, 1-methyloctyl, 1-octylnonyl, 1-heptylnonyl, 1-hexylnonyl, 1-pentylnonyl, 1-butylnonyl, 1-propylnonyl, 1-ethylnonyl, 1-methylnonyl, 1-nonyldecyl, 1-octyldecyl, 1-heptyldecyl, 1-hexyldecyl, 1-pentyldecyl, 1-butyldecyl, 1-propyldecyl, 1-ethyldecyl, 1-methyldecyl, 1-decylundecyl, 1-nonylundecyl, 1-octylundecyl, 1-heptylundecyl, 1-hexylundecyl, 1-pentylundecyl, 1-butylundecyl, 1-propylundecyl, 1-ethylundecyl, 1-methylundecyl, 1-undecyldodecyl, 1-decyldodecyl, 1-nonyldodecyl, 1-octyldodecyl, 1-heptyldodecyl, 1-hexyldodecyl, 1-pentyldodecyl, 1-butyldodecyl, 1-propyldodecyl, 1-ethyldodecyl, 1-methyldodecyl, 1-dodecyltridecyl, 1-undecyltridecyl, 1-decyltridecyl, 1-nonyltridecyl, 1-octyltridecyl, 1-heptyltridecyl, 1-hexyltridecyl, 1-pentyltridecyl, 1-butyltridecyl, 1-propyltridecyl, 1-ethyltridecyl, 1-methyltridecyl, 1-tridecyltetradecyl, 1-undecyltetradecyl, 1-decyltetradecyl, 1-nonyltetradecyl, 1-octyltetradecyl, 1-hetyltetradecyl, 1-hexyltetradecyl, 1-pentyltetradecyl, 1-butyltetradecyl, 1-propyltetradecyl, 1-ethyltetradecyl, 1-methyltetradecyl, 1-pentadecylhexadecyl, 1-tetradecylhexadecyl, 1-tridecylhexadecyl, 1-dodecylhexadecyl, 1-undecylhexadecyl, 1-decylhexadecyl, 1-nonylhexadecyl, 1-octylhexadecyl, 1-heptylhexadecyl, 1-hexylhexadecyl, 1-pentylhexadecyl, 1-butylhexadecyl, 1-propylhexadecyl, 1-ethylhexadecyl, 1-methylhexadecyl, 1-hexadecyloctadecyl, 1-pentadecyloctadecyl, 1-tetradecyloctadecyl, 1-tridecyloctadecyl, 1-dodecyloctadecyl, 1-undecyloctadecyl, 1-decyloctadecyl, 1-nonyloctadecyl, 1-octyloctadecyl, 1-heptyloctadecyl, 1-hexyloctadecyl, 1-pentyloctadecyl, 1-butyloctadecyl, 1-propyloctadecyl, 1-ethyloctadecyl, 1-methyloctadecyl, 1-nonadecyleicosanyl, 1-octadecyleicosanyl, 1-heptadecyleicosanyl, 1-hexadecyleicosanyl, 1-pentadecyleicosanyl, 1-tetradecyleicosanyl, 1-tridecyleicosanyl, 1-dodecyleicosanyl, 1-undecyleicosanyl, 1-decyleicosanyl, 1-nonyleicosanyl, 1-octyleicosanyl, 1-heptyleicosanyl, 1-hexyleicosanyl, 1-pentyleicosanyl, 1-butyleicosanyl, 1-propyleicosanyl, 1-ethyleicosanyl, 1-methyleicosanyl, 1-eicosanyldocosanyl, 1-nonadecyldocosanyl, 1-octadecyldocosanyl, 1-heptadecyldocosanyl, 1-hexadecyldocosanyl, 1-pentadecyldocosanyl, 1-tetradecyldocosanyl, 1-tridecyldocosanyl, 1-undecyldocosanyl, 1-decyldocosanyl, 1-nonyldocosanyl, 1-octyldocosanyl, 1-heptyldocosanyl, 1-hexyldocosanyl, 1-pentyldocosanyl, 1-butyldocosanyl, 1-propyldocosanyl, 1-ethyldocosanyl, 1-methyldocosanyl, 1-tricosanyltetracosanyl, 1-docosanyltetracosanyl, 1-nonadecyltetracosanyl, 1-octadecyltetracosanyl, 1-heptadecyltetracosanyl, 1-hexadecyltetracosanyl, 1-pentadecyltetracosanyl, 1-pentadecyltetracosanyl, 1-tetradecyltetracosanyl, 1-tridecyltetracosanyl, 1-dodecyltetracosanyl, 1-undecyltetracosanyl, 1-decyltetracosanyl, 1-nonyltetracosanyl, 1-octyltetracosanyl, 1-heptyltetracosanyl, 1-hexyltetracosanyl, 1-pentyltetracosanyl, 1-butyltetracosanyl, 1-propyltetracosanyl, 1-ethyltetracosanyl, 1-methyltetracosanyl, 1-heptacosanyloctacosanyl, 1-hexacosanyloctacosanyl, 1-pentacosanyloctacosanyl, 1-tetracosanyloctacosanyl, 1-tricosanyloctacosanyl, 1-docosanyloctacosanyl, 1-nonadecyloctacosanyl, 1-octadecyloctacosanyl, 1-heptadecyloctacosanyl, 1-hexadecyloctacosanyl, 1-hexadecyloctacosanyl, 1-pentadecyloctacosanyl, 1-tetradecyloctacosanyl, 1-tridecyloctacosanyl, 1-dodecyloctacosanyl, 1-undecyloctacosanyl, 1-decyloctacosanyl, 1-nonyloctacosanyl, 1-octyloctacosanyl, 1-heptyloctacosanyl, 1-hexyloctacosanyl, 1-pentyloctacosanyl, 1-butyloctacosanyl, 1-propyloctacosanyl, 1-ethyloctacosanyl, 1-methyloctacosanyl;

1-ethyloxypropyl, 1-methyloxypropyl, 1-propylbutyl, 1-ethyloxybutyl, 1-methyloxybutyl, 1-butyloxypentyl, 1-propylpentyl, 1-ethyloxypentyl, 1-methyloxypentyl, 1-pentyloxyhexyl, 1-butyloxyhexyl, 1-propylhexyl, 1-ethyloxyhexyl, 1-methyloxyhexyl, 1-hexyloxyheptyl, 1-pentyloxyheptyl, 1-butyloxyheptyl, 1-propylheptyl, 1-ethyloxyheptyl, 1-methyloxyheptyl, 1-heptyloctyl, 1-hexyloxyoctyl, 1-pentyloxyoctyl, 1-butyloxyoctyl, 1-propyloctyl, 1-ethyloxyoctyl, 1-methyloxyoctyl, 1-octyloxynonyl, 1-heptylnonyl, 1-hexyloxynonyl, 1-pentyloxynonyl, 1-butyloxynonyl, 1-propylnonyl, 1-ethyloxynonyl, 1-methyloxynonyl, 1-nonyloxydecyl, 1-octyloxydecyl, 1-heptyldecyl, 1-hexyloxydecyl, 1-pentyloxydecyl, 1-butyloxydecyl, 1-propyldecyl, 1-ethyloxydecyl, 1-methyloxydecyl, 1-decyloxyundecyl, 1-nonyloxyundecyl, 1-octyloxyundecyl, 1-heptylundecyl, 1-hexyloxyundecyl, 1-pentyloxyundecyl, 1-butyloxyundecyl, 1-propylundecyl, 1-ethyloxyundecyl, 1-methyloxyundecyl, 1-undecyloxydodecyl, 1-decyloxydodecyl, 1-nonyloxydodecyl, 1-octyloxydodecyl, 1-heptyldodecyl, 1-hexyloxydodecyl, 1-pentyloxydodecyl, 1-butyloxydodecyl, 1-propyldodecyl, 1-ethyloxydodecyl, 1-methyloxydodecyl, 1-dodecyloxytridecyl, 1-undecyloxytridecyl, 1-decyloxytridecyl, 1-nonyloxytridecyl, 1-octyloxytridecyl, 1-heptyltridecyl, 1-hexyloxytridecyl, 1-pentyloxytridecyl, 1-butyloxytridecyl, 1-propyltridecyl, 1-ethyloxytridecyl, 1-methyloxytridecyl, 1-tridecyloxytetradecyl, 1-undecyloxytetradecyl, 1-decyloxytetradecyl, 1-nonyloxytetradecyl, 1-octyloxytetradecyl, 1-hetyltetradecyl, 1-hexyloxytetradecyl, 1-pentyltetradecyl, 1-butyloxytetradecyl, 1-propyltetradecyl, 1-ethyloxytetradecyl, 1-methyloxytetradecyl, 1-pentadecyloxyhexadecyl, 1-tetradecyloxyhexadecyl, 1-tridecyloxyhexadecyl, 1-dodecyloxyhexadecyl, 1-undecyloxyhexadecyl, 1-decyloxyhexadecyl, 1-nonyloxyhexadecyl, 1-octyloxyhexadecyl, 1-heptylhexadecyl, 1-hexyloxyhexadecyl, 1-pentyloxyhexadecyl, 1-butyloxyhexadecyl, 1-propylhexadecyl, 1-ethyloxyhexadecyl, 1-methyloxyhexadecyl, 1-hexadecyloxyoctadecyl, 1-pentadecyloxyoctadecyl, 1-tetradecyloxyoctadecyl, 1-tridecyloxyoctadecyl, 1-dodecyloxyoctadecyl, 1-undecyloxyoctadecyl, 1-decyloxyoctadecyl, 1-nonyloxyoctadecyl, 1-octyloxyoctadecyl, 1-heptyloctadecyl, 1-hexyloxyoctadecyl, 1-pentyloxyoctadecyl, 1-butyloxyoctadecyl, 1-propyloctadecyl, 1-ethyloxyoctadecyl, 1-methyloxyoctadecyl, 1-nonadecyloxyeicosanyl, 1-octadecyloxyeicosanyl, 1-heptadecyloxyeicosanyl, 1-hexadecyloxyeicosanyl, 1-pentadecyloxyeicosanyl, 1-tetradecyloxyeicosanyl, 1-tridecyloxyeicosanyl, 1-dodecyloxyeicosanyl, 1-undecyloxyeicosanyl, 1-decyloxyeicosanyl, 1-nonyloxyeicosanyl, 1-octyloxyeicosanyl, 1-heptyleicosanyl, 1-hexyloxyeicosanyl, 1-pentyloxyeicosanyl, 1-butyloxyeicosanyl, 1-propyleicosanyl, 1-ethyloxyeicosanyl, 1-methyleicosanyl, 1-eicosanyloxydocosanyl, 1-nonadecyloxydocosanyl, 1-octadecyloxydocosanyl, 1-heptadecyloxydocosanyl, 1-hexadecyloxydocosanyl, 1-pentadecyloxydocosanyl, 1-tetradecyloxydocosanyl, 1-tridecyloxydocosanyl, 1-undecyloxydocosanyl, 1-decyloxydocosanyl, 1-nonyloxydocosanyl, 1-octyloxydocosanyl, 1-heptyldocosanyl, 1-hexyloxydocosanyl, 1-pentyloxydocosanyl, 1-butyloxydocosanyl, 1-propyldocosanyl, 1-ethyloxydocosanyl, 1-methyloxydocosanyl, 1-tricosanyloxytetracosanyl, 1-docosanyloxytetracosanyl, 1-nonadecyloxytetracosanyl, 1-octadecyloxytetracosanyl, 1-heptadecyloxytetracosanyl, 1-hexadecyloxytetracosanyl, 1-pentadecyloxytetracosanyl, 1-pentadecyloxytetracosanyl, 1-tetradecyloxytetracosanyl, 1-tridecyloxytetracosanyl, 1-dodecyloxytetracosanyl, 1-undecyloxytetracosanyl, 1-decyloxytetracosanyl, 1-nonyloxytetracosanyl, 1-octyloxytetracosanyl, 1-heptyltetracosanyl, 1-hexyloxytetracosanyl, 1-pentyloxytetracosanyl, 1-butyloxytetracosanyl, 1-propyltetracosanyl, 1-ethyloxytetracosanyl, 1-methyloxytetracosanyl, 1-heptacosanyloxyoctacosanyl, 1-hexacosanyloxyoctacosanyl, 1-pentacosanyloxyoctacosanyl, 1-tetracosanyloxyoctacosanyl, 1-tricosanyloxyoctacosanyl, 1-docosanyloxyoctacosanyl, 1-nonadecyloxyoctacosanyl, 1-octadecyloxyoctacosanyl, 1-heptadecyloxyoctacosanyl, 1-hexadecyloxyoctacosanyl, 1-hexadecyloxyoctacosanyl, 1-pentadecyloxyoctacosanyl, 1-tetradecyloxyoctacosanyl, 1-tridecyloxyoctacosanyl, 1-dodecyloxyoctacosanyl, 1-undecyloxyoctacosanyl, 1-decyloxyoctacosanyl, 1-nonyloxyoctacosanyl, 1-octyloxyoctacosanyl, 1-heptyloxyoctacosanyl, 1-hexyloxyoctacosanyl, 1-pentyloxyoctacosanyl, 1-butyloxyoctacosanyl, 1-propyloxyoctacosanyl, 1-ethyloxyoctacosanyl, 1-methyloxyoctacosanyl;

1-ethylthiopropyl, 1-methylthiopropyl, 1-propylbutyl, 1-ethylthiobutyl, 1-methylthiobutyl, 1-butylthiopentyl, 1-propylpentyl, 1-ethylthiopentyl, 1-methylthiopentyl, 1-pentylthiohexyl, 1-butylthiohexyl, 1-propylhexyl, 1-ethylthiohexyl, 1-methylthiohexyl, 1-hexylthioheptyl, 1-pentylthioheptyl, 1-butylthioheptyl, 1-propylheptyl, 1-ethylthioheptyl, 1-methylthioheptyl, 1-heptyloctyl, 1-hexylthiooctyl, 1-pentylthiooctyl, 1-butylthiooctyl, 1-propyloctyl, 1-ethylthiooctyl, 1-methylthiooctyl, 1-octylthiononyl, 1-heptylnonyl, 1-hexylthiononyl, 1-pentylthiononyl, 1-butylthiononyl, 1-propylnonyl, 1-ethylthiononyl, 1-methylthiononyl, 1-nonylthiodecyl, 1-octylthiodecyl, 1-heptyldecyl, 1-hexylthiodecyl, 1-pentylthiodecyl, 1-butylthiodecyl, 1-propyldecyl, 1-ethylthiodecyl, 1-methylthiodecyl, 1-decylthioundecyl, 1-nonylthioundecyl, 1-octylthioundecyl, 1-heptylundecyl, 1-hexylthioundecyl, 1-pentylthioundecyl, 1-butylthioundecyl, 1-propylundecyl, 1-ethylthioundecyl, 1-methylthioundecyl, 1-undecylthiododecyl, 1-decylthiododecyl, 1-nonylthiododecyl, 1-octylthiododecyl, 1-heptyldodecyl, 1-hexylthiododecyl, 1-pentylthiododecyl, 1-butylthiododecyl, 1-propyldodecyl, 1-ethylthiododecyl, 1-methylthiododecyl, 1-dodecylthiotridecyl, 1-undecylthiotridecyl, 1-decylthiotridecyl, 1-nonylthiotridecyl, 1-octylthiotridecyl, 1-heptyltridecyl, 1-hexylthiotridecyl, 1-pentylthiotridecyl, 1-butylthiotridecyl, 1-propyltridecyl, 1-ethylthiotridecyl, 1-methylthiotridecyl, 1-tridecylthiotetradecyl, 1-undecylthiotetradecyl, 1-decylthiotetradecyl, 1-nonylthiotetradecyl, 1-octylthiotetradecyl, 1-hetyltetradecyl, 1-hexylthiotetradecyl, 1-pentyltetradecyl, 1-butylthiotetradecyl, 1-propyltetradecyl, 1-ethylthiotetradecyl, 1-methylthiotetradecyl, 1-pentadecylthiohexadecyl, 1-tetradecylthiohexadecyl, 1-tridecylthiohexadecyl, 1-dodecylthiohexadecyl, 1-undecylthiohexadecyl, 1-decylthiohexadecyl, 1-nonylthiohexadecyl, 1-octylthiohexadecyl, 1-heptylhexadecyl, 1-hexylthiohexadecyl, 1-pentylthiohexadecyl, 1-butylthiohexadecyl, 1-propylhexadecyl, 1-ethylthiohexadecyl, 1-methylthiohexadecyl, 1-hexadecylthiooctadecyl, 1-pentadecylthiooctadecyl, 1-tetradecylthiooctadecyl, 1-tridecylthiooctadecyl, 1-dodecylthiooctadecyl, 1-undecylthiooctadecyl, 1-decylthiooctadecyl, 1-nonylthiooctadecyl, 1-octylthiooctadecyl, 1-heptyloctadecyl, 1-hexylthiooctadecyl, 1-pentylthiooctadecyl, 1-butylthiooctadecyl, 1-propyloctadecyl, 1-ethylthiooctadecyl, 1-methylthiooctadecyl, 1-nonadecylthioeicosanyl, 1-octadecylthioeicosanyl, 1-heptadecylthioeicosanyl, 1-hexadecylthioeicosanyl, 1-pentadecylthioeicosanyl, 1-tetradecylthioeicosanyl, 1-tridecylthioeicosanyl, 1-dodecylthioeicosanyl, 1-undecylthioeicosanyl, 1-decylthioeicosanyl, 1-nonylthioeicosanyl, 1-octylthioeicosanyl, 1-heptyleicosanyl, 1-hexylthioeicosanyl, 1-pentylthioeicosanyl, 1-butylthioeicosanyl, 1-propyleicosanyl, 1-ethylthioeicosanyl, 1-methyleicosanyl, 1-eicosanylthiodocosanyl, 1-nonadecylthiodocosanyl, 1-octadecylthiodocosanyl, 1-heptadecylthiodocosanyl, 1-hexadecylthiodocosanyl, 1-pentadecylthiodocosanyl, 1-tetradecylthiodocosanyl, 1-tridecylthiodocosanyl, 1-undecylthiodocosanyl, 1-decylthiodocosanyl, 1-nonylthiodocosanyl, 1-octylthiodocosanyl, 1-heptyldocosanyl, 1-hexylthiodocosanyl, 1-pentylthiodocosanyl, 1-butylthiodocosanyl, 1-propyldocosanyl, 1-ethylthiodocosanyl, 1-methylthiodocosanyl, 1-tricosanylthiotetracosanyl, 1-docosanylthiotetracosanyl, 1-nonadecylthiotetracosanyl, 1-octadecylthiotetracosanyl, 1-heptadecylthiotetracosanyl, 1-hexadecylthiotetracosanyl, 1-pentadecylthiotetracosanyl, 1-pentadecylthiotetracosanyl, 1-tetradecylthiotetracosanyl, 1-tridecylthiotetracosanyl, 1-dodecylthiotetracosanyl, 1-undecylthiotetracosanyl, 1-decylthiotetracosanyl, 1-nonylthiotetracosanyl, 1-octylthiotetracosanyl, 1-heptyltetracosanyl, 1-hexylthiotetracosanyl, 1-pentylthiotetracosanyl, 1-butylthiotetracosanyl, 1-propyltetracosanyl, 1-ethylthiotetracosanyl, 1-methylthiotetracosanyl, 1-heptacosanylthiooctacosanyl, 1-hexacosanylthiooctacosanyl, 1-pentacosanylthiooctacosanyl, 1-tetracosanylthiooctacosanyl, 1-tricosanylthiooctacosanyl, 1-docosanylthiooctacosanyl, 1-nonadecylthiooctacosanyl, 1-octadecylthiooctacosanyl, 1-heptadecylthiooctacosanyl, 1-hexadecylthiooctacosanyl, 1-hexadecylthiooctacosanyl, 1-pentadecylthiooctacosanyl, 1-tetradecylthiooctacosanyl, 1-tridecylthiooctacosanyl, 1-dodecylthiooctacosanyl, 1-undecylthiooctacosanyl, 1-decylthiooctacosanyl, 1-nonylthiooctacosanyl, 1-octylthiooctacosanyl, 1-heptyloctacosanyl, 1-hexylthiooctacosanyl, 1-pentylthiooctacosanyl, 1-butylthiooctacosanyl, 1-propylthiooctacosanyl, 1-ethylthiooctacosanyl, 1-methylthiooctacosanyl;

in which q is 1, for example 2-ethylpropyl, 2-methylpropyl, 2-propylbutyl, 2-ethylbutyl, 2-methylbutyl, 2-butylpentyl, 2-propylpentyl, 2-ethylpentyl, 2-methylpentyl, 2-pentylhexyl, 2-butylhexyl, 2-propylhexyl, 2-ethylhexyl, 2-methylhexyl, 2-hexylheptyl, 2-pentylheptyl, 2-butylheptyl, 2-propylheptyl, 2-ethylheptyl, 2-methylheptyl, 2-heptyloctyl, 2-hexyloctyl, 2-pentyloctyl, 2-butyloctyl, 2-propyloctyl, 2-ethyloctyl, 2-methyloctyl, 2-octylnonyl, 2-heptylnonyl, 2-hexylnonyl, 2-pentylnonyl, 2-butylnonyl, 2-propylnonyl, 2-ethylnonyl, 2-methylnonyl, 2-nonyldecyl, 2-octyldecyl, 2-heptyldecyl, 2-hexyldecyl, 2-pentyldecyl, 2-butyldecyl, 2-propyldecyl, 2-ethyldecyl, 2-methyldecyl, 2-decylundecyl, 2-nonylundecyl, 2-octylundecyl, 2-heptylundecyl, 2-hexylundecyl, 2-pentylundecyl, 2-butylundecyl, 2-propylundecyl, 2-ethylundecyl, 2-methylundecyl, 2-undecyldodecyl, 2-decyldodecyl, 2-nonyldodecyl, 2-octyldodecyl, 2-heptyldodecyl, 2-hexyldodecyl, 2-pentyldodecyl, 2-butyldodecyl, 2-propyldodecyl, 2-ethyldodecyl, 2-methyldodecyl, 2-dodecyltridecyl, 2-undecyltridecyl, 2-decyltridecyl, 2-nonyltridecyl, 2-octyltridecyl, 2-heptyltridecyl, 2-hexyltridecyl, 2-pentyltridecyl, 2-butyltridecyl, 2-propyltridecyl, 2-ethyltridecyl, 2-methyltridecyl, 2-tridecyltetradecyl, 2-undecyltetradecyl, 2-decyltetradecyl, 2-nonyltetradecyl, 2-octyltetradecyl, 2-hetyltetradecyl, 2-hexyltetradecyl, 2-pentyltetradecyl, 2-butyltetradecyl, 2-propyltetradecyl, 2-ethyltetradecyl, 2-methyltetradecyl, 2-pentadecylhexadecyl, 2-tetradecylhexadecyl, 2-tridecylhexadecyl, 2-dodecylhexadecyl, 2-undecylhexadecyl, 2-decylhexadecyl, 2-nonylhexadecyl, 2-octylhexadecyl, 2-heptyihexadecyl, 2-hexylhexadecyl, 2-pentylhexadecyl, 2-butylhexadecyl, 2-propylhexadecyl, 2-ethylhexadecyl, 2-methylhexadecyl, 2-hexadecyloctadecyl, 2-pentadecyloctadecyl, 2-tetradecyloctadecyl, 2-tridecyloctadecyl, 2-dodecyloctadecyl, 2-undecyloctadecyl, 2-decyloctadecyl, 2-nonyloctadecyl, 2-octyloctadecyl, 2-heptyloctadecyl, 2-hexyloctadecyl, 2-pentyloctadecyl, 2-butyloctadecyl, 2-propyloctadecyl, 2-ethyloctadecyl, 2-methyloctadecyl, 2-nonadecyleicosanyl, 2-octadecyleicosanyl, 2-heptadecyleicosanyl, 2-hexadecyleicosanyl, 2-pentadecyleicosanyl, 2-tetradecyleicosanyl, 2-tridecyleicosanyl, 2-dodecyleicosanyl, 2-undecyleicosanyl, 2-decyleicosanyl, 2-nonyleicosanyl, 2-octyleicosanyl, 2-heptyleicosanyl, 2-hexyleicosanyl, 2-pentyleicosanyl, 2-butyleicosanyl, 2-propyleicosanyl, 2-ethyleicosanyl, 2-methyleicosanyl, 2-eicosanyldocosanyl, 2-nonadecyldocosanyl, 2-octadecyldocosanyl, 2-heptadecyldocosanyl, 2-hexadecyldocosanyl, 2-pentadecyldocosanyl, 2-tetradecyldocosanyl, 2-tridecyldocosanyl, 2-undecyldocosanyl, 2-decyldocosanyl, 2-nonyldocosanyl, 2-octyldocosanyl, 2-heptyldocosanyl, 2-hexyldocosanyl, 2-pentyldocosanyl, 2-butyldocosanyl, 2-propyldocosanyl, 2-ethyldocosanyl, 2-methyldocosanyl, 2-tricosanyltetracosanyl, 2-docosanyltetracosanyl, 2-nonadecyltetracosanyl, 2-octadecyltetracosanyl, 2-heptadecyltetracosanyl, 2-hexadecyltetracosanyl, 2-pentadecyltetracosanyl, 2-pentadecyltetracosanyl, 2-tetradecyltetracosanyl, 2-tridecyltetracosanyl, 2-dodecyltetracosanyl, 2-undecyltetracosanyl, 2-decyltetracosanyl, 2-nonyltetracosanyl, 2-octyltetracosanyl, 2-heptyltetracosanyl, 2-hexyltetracosanyl, 2-pentyltetracosanyl, 2-butyltetracosanyl, 2-propyltetracosanyl, 2-ethyltetracosanyl, 2-methyltetracosanyl, 2-heptacosanyloctacosanyl, 2-hexacosanyloctacosanyl, 2-pentacosanyloctacosanyl, 2-tetracosanyloctacosanyl, 2-tricosanyloctacosanyl, 2-docosanyloctacosanyl, 2-nonadecyloctacosanyl, 2-octadecyloctacosanyl, 2-heptadecyloctacosanyl, 2-hexadecyloctacosanyl, 2-hexadecyloctacosanyl, 2-pentadecyloctacosanyl, 2-tetradecyloctacosanyl, 2-tridecyloctacosanyl, 2-dodecyloctacosanyl, 2-undecyloctacosanyl, 2-decyloctacosanyl, 2-nonyloctacosanyl, 2-octyloctacosanyl, 2-heptyloctacosanyl, 2-hexyloctacosanyl, 2-pentyloctacosanyl, 2-butyloctacosanyl, 2-propyloctacosanyl, 2-ethyloctacosanyl, 2-methyloctacosanyl;

in which q is 2, such as 3-ethylpropyl, 3-methylpropyl, 3-propylbutyl, 3-ethylbutyl, 3-methylbutyl, 3-butylpentyl, 3-propylpentyl, 3-ethylpentyl, 3-methylpentyl, 3-pentylhexyl, 3-butylhexyl, 3-propylhexyl, 3-ethylhexyl, 3-methylhexyl, 3-hexylheptyl, 3-pentylheptyl, 3-butylheptyl, 3-propylheptyl, 3-ethylheptyl, 3-methylheptyl, 3-heptyloctyl, 3-hexyloctyl, 3-pentyloctyl, 3-butyloctyl, 3-propyloctyl, 3-ethyloctyl, 3-methyloctyl, 3-octylnonyl, 3-heptylnonyl, 3-hexylnonyl, 3-pentylnonyl, 3-butylnonyl, 3-propylnonyl, 3-ethylnonyl, 3-methylnonyl, 3-nonyldecyl, 3-octyldecyl, 3-heptyldecyl, 3-hexyldecyl, 3-pentyldecyl, 3-butyldecyl, 3-propyldecyl, 3-ethyldecyl, 3-methyldecyl, 3-decylundecyl, 3-nonylundecyl, 3-octylundecyl, 3-heptylundecyl, 3-hexylundecyl, 3-pentylundecyl, 3-butylundecyl, 3-propylundecyl, 3-ethylundecyl, 3-methylundecyl, 3-undecyldodecyl, 3-decyldodecyl, 3-nonyldodecyl, 3-octyldodecyl, 3-heptyldodecyl, 3-hexyldodecyl, 3-pentyldodecyl, 3-butyldodecyl, 3-propyldodecyl, 3-ethyldodecyl, 3-methyldodecyl, 3-dodecyltridecyl, 3-undecyltridecyl, 3-decyltridecyl, 3-nonyltridecyl, 3-octyltridecyl, 3-heptyltridecyl, 3-hexyltridecyl, 3-pentyltridecyl, 3-butyltridecyl, 3-propyltridecyl, 3-ethyltridecyl, 3-methyltridecyl, 3-tridecyltetradecyl, 3-undecyltetradecyl, 3-decyltetradecyl, 3-nonyltetradecyl, 3-octyltetradecyl, 3-hetyltetradecyl, 3-hexyltetradecyl, 3-pentyltetradecyl, 3-butyltetradecyl, 3-propyltetradecyl, 3-ethyltetradecyl, 3-methyltetradecyl, 3-pentadecylhexadecyl, 3-tetradecylhexadecyl, 3-tridecylhexadecyl, 3-dodecylhexadecyl, 3-undecylhexadecyl, 3-decylhexadecyl, 3-nonylhexadecyl, 3-octylhexadecyl, 3-heptylhexadecyl, 3-hexylhexadecyl, 3-pentylhexadecyl, 3-butylhexadecyl, 3-propylhexadecyl, 3-ethylhexadecyl, 3-methylhexadecyl, 3-hexadecyloctadecyl, 3-pentadecyloctadecyl, 3-tetradecyloctadecyl, 3-tridecyloctadecyl, 3-dodecyloctadecyl, 3-undecyloctadecyl, 3-decyloctadecyl, 3-nonyloctadecyl, 3-octyloctadecyl, 3-heptyloctadecyl, 3-hexyloctadecyl, 3-pentyloctadecyl, 3-butyloctadecyl, 3-propyloctadecyl, 3-ethyloctadecyl, 3-methyloctadecyl, 3-nonadecyleicosanyl, 3-octadecyleicosanyl, 3-heptadecyleicosanyl, 3-hexadecyleicosanyl, 3-pentadecyleicosanyl, 3-tetradecyleicosanyl, 3-tridecyleicosanyl, 3-dodecyleicosanyl, 3-undecyleicosanyl, 3-decyleicosanyl, 3-nonyleicosanyl, 3-octyleicosanyl, 3-heptyleicosanyl, 3-hexyleicosanyl, 3-pentyleicosanyl, 3-butyleicosanyl, 3-propyleicosanyl, 3-ethyleicosanyl, 3-methyleicosanyl, 3-eicosanyldocosanyl, 3-nonadecyldocosanyl, 3-octadecyldocosanyl, 3-heptadecyldocosanyl, 3-hexadecyldocosanyl, 3-pentadecyldocosanyl, 3-tetradecyldocosanyl, 3-tridecyldocosanyl, 3-undecyldocosanyl, 3-decyldocosanyl, 3-nonyldocosanyl, 3-octyldocosanyl, 3-heptyldocosanyl, 3-hexyldocosanyl, 3-pentyldocosanyl, 3-butyldocosanyl, 3-propyldocosanyl, 3-ethyldocosanyl, 3-methyldocosanyl, 3-tricosanyltetracosanyl, 3-docosanyltetracosanyl, 3-nonadecyltetracosanyl, 3-octadecyltetracosanyl, 3-heptadecyltetracosanyl, 3-hexadecyltetracosanyl, 3-pentadecyltetracosanyl, 3-pentadecyltetracosanyl, 3-tetradecyltetracosanyl, 3-tridecyltetracosanyl, 3-dodecyltetracosanyl, 3-undecyltetracosanyl, 3-decyltetracosanyl, 3-nonyltetracosanyl, 3-octyltetracosanyl, 3-heptyltetracosanyl, 3-hexyltetracosanyl, 3-pentyltetracosanyl, 3-butyltetracosanyl, 3-propyltetracosanyl, 3-ethyltetracosanyl, 3-methyltetracosanyl, 3-heptacosanyloctacosanyl, 3-hexacosanyloctacosanyl, 3-pentacosanyloctacosanyl, 3-tetracosanyloctacosanyl, 3-tricosanyloctacosanyl, 3-docosanyloctacosanyl, 3-nonadecyloctacosanyl, 3-octadecyloctacosanyl, 3-heptadecyloctacosanyl, 3-hexadecyloctacosanyl, 3-hexadecyloctacosanyl, 3-pentadecyloctacosanyl, 3-tetradecyloctacosanyl, 3-tridecyloctacosanyl, 3-dodecyloctacosanyl, 3-undecyloctacosanyl, 3-decyloctacosanyl, 3-nonyloctacosanyl, 3-octyloctacosanyl, 3-heptyloctacosanyl, 3-hexyloctacosanyl, 3-pentyloctacosanyl, 3-butyloctacosanyl, 3-propyloctacosanyl, 3-ethyloctacosanyl, 3-methyloctacosanyl, in which q is 3, such as 4-butylpentyl, 4-propylpentyl, 4-ethylpentyl, 4-methylpentyl, 4-pentylhexyl, 4-butylhexyl, 4-propylhexyl, 4-ethylhexyl, 4-methylhexyl, 4-hexylheptyl, 4-pentylheptyl, 4-butylheptyl, 4-propylheptyl, 4-ethylheptyl, 4-methylheptyl, 4-heptyloctyl, 4-hexyloctyl, 4-pentyloctyl, 4-butyloctyl, 4-propyloctyl, 4-ethyloctyl, 4-methyloctyl, 4-octylnonyl, 4-heptylnonyl, 4-hexylnonyl, 4-pentylnonyl, 4-butylnonyl, 4-propylnonyl, 4-ethylnonyl, 4-methylnonyl, 4-nonyldecyl, 4-octyldecyl, 4-heptyldecyl, 4-hexyldecyl, 4-pentyldecyl, 4-butyldecyl, 4-propyldecyl, 4-ethyldecyl, 4-methyldecyl, 4-decylundecyl, 4-nonylundecyl, 4-octylundecyl, 4-heptylundecyl, 4-hexylundecyl, 4-pentylundecyl, 4-butylundecyl, 4-propylundecyl, 4-ethylundecyl, 4-methylundecyl, 4-undecyldodecyl, 4-decyldodecyl, 4-nonyldodecyl, 4-octyldodecyl, 4-heptyldodecyl, 4-hexyldodecyl, 4-pentyldodecyl, 4-butyldodecyl, 4-pro pyldodecyl, 4-ethyldodecyl, 4-methyldodecyl, 4-dodecyltridecyl, 4-undecyltridecyl, 4-decyltridecyl, 4-nonyltridecyl, 4-octyltridecyl, 4-heptyltridecyl, 4-hexyltridecyl, 4-pentyltridecyl, 4-butyltridecyl, 4-propyltridecyl, 4-ethyltridecyl, 4-methyltridecyl, 4-tridecyltetradecyl, 4-undecyltetradecyl, 4-decyltetradecyl, 4-nonyltetradecyl, 4-octyltetradecyl, 4-hetyltetradecyl, 4-hexyltetradecyl, 4-pentyltetradecyl, 4-butyltetradecyl, 4-propyltetradecyl, 4-ethyltetradecyl, 4-methyltetradecyl, 4-pentadecylhexadecyl, 4-tetradecylhexadecyl, 4-tridecylhexadecyl, 4-dodecylhexadecyl, 4-undecylhexadecyl, 4-decylhexadecyl, 4-nonyihexadecyl, 4-octylhexadecyl, 4-heptyihexadecyl, 4-hexylhexadecyl, 4-pentylhexadecyl, 4-butylhexadecyl, 4-propylhexadecyl, 4-ethylhexadecyl, 4-methylhexadecyl, 4-hexadecyloctadecyl, 4-pentadecyloctadecyl, 4-tetradecyloctadecyl, 4-tridecyloctadecyl, 4-dodecyloctadecyl, 4-undecyloctadecyl, 4-decyloctadecyl, 4-nonyloctadecyl, 4-octyloctadecyl, 4-heptyloctadecyl, 4-hexyloctadecyl, 4-pentyloctadecyl, 4-butyloctadecyl, 4-propyloctadecyl, 4-ethyloctadecyl, 4-methyloctadecyl, 4-nonadecyleicosanyl, 4-octadecyleicosanyl, 4-heptadecyleicosanyl, 4-hexadecyleicosanyl, 4-pentadecyleicosanyl, 4-tetradecyleicosanyl, 4-tridecyleicosanyl, 4-dodecyleicosanyl, 4-undecyleicosanyl, 4-decyleicosanyl, 4-nonyleicosanyl, 4-octyleicosanyl, 4-heptyleicosanyl, 4-hexyleicosanyl, 4-pentyleicosanyl, 4-butyleicosanyl, 4-propyleicosanyl, 4-ethyleicosanyl, 4-methyleicosanyl, 4-eicosanyldocosanyl, 4-nonadecyldocosanyl, 4-octadecyldocosanyl, 4-heptadecyldocosanyl, 4-hexadecyldocosanyl, 4-pentadecyldocosanyl, 4-tetradecyldocosanyl, 4-tridecyldocosanyl, 4-undecyldocosanyl, 4-decyldocosanyl, 4-nonyldocosanyl, 4-octyldocosanyl, 4-heptyldocosanyl, 4-hexyldocosanyl, 4-pentyldocosanyl, 4-butyldocosanyl, 4-propyldocosanyl, 4-ethyldocosanyl, 4-methyldocosanyl, 4-tricosanyltetracosanyl, 4-docosanyltetracosanyl, 4-nonadecyltetracosanyl, 4-octadecyltetracosanyl, 4-heptadecyltetracosanyl, 4-hexadecyltetracosanyl, 4-pentadecyltetracosanyl, 4-pentadecyltetracosanyl, 4-tetradecyltetracosanyl, 4-tridecyltetracosanyl, 4-dodecyltetracosanyl, 4-undecyltetracosanyl, 4-decyltetracosanyl, 4-nonyltetracosanyl, 4-octyltetracosanyl, 4-heptyltetracosanyl, 4-hexyltetracosanyl, 4-pentyltetracosanyl, 4-butyltetracosanyl, 4-propyltetracosanyl, 4-ethyltetracosanyl, 4-methyltetracosanyl, 4-heptacosanyloctacosanyl, 4-hexacosanyloctacosanyl, 4-pentacosanyloctacosanyl, 4-tetracosanyloctacosanyl, 4-tricosanyloctacosanyl, 4-docosanyloctacosanyl, 4-nonadecyloctacosanyl, 4-octadecyloctacosanyl, 4-heptadecyloctacosanyl, 4-hexadecyloctacosanyl, 4-hexadecyloctacosanyl, 4-pentadecyloctacosanyl, 4-tetradecyloctacosanyl, 4-tridecyloctacosanyl, 4-dodecyloctacosanyl, 4-undecyloctacosanyl, 4-decyloctacosanyl, 4-nonyloctacosanyl, 4-octyloctacosanyl, 4-heptyloctacosanyl, 4-hexyloctacosanyl, 4-pentyloctacosanyl, 4-butyloctacosanyl, 4-propyloctacosanyl, 4-ethyloctacosanyl, 4-methyloctacosanyl, in which q is 4, such as 5-pentylhexyl, 5-butylhexyl, 5-propylhexyl, 5-ethylhexyl, 5-methylhexyl, 5-hexylheptyl, 5-pentylheptyl, 5-butylheptyl, 5-propylheptyl, 5-ethylheptyl, 5-methylheptyl, 5-heptyloctyl, 5-hexyloctyl, 5-pentyloctyl, 5-butyloctyl, 5-propyloctyl, 5-ethyloctyl, 5-methyloctyl, 5-octylnonyl, 5-heptylnonyl, 5-hexylnonyl, 5-pentylnonyl, 5-butylnonyl, 5-propylnonyl, 5-ethylnonyl, 5-methylnonyl, 5-nonyldecyl, 5-octyldecyl, 5-heptyldecyl, 5-hexyldecyl, 5-pentyldecyl, 5-butyldecyl, 5-propyldecyl, 5-ethyldecyl, 5-methyldecyl, 5-decylundecyl, 5-nonylundecyl, 5-octylundecyl, 5-heptylundecyl, 5-hexylundecyl, 5-pentylundecyl, 5-butylundecyl, 5-propylundecyl, 5-ethylundecyl, 5-methylundecyl, 5-undecyldodecyl, 5-decyldodecyl, 5-nonyldodecyl, 5-octyldodecyl, 5-heptyldodecyl, 5-hexyldodecyl, 5-pentyldodecyl, 5-butyldodecyl, 5-propyldodecyl, 5-ethyldodecyl, 5-methyldodecyl, 5-dodecyltridecyl, 5-undecyltridecyl, 5-decyltridecyl, 5-nonyltridecyl, 5-octyltridecyl, 5-heptyltridecyl, 5-hexyltridecyl, 5-pentyltridecyl, 5-butyltridecyl, 5-propyltridecyl, 5-ethyltridecyl, 5-methyltridecyl, 5-tridecyltetradecyl, 5-undecyltetradecyl, 5-decyltetradecyl, 5-nonyltetradecyl, 5-octyltetradecyl, 5-hetyltetradecyl, 5-hexyltetradecyl, 5-pentyltetradecyl, 5-butyltetradecyl, 5-propyltetradecyl, 5-ethyltetradecyl, 5-methyltetradecyl, 5-pentadecylhexadecyl, 5-tetradecylhexadecyl, 5-tridecylhexadecyl, 5-dodecylhexadecyl, 5-undecylhexadecyl, 5-decylhexadecyl, 5-nonylhexadecyl, 5-octylhexadecyl, 5-heptyihexadecyl, 5-hexylhexadecyl, 5-pentylhexadecyl, 5-butylhexadecyl, 5-propylhexadecyl, 5-ethylhexadecyl, 5-methylhexadecyl, 5-hexadecyloctadecyl, 5-pentadecyloctadecyl, 5-tetradecyloctadecyl, 5-tridecyloctadecyl, 5-dodecyloctadecyl, 5-undecyloctadecyl, 5-decyloctadecyl, 5-nonyloctadecyl, 5-octyloctadecyl, 5-heptyloctadecyl, 5-hexyloctadecyl, 5-pentyloctadecyl, 5-butyloctadecyl, 5-propyloctadecyl, 5-ethyloctadecyl, 5-methyloctadecyl, 5-nonadecyleicosanyl, 5-octadecyleicosanyl, 5-heptadecyleicosanyl, 5-hexadecyleicosanyl, 5-pentadecyleicosanyl, 5-tetradecyleicosanyl, 5-tridecyleicosanyl, 5-dodecyleicosanyl, 5-undecyleicosanyl, 5-decyleicosanyl, 5-nonyleicosanyl, 5-octyleicosanyl, 5-heptyleicosanyl, 5-hexyleicosanyl, 5-pentyleicosanyl, 5-butyleicosanyl, 5-propyleicosanyl, 5-ethyleicosanyl, 5-methyleicosanyl, 5-eicosanyldocosanyl, 5-nonadecyldocosanyl, 5-octadecyldocosanyl, 5-heptadecyldocosanyl, 5-hexadecyldocosanyl, 5-pentadecyldocosanyl, 5-tetradecyldocosanyl, 5-tridecyldocosanyl, 5-undecyldocosanyl, 5-decyldocosanyl, 5-nonyldocosanyl, 5-octyldocosanyl, 5-heptyldocosanyl, 5-hexyldocosanyl, 5-pentyldocosanyl, 5-butyldocosanyl, 5-propyldocosanyl, 5-ethyldocosanyl, 5-methyldocosanyl, 5-tricosanyltetracosanyl, 5-docosanyltetracosanyl, 5-nonadecyltetracosanyl, 5-octadecyltetracosanyl, 5-heptadecyltetracosanyl, 5-hexadecyltetracosanyl, 5-pentadecyltetracosanyl, 5-pentadecyltetracosanyl, 5-tetradecyltetracosanyl, 5-tridecyltetracosanyl, 5-dodecyltetracosanyl, 5-undecyltetracosanyl, 5-decyltetracosanyl, 5-nonyltetracosanyl, 5-octyltetracosanyl, 5-heptyltetracosanyl, 5-hexyltetracosanyl, 5-pentyltetracosanyl, 5-butyltetracosanyl, 5-propyltetracosanyl, 5-ethyltetracosanyl, 5-methyltetracosanyl, 5-heptacosanyloctacosanyl, 5-hexacosanyloctacosanyl, 5-pentacosanyloctacosanyl, 5-tetracosanyloctacosanyl, 5-tricosanyloctacosanyl, 5-docosanyloctacosanyl, 5-nonadecyloctacosanyl, 5-octadecyloctacosanyl, 5-heptadecyloctacosanyl, 5-hexadecyloctacosanyl, 5-hexadecyloctacosanyl, 5-pentadecyloctacosanyl, 5-tetradecyloctacosanyl, 5-tridecyloctacosanyl, 5-dodecyloctacosanyl, 5-undecyloctacosanyl, 5-decyloctacosanyl, 5-nonyloctacosanyl, 5-octyloctacosanyl, 5-heptyloctacosanyl, 5-hexyloctacosanyl, 5-pentyloctacosanyl, 5-butyloctacosanyl, 5-propyloctacosanyl, 5-ethyloctacosanyl, 5-methyloctacosanyl, in which q is 5, for example 6-hexylheptyl, 6-pentylheptyl, 6-butylheptyl, 6-propylheptyl, 6-ethylheptyl, 6-methylheptyl, 6-heptyloctyl, 6-hexyloctyl, 6-pentyloctyl, 6-butyloctyl, 6-propyloctyl, 6-ethyloctyl, 6-methyloctyl, 6-octylnonyl, 6-heptylnonyl, 6-hexylnonyl, 6-pentylnonyl, 6-butylnonyl, 6-propylnonyl, 6-ethylnonyl, 6-methylnonyl, 6-nonyldecyl, 6-octyldecyl, 6-heptyldecyl, 6-hexyldecyl, 6-pentyldecyl, 6-butyldecyl, 6-propyldecyl, 6-ethyldecyl, 6-methyldecyl, 6-decylundecyl, 6-nonylundecyl, 6-octylundecyl, 6-heptylundecyl, 6-hexylundecyl, 6-pentylundecyl, 6-butylundecyl, 6-propylundecyl, 6-ethylundecyl, 6-methylundecyl, 6-undecyldodecyl, 6-decyldodecyl, 6-nonyldodecyl, 6-octyldodecyl, 6-heptyldodecyl, 6-hexyldodecyl, 6-pentyldodecyl, 6-butyldodecyl, 6-propyldodecyl, 6-ethyldodecyl, 6-methyldodecyl, 6-dodecyltridecyl, 6-undecyltridecyl, 6-decyltridecyl, 6-nonyltridecyl, 6-octyltridecyl, 6-heptyltridecyl, 6-hexyltridecyl, 6-pentyltridecyl, 6-butyltridecyl, 6-propyltridecyl, 6-ethyltridecyl, 6-methyltridecyl, 6-tridecyltetradecyl, 6-undecyltetradecyl, 6-decyltetradecyl, 6-nonyltetradecyl, 6-octyltetradecyl, 6-hetyltetradecyl, 6-hexyltetradecyl, 6-pentyltetradecyl, 6-butyltetradecyl, 6-propyltetradecyl, 6-ethyltetradecyl, 6-methyltetradecyl, 6-pentadecylhexadecyl, 6-tetradecylhexadecyl, 6-tridecylhexadecyl, 6-dodecylhexadecyl, 6-undecylhexadecyl, 6-decylhexadecyl, 6-nonylhexadecyl, 6-octylhexadecyl, 6-heptylhexadecyl, 6-hexylhexadecyl, 6-pentylhexadecyl, 6-butylhexadecyl, 6-propylhexadecyl, 6-ethylhexadecyl, 6-methylhexadecyl, 6-hexadecyloctadecyl, 6-pentadecyloctadecyl, 6-tetradecyloctadecyl, 6-tridecyloctadecyl, 6-dodecyloctadecyl, 6-undecyloctadecyl, 6-decyloctadecyl, 6-nonyloctadecyl, 6-octyloctadecyl, 6-heptyloctadecyl, 6-hexyloctadecyl, 6-pentyloctadecyl, 6-butyloctadecyl, 6-propyloctadecyl, 6-ethyloctadecyl, 6-methyloctadecyl, 6-nonadecyleicosanyl, 6-octadecyleicosanyl, 6-heptadecyleicosanyl, 6-hexadecyleicosanyl, 6-pentadecyleicosanyl, 6-tetradecyleicosanyl, 6-tridecyleicosanyl, 6-dodecyleicosanyl, 6-undecyleicosanyl, 6-decyleicosanyl, 6-nonyleicosanyl, 6-octyleicosanyl, 6-heptyleicosanyl, 6-hexyleicosanyl, 6-pentyleicosanyl, 6-butyleicosanyl, 6-propyleicosanyl, 6-ethyleicosanyl, 6-methyleicosanyl, 6-eicosanyldocosanyl, 6-nonadecyldocosanyl, 6-octadecyldocosanyl, 6-heptadecyldocosanyl, 6-hexadecyldocosanyl, 6-pentadecyldocosanyl, 6-tetradecyldocosanyl, 6-tridecyldocosanyl, 6-undecyldocosanyl, 6-decyldocosanyl, 6-nonyldocosanyl, 6-octyldocosanyl, 6-heptyldocosanyl, 6-hexyldocosanyl, 6-pentyldocosanyl, 6-butyldocosanyl, 6-propyldocosanyl, 6-ethyldocosanyl, 6-methyldocosanyl, 6-tricosanyltetracosanyl, 6-docosanyltetracosanyl, 6-nonadecyltetracosanyl, 6-octadecyltetracosanyl, 6-heptadecyltetracosanyl, 6-hexadecyltetracosanyl, 6-pentadecyltetracosanyl, 6-pentadecyltetracosanyl, 6-tetradecyltetracosanyl, 6-tridecyltetracosanyl, 6-dodecyltetracosanyl, 6-undecyltetracosanyl, 6-decyltetracosanyl, 6-nonyltetracosanyl, 6-octyltetracosanyl, 6-heptyltetracosanyl, 6-hexyltetracosanyl, 6-pentyltetracosanyl, 6-butyltetracosanyl, 6-propyltetracosanyl, 6-ethyltetracosanyl, 6-methyltetracosanyl, 6-heptacosanyloctacosanyl, 6-hexacosanyloctacosanyl, 6-pentacosanyloctacosanyl, 6-tetracosanyloctacosanyl, 6-tricosanyloctacosanyl, 6-docosanyloctacosanyl, 6-nonadecyloctacosanyl, 6-octadecyloctacosanyl, 6-heptadecyloctacosanyl, 6-hexadecyloctacosanyl, 6-pentadecyloctacosanyl, 6-tetradecyloctacosanyl, 6-tridecyloctacosanyl, 6-dodecyloctacosanyl, 6-undecyloctacosanyl, 6-decyloctacosanyl, 6-nonyloctacosanyl, 6-octyloctacosanyl, 6-heptyloctacosanyl, 6-hexyloctacosanyl, 6-pentyloctacosanyl, 6-butyloctacosanyl, 6-propyloctacosanyl, 6-ethyloctacosanyl, 6-methyloctacosanyl, in which q is 6, for example 7-heptyloctyl, 7-hexyloctyl, 7-pentyloctyl, 7-butyloctyl, 7-propyloctyl, 7-ethyloctyl, 7-methyloctyl, 7-octylnonyl, 7-heptylnonyl, 7-hexylnonyl, 7-pentylnonyl, 7-butylnonyl, 7-propylnonyl, 7-ethylnonyl, 7-methylnonyl, 7-nonyldecyl, 7-octyldecyl, 7-heptyldecyl, 7-hexyldecyl, 7-pentyldecyl, 7-butyldecyl, 7-propyldecyl, 7-ethyldecyl, 7-methyldecyl, 7-decylundecyl, 7-nonylundecyl, 7-octylundecyl, 7-heptylundecyl, 7-hexylundecyl, 7-pentylundecyl, 7-butylundecyl, 7-propylundecyl, 7-ethylundecyl, 7-methylundecyl, 7-undecyldodecyl, 7-decyldodecyl, 7-nonyldodecyl, 7-octyldodecyl, 7-heptyldodecyl, 7-hexyldodecyl, 7-pentyldodecyl, 7-butyldodecyl, 7-propyldodecyl, 7-ethyldodecyl, 7-methyldodecyl, 7-dodecyltridecyl, 7-undecyltridecyl, 7-decyltridecyl, 7-nonyltridecyl, 7-octyltridecyl, 7-heptyltridecyl, 7-hexyltridecyl, 7-pentyltridecyl, 7-butyltridecyl, 7-propyltridecyl, 7-ethyltridecyl, 7-methyltridecyl, 7-tridecyltetradecyl, 7-undecyltetradecyl, 7-decyltetradecyl, 7-nonyltetradecyl, 7-octyltetradecyl, 7-hetyltetradecyl, 7-hexyltetradecyl, 7-pentyltetradecyl, 7-butyltetradecyl, 7-propyltetradecyl, 7-ethyltetradecyl, 7-methyltetradecyl, 7-pentadecylhexadecyl, 7-tetradecylhexadecyl, 7-tridecylhexadecyl, 7-dodecylhexadecyl, 7-undecylhexadecyl, 7-decylhexadecyl, 7-nonylhexadecyl, 7-octylhexadecyl, 7-heptylhexadecyl, 7-hexylhexadecyl, 7-pentylhexadecyl, 7-butylhexadecyl, 7-propylhexadecyl, 7-ethylhexadecyl, 7-methylhexadecyl, 7-hexadecyloctadecyl, 7-pentadecyloctadecyl, 7-tetradecyloctadecyl, 7-tridecyloctadecyl, 7-dodecyloctadecyl, 7-undecyloctadecyl, 7-decyloctadecyl, 7-nonyloctadecyl, 7-octyloctadecyl, 7-heptyloctadecyl, 7-hexyloctadecyl, 7-pentyloctadecyl, 7-butyloctadecyl, 7-propyloctadecyl, 7-ethyloctadecyl, 7-methyloctadecyl, 7-nonadecyleicosanyl, 7-octadecyleicosanyl, 7-heptadecyleicosanyl, 7-hexadecyleicosanyl, 7-pentadecyleicosanyl, 7-tetradecyleicosanyl, 7-tridecyleicosanyl, 7-dodecyleicosanyl, 7-undecyleicosanyl, 7-decyleicosanyl, 7-nonyleicosanyl, 7-octyleicosanyl, 7-heptyleicosanyl, 7-hexyleicosanyl, 7-pentyleicosanyl, 7-butyleicosanyl, 7-propyleicosanyl, 7-ethyleicosanyl, 7-methyleicosanyl, 7-eicosanyldocosanyl, 7-nonadecyldocosanyl, 7-octadecyldocosanyl, 7-heptadecyldocosanyl, 7-hexadecyldocosanyl, 7-pentadecyldocosanyl, 7-tetradecyldocosanyl, 7-tridecyldocosanyl, 7-undecyldocosanyl, 7-decyldocosanyl, 7-nonyldocosanyl, 7-octyldocosanyl, 7-heptyldocosanyl, 7-hexyldocosanyl, 7-pentyldocosanyl, 7-butyldocosanyl, 7-propyldocosanyl, 7-ethyldocosanyl, 7-methyldocosanyl, 7-tricosanyltetracosanyl, 7-docosanyltetracosanyl, 7-nonadecyltetracosanyl, 7-octadecyltetracosanyl, 7-heptadecyltetracosanyl, 7-hexadecyltetracosanyl, 7-pentadecyltetracosanyl, 7-pentadecyltetracosanyl, 7-tetradecyltetracosanyl, 7-tridecyltetracosanyl, 7-dodecyltetracosanyl, 7-undecyltetracosanyl, 7-decyltetracosanyl, 7-nonyltetracosanyl, 7-octyltetracosanyl, 7-heptyltetracosanyl, 7-hexyltetracosanyl, 7-pentyltetracosanyl, 7-butyltetracosanyl, 7-propyltetracosanyl, 7-ethyltetracosanyl, 7-methyltetracosanyl, 7-heptacosanyloctacosanyl, 7-hexacosanyloctacosanyl, 7-pentacosanyloctacosanyl, 7-tetracosanyloctacosanyl, 7-tricosanyloctacosanyl, 7-docosanyloctacosanyl, 7-nonadecyloctacosanyl, 7-octadecyloctacosanyl, 7-heptadecyloctacosanyl, 7-hexadecyloctacosanyl, 7-hexadecyloctacosanyl, 7-pentadecyloctacosanyl, 7-tetradecyloctacosanyl, 7-tridecyloctacosanyl, 7-dodecyloctacosanyl, 7-undecyloctacosanyl, 7-decyloctacosanyl, 7-nonyloctacosanyl, 7-octyloctacosanyl, 7-heptyloctacosanyl, 7-hexyloctacosanyl, 7-pentyloctacosanyl, 7-butyloctacosanyl, 7-propyloctacosanyl, 7-ethyloctacosanyl, 7-methyloctacosanyl.
Preference is given to the following compounds:
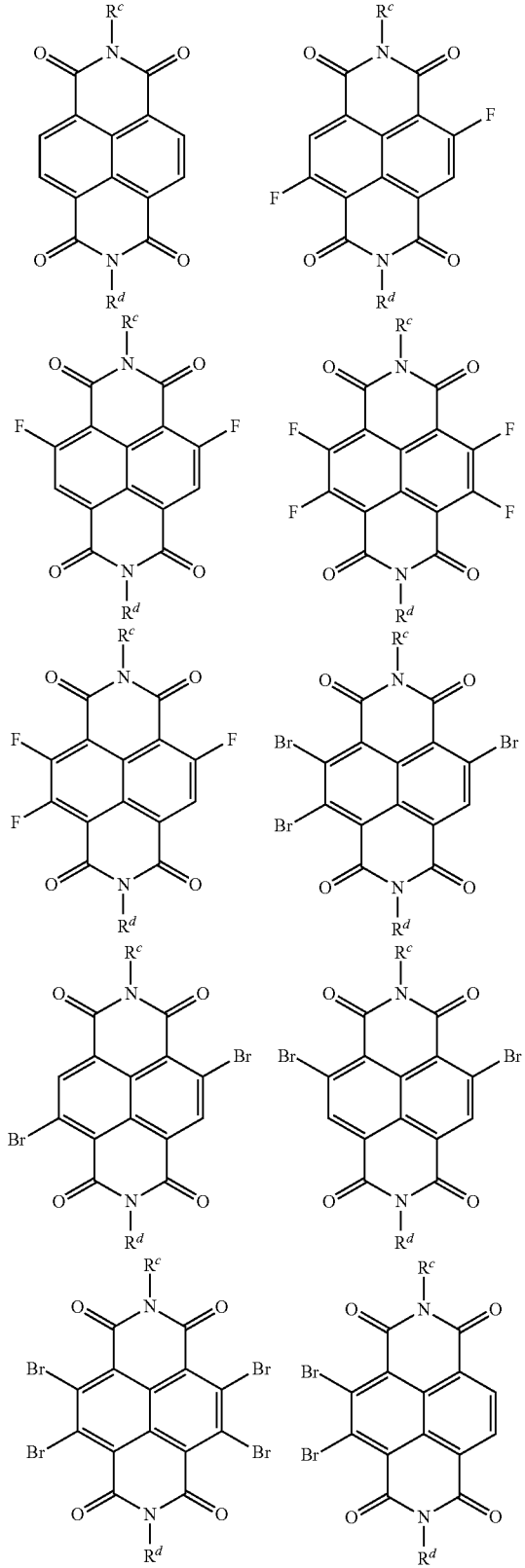
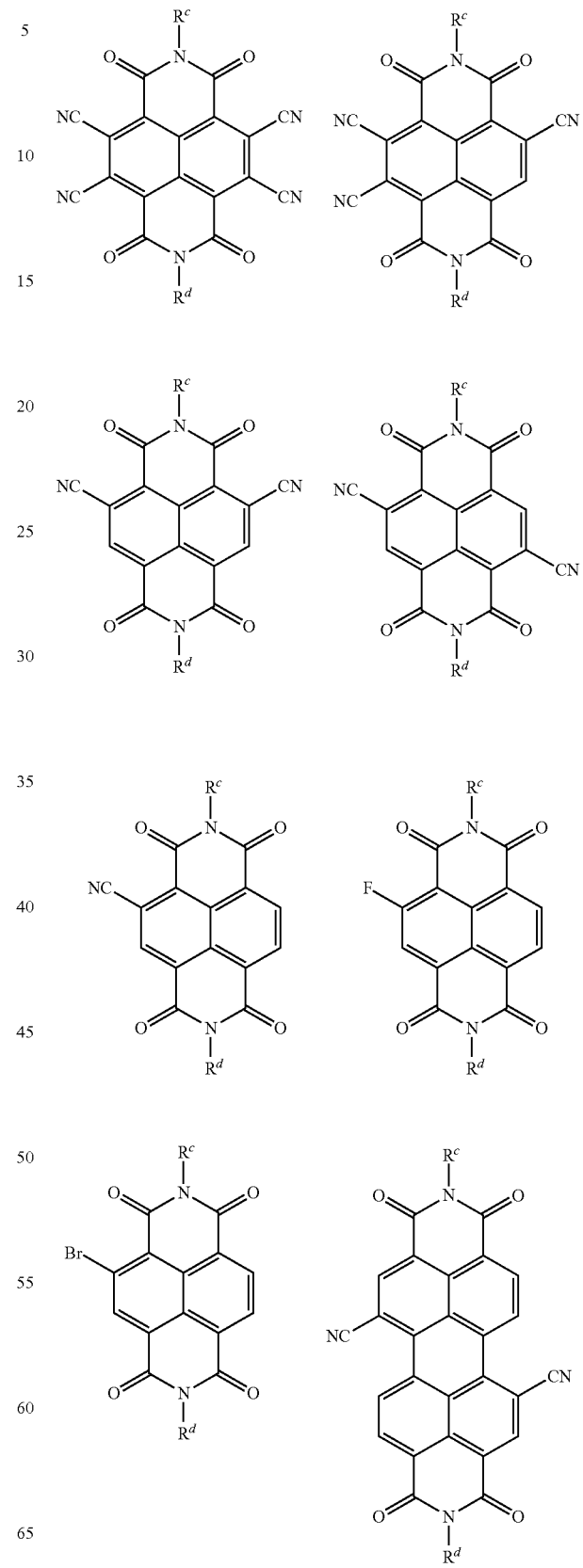

-continued
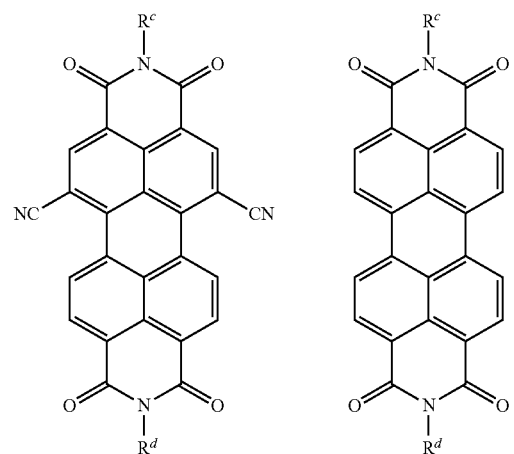 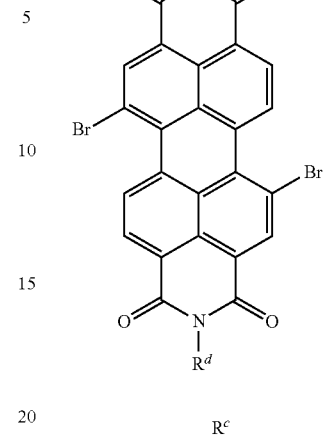
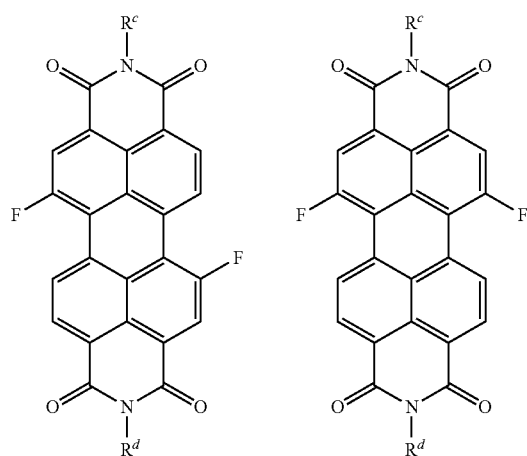 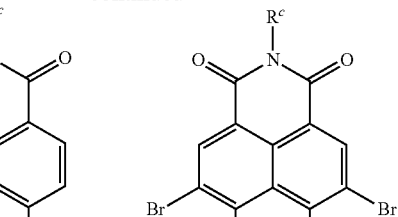
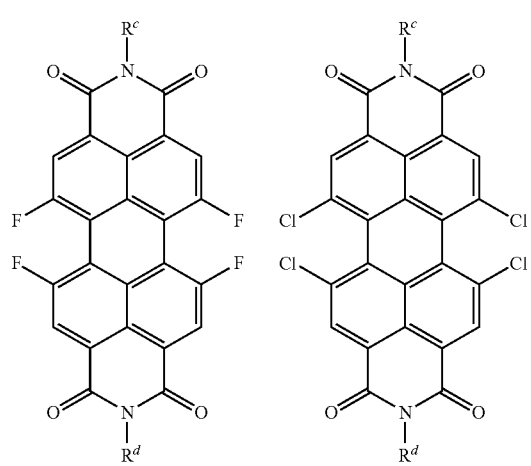 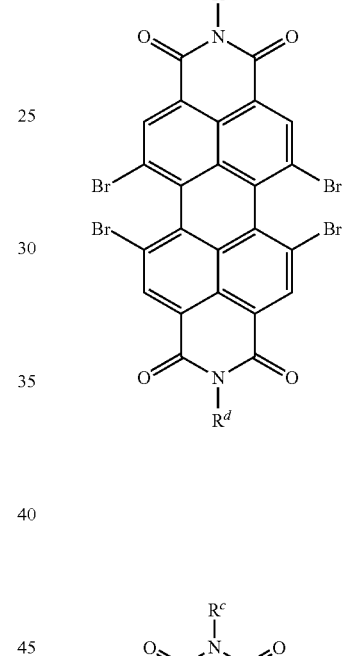
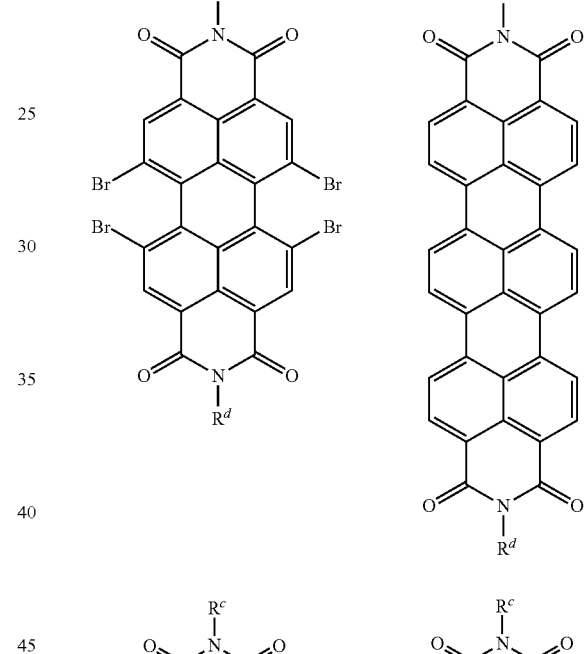
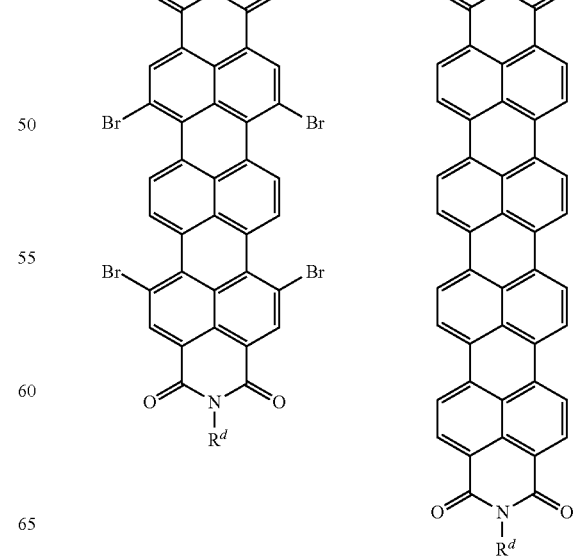

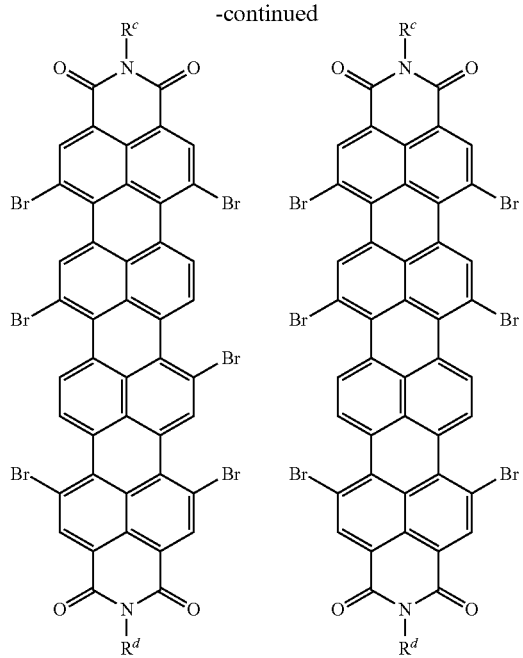
With regard to the definitions of the $R^c$ and $R^d$ groups, reference is made to the remarks made at the outset.
Preferred compounds are:
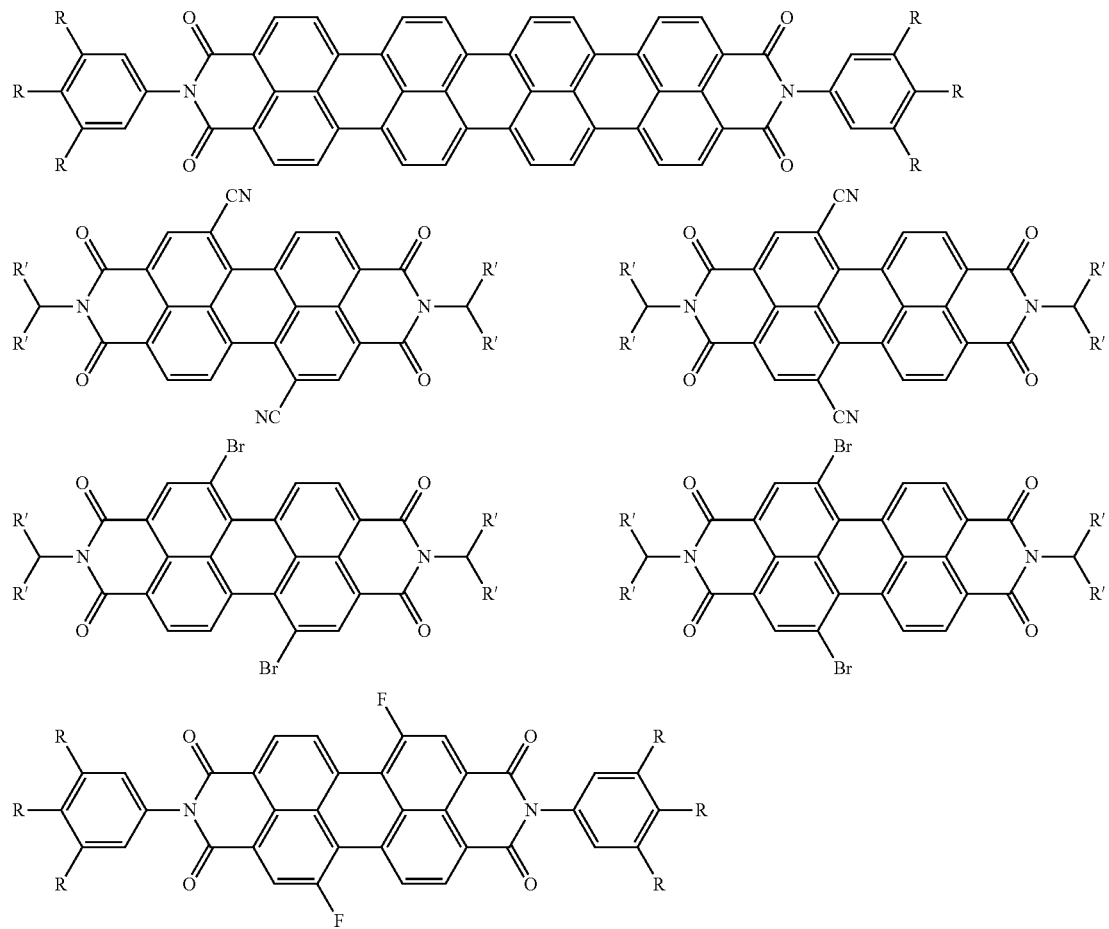

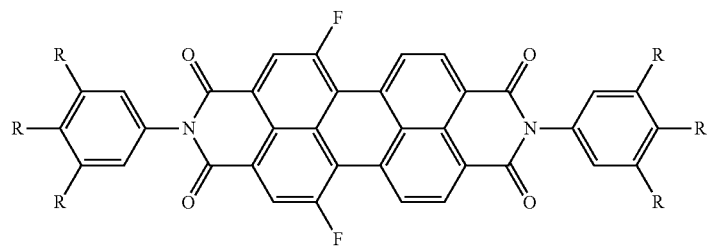
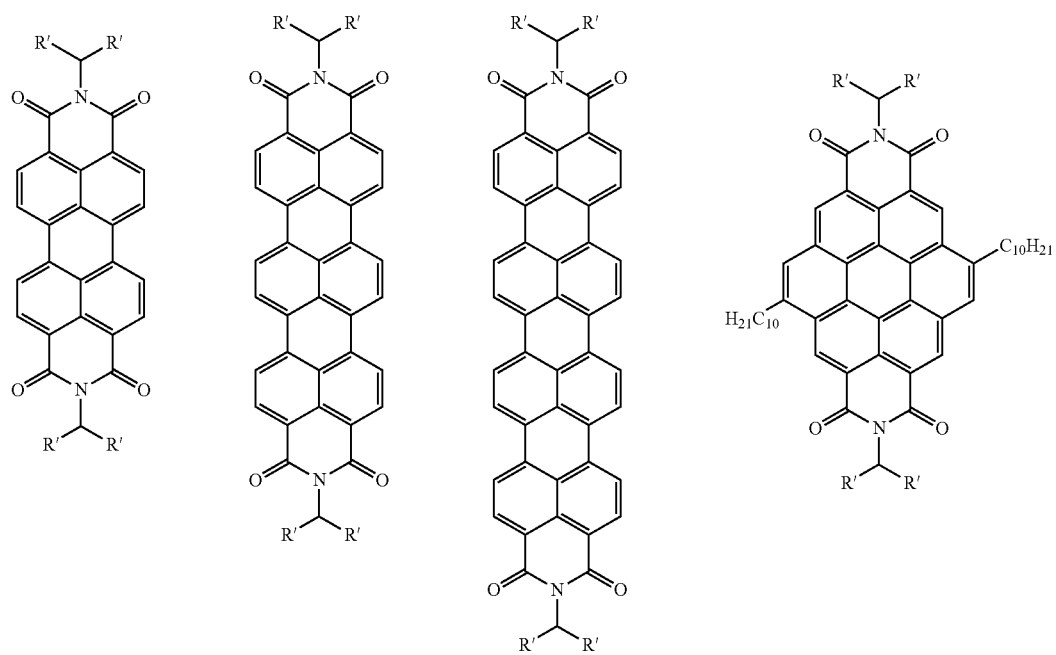
in which R and R' are each $C_4$-$C_{18}$-alkyl, preferably $C_5$-$C_{12}$-alkyl. R' is preferably $C_4$-$C_8$-alkyl, more preferably $C_5$-$C_7$-alkyl.
Some particularly preferred inventive compounds are reproduced below:
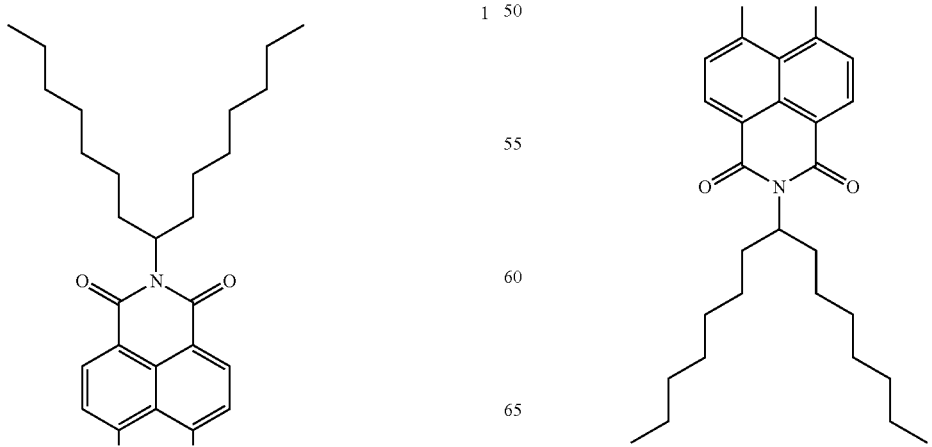

-continued

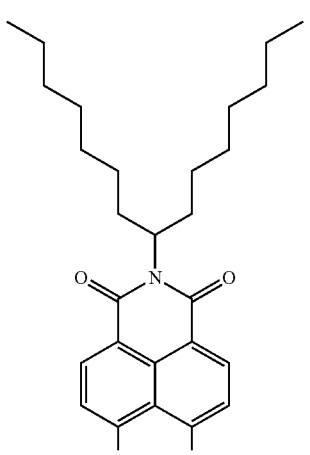
2

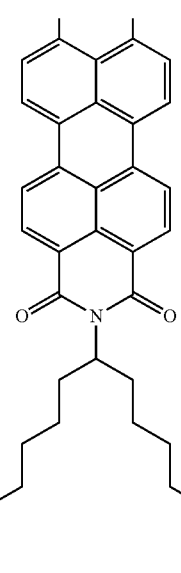
3

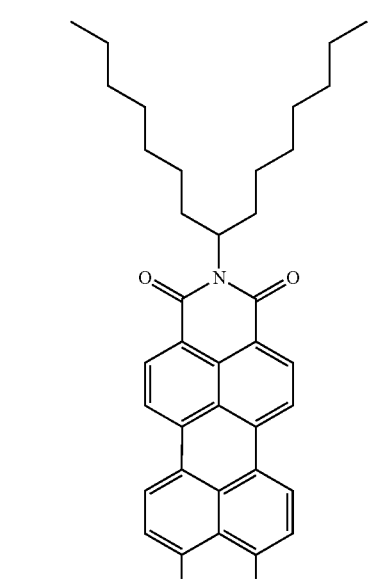

-continued

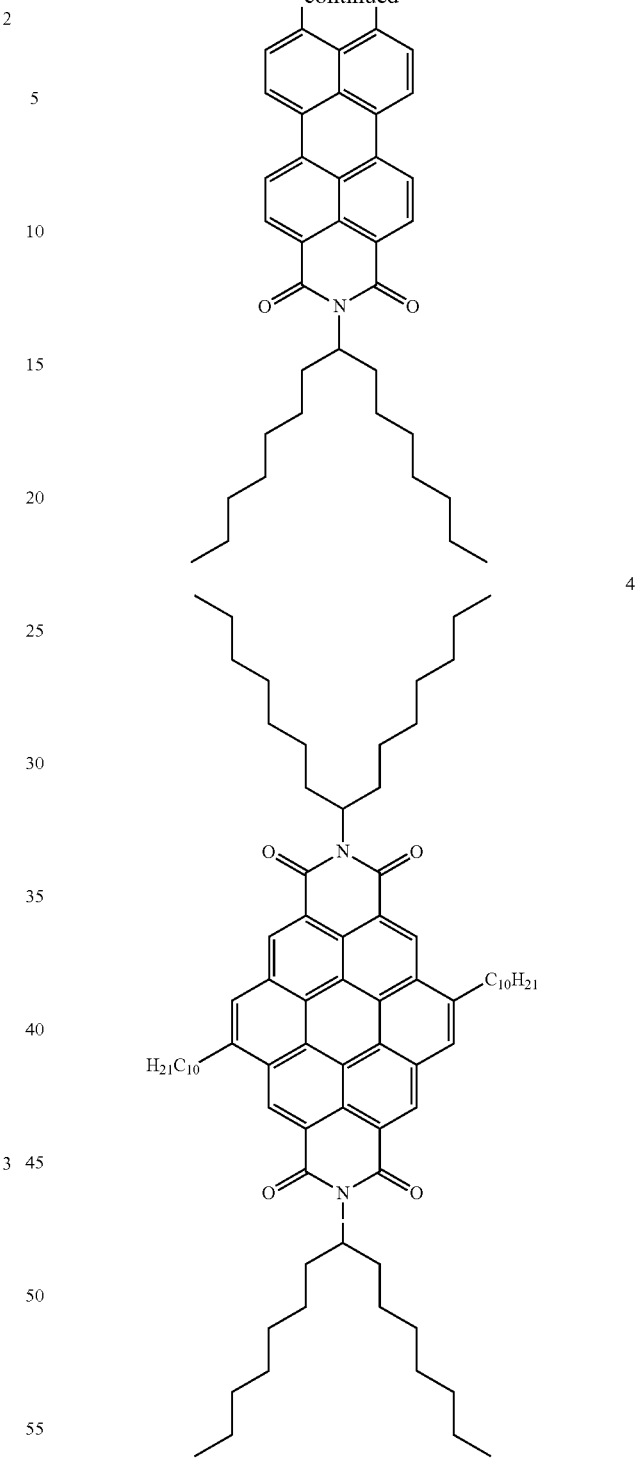
4

The compounds described above are generally thermally stable. FIG. 1 shows the thermal behavior of compounds 1 to 4, determined by means of DSC (differential scanning calorimetry). 1 exhibits a direct transition from the columnar ordered state to the isotropic state at 130° C. The isotropization temperature for 2 is 278° C. and that for 3 is above 500° C. 3 exhibits a further liquid-crystalline state at 188° C. Coronene 4 undergoes a direct transition from the columnar ordered state to the isotropic state at 285° C.

Figure 2:
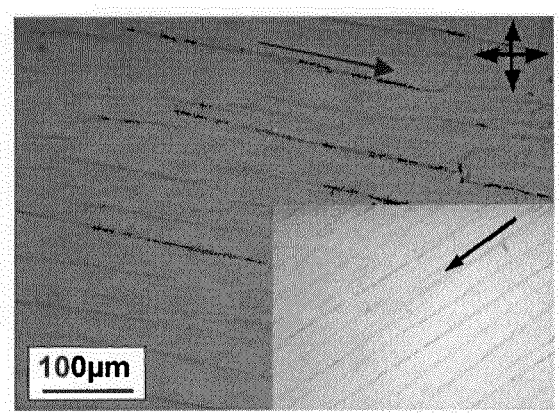
FIG. 2 shows the TDI film under a polarization microscope.
Figure 3:
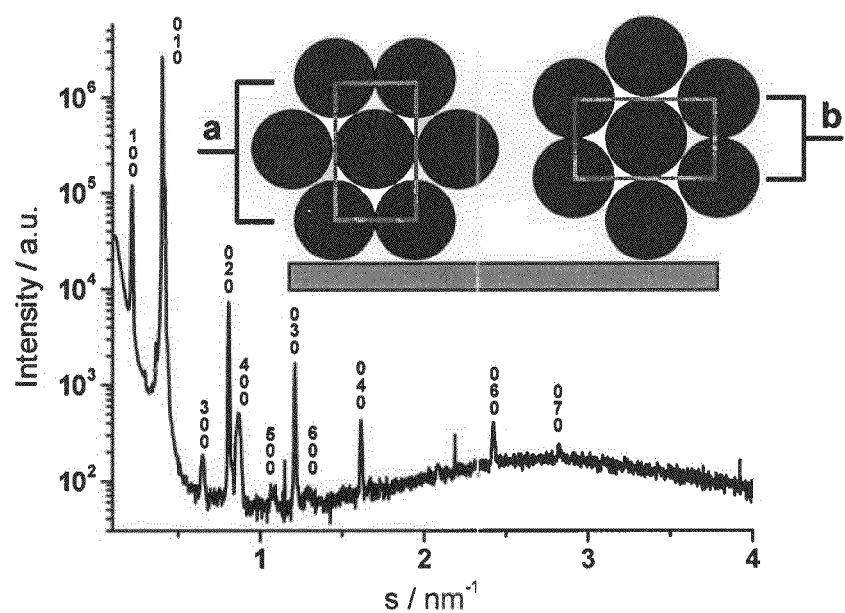
FIG. 3 shows x-ray scattering measurements of the film of TDI 2.
Figure 4:
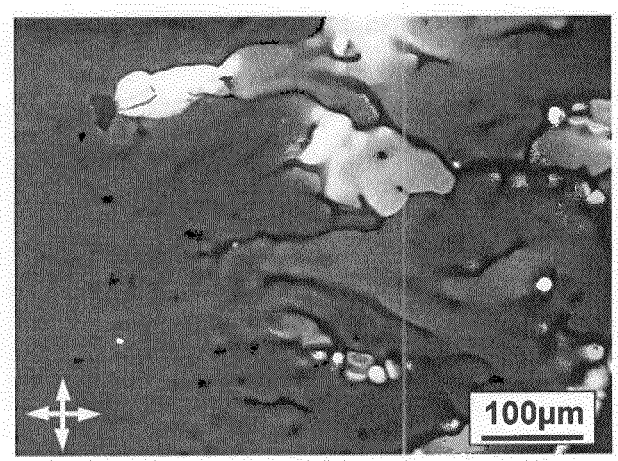
FIG. 4 shows the image of CDI molecules (4) "sandwiched" between two glass plates and cooled from the isotropic phase, under a polarization microscope, which shows negligible birefringence.
Figure 5:
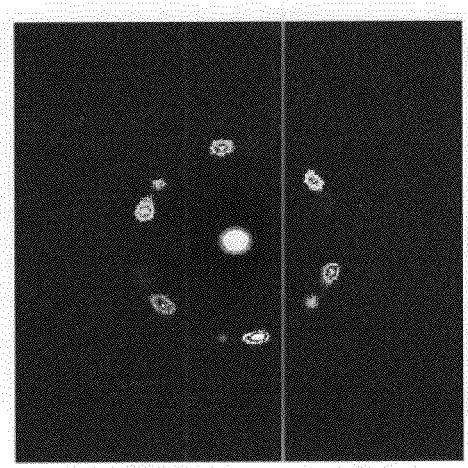
FIG. 5 shows a WAXS wide angle X-ray scattering transmission image of the same.

TDI (2) and PDI (1) were placed between two glass plates and cooled from the isotropic phase. FIG. 2 shows the TDI film under a polarization microscope. TDI exhibits self-organization in large domains with sizes of hundreds of micrometers. The birefringence and the high optical anisotropy indicate a marked uniaxial columnar arrangement with discs aligned edge-on. This arrangement is also confirmed by large area X-ray scattering in reflection. The presence of a large number of sharp reflections in FIG. 3 confirms the high crystallinity of the film of TDI 2. The edge-on arrangement observed here is advantageously suitable for semiconductors in OFETs. The modules can arrange themselves in edge-on alignment on the dielectric and transport charge carriers through the π-planes of the rylene skeletons. CDI molecules (4) were likewise "sandwiched" between two glass plates and cooled from the isotropic phase. FIG. 4 shows the image under a polarization microscope, which shows negligible birefringence. A WAXS wide angle X-ray scattering transmission image (FIG. 5) demonstrates that a hexagonal arrangement of the molecules in the direction of the incident beam is present. The molecules thus self-organize parallel to the surface normal. This face-on alignment is particularly advantageous for use in solar cells, in which the absorber molecules must have semiconductive properties. Absorbers arranged in this way can interact very efficiently with the incident light, and they conduct the charge carriers directly in the direction of the substrates, or electrodes, on which they are arranged.

It can be assumed that appropriate pretreatment of the surfaces, the method of applying the semiconductor to the substrate (from solution or from the melt), allows the two arrangements to be established in a controlled manner and, according to the application in an OFET or in a solar cell, either face-on (homeotropic) or edge-on arrangements to be established. In any case, however, it should be possible to construct good OFETs with the terrylenediimides, perylenediimides and quaterrylenediimides described above, and good solar cells with the coronenes.

Preparation

Variant 1 (Imidation of Rylenetetracarboxylic Dianhydrides):

The preparation of the inventive compounds of the general formula I can proceed from known rylenetetracarboxylic dianhydrides. The rylenecarboximides can be prepared by imidating the correspondingly substituted or unsubstituted anhydrides, provided that they are available. When n=1 (naphthalenetetracarboxylic dianhydrides), they are always unsubstituted, di- to tetrabrominated, di- to tetrafluorinated and di- to tetracyanated and dichlorinated. When n=2 (perylenetetracarboxylic dianhydrides), they are always tetrachlorinated, di- and tetrabrominated and difluorinated.

The invention therefore further provides a process for preparing compounds of the formula I

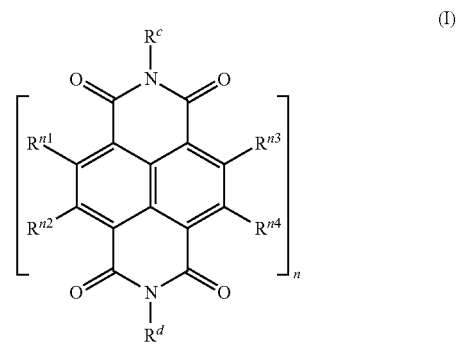

where n is 1 or 2, the $R^{n1}$, $R^{n2}$, $R^{n3}$ and $R^{n4}$ radicals are each independently selected from hydrogen, F, Cl, Br and CN, the $R^c$ and $R^d$ radicals are each independently selected from groups of the formulae II.1 to II.5:

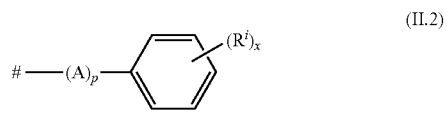

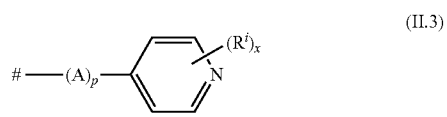

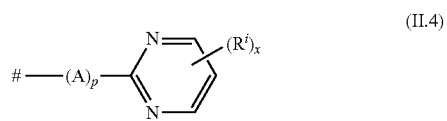

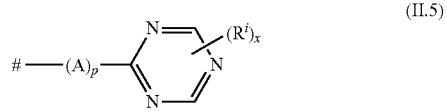

in which represents the bonding site to the imide nitrogen atom, p is 0 or 1, x is 2 or 3, A where present, is a $C_1$-$C_{10}$-alkylene group which may be interrupted by one or more nonadjacent groups which are selected from —O— and —S—, where, in the case that x in the compounds of the formula II.1 is 2, the carbon atom which bears the $R^i$ radicals additionally bears a hydrogen atom, where x in the compounds of the formula II.5 is 2, the $R^i$ radicals are each independently selected from $C_4$-$C_{30}$-alkyl which may be interrupted by one or more nonadjacent oxygen atom(s), in which a1) a rylene dianhydride of the formula Ia

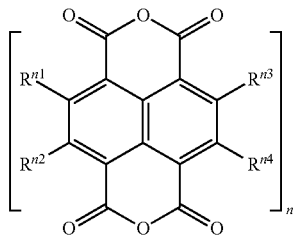

is subjected to a reaction with an amine of the formula $H_2N—R^c$ and if appropriate a different amine of the formula $H_2N—R^d$.

The imidation of carboxylic anhydride groups is known in principle. Preference is given to reacting the dianhydride with the primary amine in the presence of a high-boiling solvent.

Suitable solvents for the imidation are nonpolar aprotic solvents, such as hydrocarbons, for example benzene, toluene, xylene, mesitylene, petroleum ether, decalin, etc. As solvents also polar aprotic solvents such as trialkylamines, nitrogen-containing heterocycles, N,N-disubstituted aliphatic carboxamides (preferably N,N-di($C_1$-$C_4$-alkyl)($C_1$-$C_4$)carboxamides) and N-alkyllactams such as dimethylformamide, diethylformamide, dimethylacetamide, dimethylbutyramide and N-methylpyrrolidone, preference being given to N-methylpyrrolidone.

Examples of particularly suitable solvents are: quinoline, isoquinoline, quinaldine, pyrimidine, N-methylpiperidine and pyridine; dimethylformamide, diethylformamide, dimethylacetamide and dimethylbutyramide; N-methylpyrrolidone. The preferred solvent from this group is quinoline.

Suitable solvents are also protic solvents, especially aliphatic carboxylic acids, preferably $C_2$-$C_{12}$-carboxylic acids, such as acetic acid, propionic acid, butanoic acid and hexanoic acid, acetic acid and propionic acid being preferred protic solvents.

According to the reactivity of the reactants, either the aprotic or the protic solvents are preferred. For instance, the aprotic solvents are preferable for the reaction of unsubstituted rylenecarboxylic anhydrides, while the protic solvents are preferred in the case of reaction of the more reactive substituted rylenecarboxylic anhydrides.

Generally from 1 to 100 ml, especially from 3 to 70 ml, of solvent are used per g of rylenecarboxylic anhydride (Ia).

The reaction can be undertaken in the presence of an imidation catalyst. Suitable imidation catalysts are Lewis and Brønsted acids, for example organic and inorganic acids, e.g. formic acid, acetic acid, propionic acid and phosphoric acid.

The use of a Lewis acid is advisable especially in the case of reaction of the relatively unreactive unsubstituted rylenecarboxylic anhydrides (Ia).

Suitable Lewis acids are in particular zinc, copper and iron salts, and it is also possible to use the oxides in the case of copper. Preference is given to the zinc and copper compounds, particular preference being given to the zinc compounds.

Examples of suitable Lewis acids are zinc acetate, zinc propionate, copper(I) oxide, copper(II) oxide, copper(I) chloride, copper(I) acetate and iron(III) chloride, very particular preference being given to zinc acetate.

When a Lewis acid is used, generally from 0.5 to 3 and preferably from 0.5 to 1.5 equivalents are used per mole of anhydride group to be converted in the rylenecarboxylic anhydride (Ia).

The reaction temperature likewise depends on the reactivity of the reactants and is generally within the range from 50 to 250° C. In the case of the relatively unreactive unsubstituted rylenecarboxylic anhydrides, temperatures of from 150 to 230° C. are preferred; the reaction of the more reactive substituted rylenecarboxylic anhydrides (Ia) is preferably undertaken at from 110 to 170° C.

If desired (obligatory in the case of reaction with diamines), the water of reaction which forms and any water introduced with the assistants can be distilled off during the reaction.

The reaction can be effected under protective gas, for example nitrogen or argon.

An imidation procedure suitable in process technology terms is as follows:

A mixture of rylenecarboxylic anhydride, amine, solvent and if appropriate Lewis acid, if appropriate with distillative removal of the water which forms, is heated to the desired reaction temperature for from 1 to 48 h. When too much solvent is also distilled off in the course of distillative removal of the water, a corresponding further amount has to be added.

The isolation of the resulting compounds can be undertaken as follows:

The desired compounds are precipitated or crystallized out by cooling and addition of a protic solvent, such as water or a lower aliphatic alcohol, for example a $C_1$-$C_4$-alkanol, filtered off, washed with one of the aforementioned solvents and if appropriate a dilute mineral acid to remove residues of rylenedicarboximide derivatives and/or inorganic salts, and dried.

The resulting liquid-crystalline compounds can, if desired, be subjected to a column chromatography or column filtration or to a recrystallization or fractional crystallization for further purification.

Variant 2 (Suzuki Reaction):

Inventive perylene, terrylene and quaterrylene compounds of the general formula I in which the aromatic ring is unsubstituted can also be prepared by Suzuki coupling reaction; preference is given to using this process to prepare terrylene and quaterrylene compounds of the general formula I. A suitable process for preparing terrylenetetracarboximides by Suzuki coupling is described, for example, in WO 2005/070894.

The invention therefore further provides a process for preparing compounds of the formula I

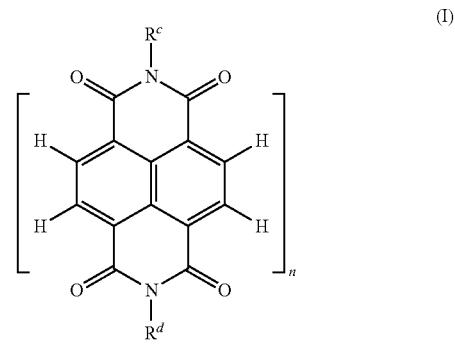

where
n is 2, 3 or 4,
the $R^c$ and $R^d$ radicals are each independently selected from groups of the formulae II.1 to 11.5:

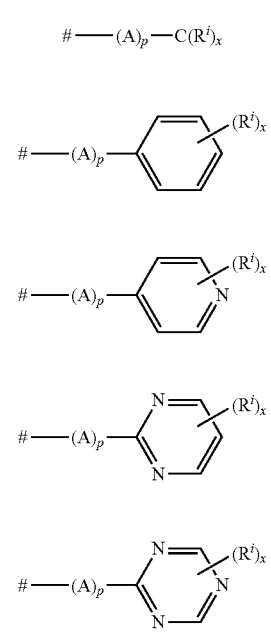

in which
\# represents the bonding site to the imide nitrogen atom,
p is 0 or 1,
x is 2 or 3,
A where present, is a $C_1$-$C_{10}$-alkylene group which may be interrupted by one or more nonadjacent groups which are selected from —O— and —S—,
where, in the case that x in the compounds of the formula II.1 is 2, the carbon atom which bears the $R^i$ radicals additionally bears a hydrogen atom,
where x in the compounds of the formula II.5 is 2,
the $R^i$ radicals are each independently selected from $C_4$-$C_{30}$-alkyl which may be interrupted by one or more nonadjacent oxygen atom(s),
in which
α) a compound of the formula IIIa)

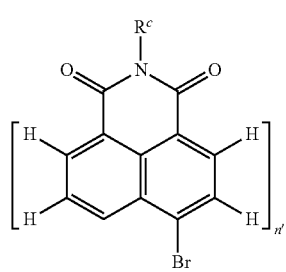

where
n' is 1 or 2, is reacted with a diborane of the formula IV

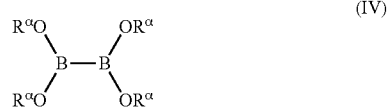

in which
$R^α$ are the same or different and are each independently hydrogen, $C_1$-$C_{30}$-alkyl, $C_5$-$C_8$-cycloalkyl, aryl or hetaryl, where the $R^α$ radicals may also be bonded to one another to form a five-membered ring which comprises the two oxygen atoms and the boron atom and may be substituted on the carbon atoms by up to 4 $C_1$-$C_{30}$-alkyl, $C_5$-$C_s$-cycloalkyl, aryl or hetaryl groups, to obtain a compound of the formula V

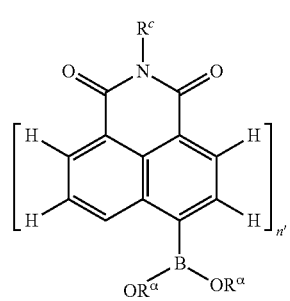

β) the compound of the formula V) to a Suzuki coupling reaction with a compound of the formula IIIb)

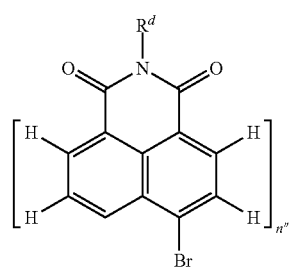

where
n" is 1 or 2,
in the presence of a transition metal catalyst and of a base, to obtain a compound of the formula VI

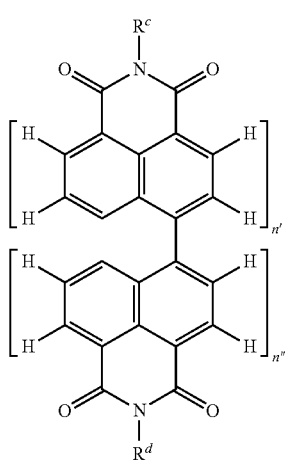

(VI)

γ) the compound of the formula VI) is converted by cyclodehydrogenation in an organic reaction medium which has hydroxyl and amino functions and comprises an essentially undissolved base to a compound of the formula I where n represents the sum of n' and n".

To provide compounds of the formulae IIIa or IIIb, compounds of the formulae

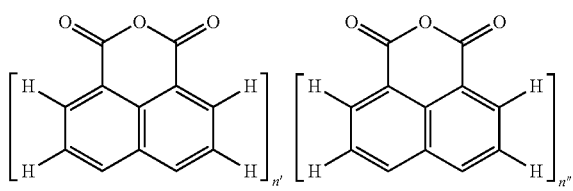

in which n' and n" are independently 1 or 2,
can be subjected to a reaction with an amine of the formula $H_2N—R^c$ or a different amine of the formula $H_2N—R^d$ and to a bromination. The sequence of bromination and imidation is generally not critical. The imidation can be effected under the conditions described above for step a1).

Halogenated compounds of the formulae IIIa or IIIb in which n' and n" are each 1

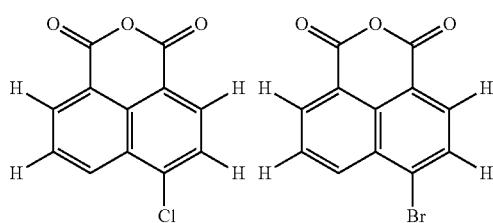

are commercially available.

Perylene monoanhydride is preferably brominated in $H_2SO_4$.

Rylene monoimides are preferably brominated in a carboxylic acid, for example acetic acid, propionic acid or butyric acid. The reaction temperature is preferably from 20 to 100° C., more preferably from 20 to 50° C. Preferably from 1 to 10 molar equivalents, preferably 1 to 5 molar equivalents, of bromine, based on the compounds to be brominated, are used. The reaction is effected, for example, with stirring for from 1 to 24 hours. The amount of carboxylic acid used is preferably from 10 to 100 and preferably from 15 to 50 ml of carboxylic acid per g of rylene derivative. For the bromination, preference is given to adding from 1 to 5% by weight, more preferably from 1 to 2% by weight, of iodine, based on bromine, as a catalyst.

Step α)

The diborane IV is reacted with the reactant IIIa in step α) preferably in the presence of an aprotic organic solvent, of a transition metal catalyst and of a base.

The molar ratio of diborane IV to the reactant IIIa is generally from 0.8:1 to 3:1, especially from 1.5:1 to 2:1.

Suitable solvents for step a) are in principle all aprotic solvents which are stable toward bases under the reaction conditions and have a boiling point above the selected reaction temperature, and in which the reactants IIIa dissolve completely at reaction temperature and the catalysts and bases used at least partially, such that substantially homogeneous reaction conditions are present. It is possible to use either nonpolar aprotic or polar aprotic solvents, preference being given to the nonpolar aprotic solvents.

Examples of preferred nonpolar aprotic solvents are solvents which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or a $C_5$-$C_8$-cycloalkyl radical) and fused aromatics which may be alkyl-substituted and/or partly hydrogenated (especially naphthalene which is substituted by from one to four $C_1$-$C_8$-alkyl groups), and mixtures of these solvents.

Specific examples of particularly preferred solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as can be obtained from the high-boiling, partly or fully hydrogenated fractions from thermal and catalytic cracking processes in crude oil and naphthalene processing, for example mixtures of the Exxsol® type and alkylbenzene mixtures of Solvesso® type.

Very particularly preferred solvents are xylene (all isomers), mesitylene and in particular toluene.

Examples of suitable polar aprotic solvents are N,N-disubstituted aliphatic carboxamides (especially N,N-di-$C_1$-$C_4$-alkyl-$C_1$-$C_4$-carboxamides), nitrogen-containing heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of particularly suitable solvents include: N,N-dimethylformamide, N,N-diethylformamide, N,N-dimethylacetamide and N,N-dimethylbutyramide; N-methyl-2- pyrrolidone, quinoline, isoquinoline, quinaldine, pyrimidine, N-methylpiperidine and pyridine; tetrahydrofuran, dioxane, diphenyl ether, diethylene glycol dimethyl, diethyl, dipropyl, diisopropyl, di-n-butyl, di-sec-butyl and di-tert-butyl-ether, diethylene glycol methyl ethyl ether, triethylene glycol dimethyl and diethyl ether and triethylene glycol methyl ethyl ether.

In the case of perylenes as reactants IIIa, the nonpolar aprotic solvents, in particular toluene, are particularly preferred; in the case of napthalenes as reactants IIIa, polar aprotic solvents, especially dioxane, are particularly preferred.

The amount of solvent is generally from 10 to 1000 ml, preferably from 20 to 300 ml, per g of reactant IIIa.

Suitable transition metal catalysts are especially palladium complexes, such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)-ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, preference being given to [1,1-bis(diphenylphosphino)ferrocene]palladium(II) chloride and tetrakis(triphenylphosphine)palladium(0).

Typically, the transition metal catalyst is used in an amount of from 1 to 20 mol %, in particular from 2 to 10 mol %, based on the reactant IIIa.

The bases used are preferably the alkali metal salts, especially the sodium salts and in particular the potassium salts, of weak organic and inorganic acids, such as sodium acetate, potassium acetate, sodium carbonate, sodium hydrogencarbonate, potassium carbonate and potassium hydrogencarbonate. Preferred bases are the acetates, in particular potassium acetate.

Generally from 1 to 5 mol, preferably from 2 to 4 mol, of base are used per mole of reactant IIIa.

The reaction temperature is typically from 20 to 180° C., in particular from 60 to 120° C.

The reaction time is generally from 0.5 to 30 h, especially from 1 to 20 h.

In terms of process technology, the procedure in step a) is appropriately as follows:

Reactant IIIa and solvent are initially charged, diborane IV, the transition metal catalyst and the base are added in succession and the mixture is heated to the desired reaction temperature under protective gas for from 0.5 to 30 h. After cooling to room temperature, the solid constituents are filtered out of the reaction mixture and the solvent is distilled off under reduced pressure.

The purity of the dioxaborolanyl derivative V thus prepared is generally sufficient for further processing. If appropriate, the crude product can be purified further by washing with a solvent which dissolves the impurities, such as water, or by column chromatography on silica gel with a mixture of methylene chloride and hexane or pentane or with toluene as the eluent.

Step β)

The reaction of the dioxaborolanyl derivative V with a compound IIIb (or if appropriate IIIa) is preferably carried out in the presence of an organic solvent, if desired in a mixture with water.

The molar ratio of V to IIIb is generally from 0.8:1 to 3:1.

In the case of perylenes as reactants IIIb, the molar ratio of V to IIIb is generally from 0.8:1 to 3:1, preferably from 0.9:1 to 2:1.

In the case of naphthalenes as reactants IIIb, the molar ratio of V to IIIb is generally from 0.8:1 to 3:1, preferably from 1.5:1 to 2.5:1.

Suitable solvents for step β) are all solvents in which the dioxaborolanyl derivatives V and the reactants IIIb dissolve completely at reaction temperature and the catalysts and bases used at least partially, such that substantially homogeneous reaction conditions are present. Especially suitable solvents are those already mentioned for step α), preference being given to the alkyl-substituted benzenes here too. The amount of solvent is typically from 10 to 1000 ml, preferably from 20 to 100 ml, per g of dioxaborolanyl derivative V.

Preference is given to using water as an additional solvent in step β). In this case, generally from 10 to 1000 ml, especially from 250 to 500 ml, of water are used per l of organic solvent.

The transition metal catalysts used in step β) are likewise preferably palladium complexes, the same preferences as in step α) applying here. The amount of catalyst used is typically from 1 to 20 mol %, especially from 1.5 to 5 mol %, based on the dioxaborolanyl derivative V.

Preferred bases in step β), as in step α), are the alkali metal salts of weak acids, particular preference being given to the carbonates such as sodium carbonate and in particular potassium carbonate. In general, the amount of base is from 0.1 to 10 mol, especially from 0.2 to 5 mol, per mole of dioxaborolanyl derivative V.

The reaction temperature is generally from 20 to 180° C., preferably from 60 to 120° C. When water is used in step β), it is advisable not to undertake the reaction at temperatures above 100° C., since it would otherwise be necessary to work under pressure.

The reaction has ended typically within from 0.5 to 48 h, especially within from 5 to 20 h.

In process technology terms, the procedure in step β) is appropriately as follows:

Dioxaborolanyl derivative V and reactant IIIb and also solvent are initially charged, transition metal catalyst and the base which is preferably dissolved in water or a water/alcohol mixture are added and the mixture is heated to the desired reaction temperature under protective gas for from 0.5 to 48 h. After cooling to room temperature, the organic phase is removed from the reaction mixture and the solvent is distilled off under reduced pressure.

The purity of the coupling product VI thus prepared is generally sufficient for further processing. If appropriate, the crude product can be purified further by washing with water and if desired a suitable organic solvent, especially a chlorinated aliphatic or aromatic hydrocarbon, or by column chromatography on silica gel with a mixture of methylene chloride and hexane or pentane or with toluene as the eluent.

Step γ)

The cyclodehydrogenation of VI to I is effected as written below:

The cyclodehydrogenation can be undertaken either in an organic reaction medium which has hydroxyl and amino functions and comprises an essentially undissolved base, or in the presence of a base-stable, high-boiling, organic solvent and of an alkali metal or alkaline earth metal base and of a nitrogen-containing auxiliary base.

Preference is given to the first process variant, which is described in detail below.

Suitable organic reaction media are in particular amino alcohols which have from 2 to 20 and preferably from 2 to 10 carbon atoms. The carbon chain of these alcohols may be interrupted by oxygen atoms in ether function. Examples of particularly suitable solvents are ethanolamine, triethanolamine and diethanolamine, preference being given to ethanolamine. It is also possible to use mixtures of alcohols and amines, each of which have a boiling point of at least 70° C. and are liquid at the reaction temperature.

Typically from 1.5 to 150 ml, preferably from 5 to 50 ml, of reaction medium are used per g of coupling product VI.

Suitable bases essentially insoluble in the reaction medium are the alkali metal salts, especially the sodium salts and in particular the potassium salts, of weak organic and preferably of weak inorganic acids, such as formates, acetates, propionates, hydrogencarbonates, and more preferably carbonates, especially sodium carbonate and in particular potassium carbonate.

In general, the amount of base is from 1 to 10 mol, preferably from 2 to 5 mol, per mole of coupling product VI.

The reaction temperature is generally from 40 to 200° C., especially from 80 to 160° C.

The reaction time is typically from 0.5 to 24 h, preferably from 1 to 12 h.

In process technology terms, the procedure in step γ) is appropriately to stir a mixture of coupling product VI, solvent and base at the desired reaction temperature under protective gas for from 0.5 to 24 h, and precipitate the product I formed out of the reaction mixture after cooling to room temperature by adding an alcohol, such as ethanol, or water, filtering it off and washing with water.

The purification of the resulting product I can be undertaken as follows: catalyst residues can be removed by a rapid filtration through silica gel with washing with a halogenated aliphatic hydrocarbon, such as methylene chloride. Residues of unconverted reactants based on perylene and terrylene can be removed by column chromatography on silica gel with methylene chloride as the eluent or by repeated washing with hexane or pentane.

Terrylenes and quaterrylenes can be prepared by Suzuki coupling, for example as summarized in the scheme which follows:

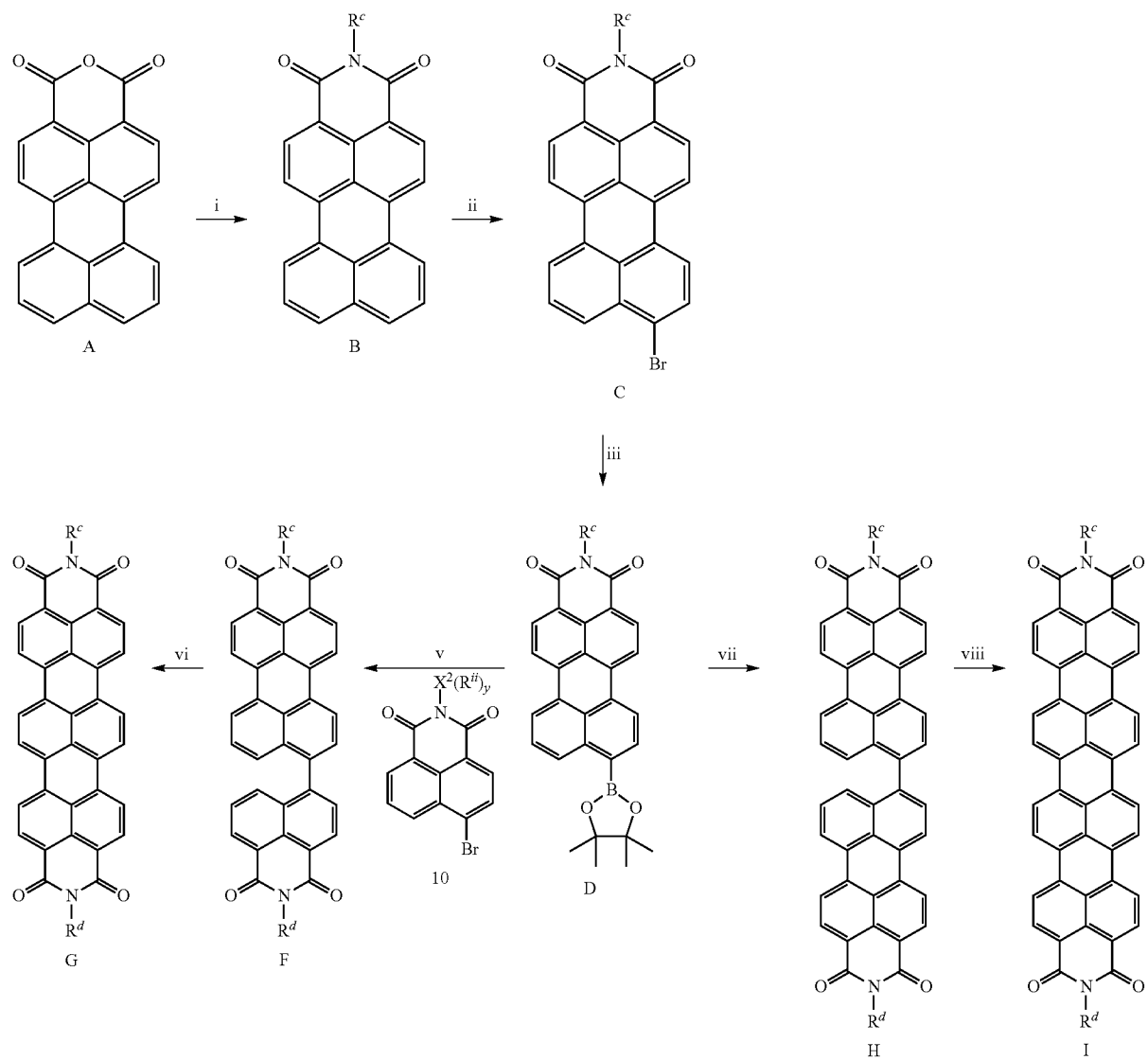

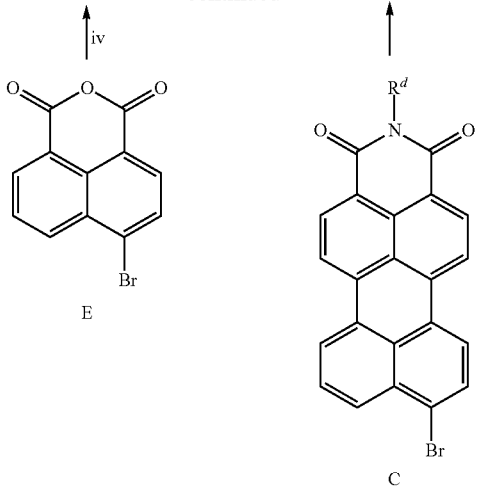

E

C

Variant 3:

Inventive terrylene and quaterrylene compounds of the general formula I can also be prepared by direct synthesis. A suitable process for preparing terrylenetetracarboximides by direct synthesis is described, for example, in WO 2005/070895. A suitable process for preparing quaterrylenetetracarboximides by direct synthesis is described, for example, in WO 2006/021307.

The invention therefore further provides a process for preparing compounds of the formula I

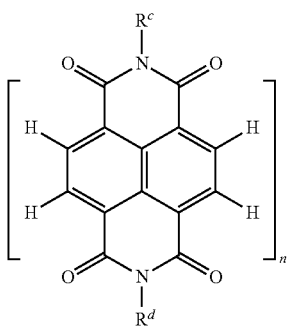
(I)

where n is 3 or 4, the $R^c$ and $R^d$ radicals are each independently selected from groups of the formulae II.1 to II.5:

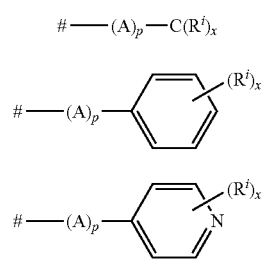

(II.1)

(II.2)

(II.3)

-continued

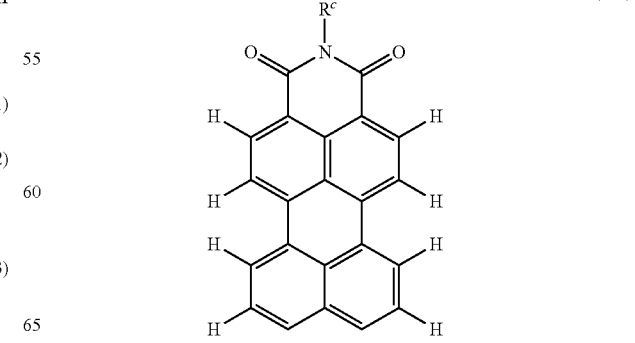

(II.4)

(II.5)

in which represents the bonding site to the imide nitrogen atom, p is 0 or 1, x is 2 or 3, A where present, is a $C_1$-$C_{10}$-alkylene group which may be interrupted by one or more nonadjacent groups which are selected from —O— and —S—, where, in the case that x in the compounds of the formula II.1 is 2, the carbon atom which bears the R radicals additionally bears a hydrogen atom, where x in the compounds of the formula II.5 is 2, the $R^i$ radicals are each independently selected from $C_4$-$C_{30}$-alkyl which may be interrupted by one or more nonadjacent oxygen atom(s), in which a perylene-3,4-dicarboximide of the general formula VII, (VII)

in the presence of a base-stable solvent and of an alkali metal base or alkaline earth metal base, is reacted with a compound of the general formula VIII

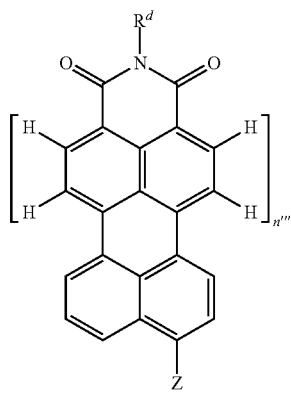

(VIII)

where n''' is 0 or 1 and Z is hydrogen, bromine or chlorine.

The reactants VIII used may be either 4-chlorinated or -brominated (n'''=0) or 9-halogenated (n'''=1) or unhalogenated compounds.

In a first embodiment for the preparation of terrylene derivatives, the reactant VIII used is a 4-chlorinated or -brominated or a 4-unhalogenated naphthalene-1,8-dicarboximide VIII (n'''=0).

When unhalogenated reactants VIII are used, it is generally advisable to undertake the reaction under more severe reaction conditions, i.e. greater excesses of compound VIII and if appropriate, in addition to a strong alkali metal base, a nitrogen-containing auxiliary base and polar aprotic solvent.

Accordingly, the molar ratio of compound VIII to perylene-3,4-dicarboximide VII in the case of use of halogenated reactant VIII (Z: chlorine or bromine) is typically from 4 to 1:1 and preferably from 2 to 1:1, while it is generally from 8 to 1:1 and preferably from 6 to 2:1 in the case of unhalogenated reactant VIII.

Suitable solvents are in principle all solvents stable toward bases under the reaction conditions. Preference is given to aprotic solvents. Preference is further given to solvents having a boiling point above the selected reaction temperature and in which the perylene-3,4-dicarboximide VII and the compounds VIII dissolve fully at reaction temperature and the bases used at least partially, such that substantially homogeneous reaction conditions are present. It is possible to use either nonpolar aprotic or polar aprotic solvents, preference being given to nonpolar aprotic solvents and aprotic solvents based on ethers in the case of use of halogenated reactants VIII, and to the polar aprotic solvents in the case of use of unhalogenated reactants VIII.

Examples of particularly suitable nonpolar aprotic solvents are solvents which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or a $C_5$-$C_8$-cycloalkyl radical) and fused aromatics which may be alkyl-substituted and/or partly hydrogenated (especially naphthalene which is substituted by from one to four $C_1$-$C_6$-alkyl groups), and mixtures of these solvents.

Specific examples of preferred nonpolar aprotic solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene, 1- and 2-ethylnaphthalene; combinations of the aforementioned solvents, as can be obtained from the high-boiling, partly or fully hydrogenated fractions from thermal and catalytic cracking processes in crude oil or naphtha processing, for example mixtures of the Exxsol® type, and alkylbenzene mixtures of the Solvesso® type.

Particularly preferred nonpolar aprotic solvents are xylene (all isomers), mesitylene and in particular toluene and decalin.

Examples of particularly suitable polar aprotic solvents are N,N-disubstituted aliphatic carboxamides (especially N,N-di-$C_1$-$C_4$-alkyl-$C_1$-$C_4$-carboxamides), nitrogen-containing heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of preferred polar aprotic solvents include: N,N-dimethylformamide, N,N-diethylformamide, N,N-dimethylacetamide and N,N-dimethylbutyramide; N-methyl-2-pyrrolidone, quinoline, isoquinoline, quinaldine, pyrimidine, N-methylpiperidine and pyridine; tetrahydrofuran, dioxane, diphenyl ether, diethylene glycol dimethyl, diethyl, dipropyl, diisopropyl, di-n-butyl, di-sec-butyl and di-tert-butyl ether, diethylene glycol methyl ethyl ether, triethylene glycol dimethyl and diethyl ether and triethylene glycol methyl ethyl ether, particular preference being given to diethylene glycol diethyl ether, diphenyl ether and in particular diethylene glycol dimethyl ether.

The amount of solvent is generally from 50 to 250 ml of nonpolar aprotic solvent or from 10 to 50 ml of polar aprotic solvent per g of perylene-3,4-dicarboximide VII.

Suitable bases are strong inorganic and organic alkali metal or alkaline earth metal bases, the alkali metal bases being particularly suitable. Preferred inorganic bases are alkali metal and alkaline earth metal hydroxides and amides; preferred organic bases are alkali metal and alkaline earth metal alkoxides (especially the $C_1$-$C_6$-alkoxides, in particular tert-$C_4$-$C_6$-alkoxides), alkali metal and alkaline earth metal (phenyl)alkylamides (especially the bis($C_1$-$C_4$-alkyl)amides) and triphenylmethylmetallates. Particular preference is given to the alkali metal alkoxides. Preferred alkali metals are lithium, sodium and potassium, very particular preference being given to potassium. Particularly suitable alkaline earth metals are magnesium and calcium.

Specific examples of particularly preferred bases include: lithium hydroxide, sodium hydroxide and potassium hydroxide; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide and potassium tert-butoxide; lithium dimethylamide, lithium diethylamide, lithium diisopropylamide, sodium diisopropylamide, triphenylmethyllithium, triphenylmethylsodium and triphenylmethylpotassium.

Very particularly preferred bases are lithium diisopropylamide, sodium methoxide, sodium tert-butoxide, in particular potassium methoxide and potassium hydroxide and especially potassium tert-butoxide.

In the case of use of the methoxides and of the hydroxides, and generally in the case of use of unhalogenated reactants VIII, it is advisable to increase the reactivity by adding a nitrogen-containing auxiliary base with low nucleophilic action. Suitable bases are alkylamines liquid at the reaction temperatures, especially tri-$C_3$-$C_6$-alkylamines, such as tripropylamine and tributylamine, alkoholamines, especially mono-, di- and tri-$C_2$-$C_4$-alkoholamines, such as mono-, di- and triethanolamine, and especially heterocyclic bases such as pyridine, N-methylpiperidine, N-methylpiperidone, N-methylmorpholine, N-methyl-2-pyrrolidone, pyrimidine, quinoline, isoquinoline, quinaldine and in particular diazabicyclononene (DBN) and diazabicycloundecene (DBU). Suitable use amounts for the auxiliary base are, in the case of the halogenated reactants VIII, generally from 1 to 15 g, preferably from 1 to 5 g, per g of perylene-3,4-dicarboximide VII, and, in the case of the unhalogenated reactants III, generally from 1 to 60 g, preferably from 5 to 20 g, per g of perylene-3,4-dicarboximide II. In the case of halogenated reactants VIII, typically from 2 to 10 mol, especially from 2 to 4 mol, of the alkali metal base are used per mole of perylene-3,4-dicarboximide VII, and, in the case of unhalogenated reactants VIII, generally from 2 to 20 mol, preferably from 8 to 20 mol, per mole of perylene-3,4-dicarboximide VII.

The alkali metal base can be used in solid or in dissolved form. When the alkali metal base is used in combination with a nonpolar aprotic reaction solvent in which it is insufficiently soluble, it can be dissolved in an alcohol which has a higher base strength than the alkali metal base. Suitable alcohols are in particular tertiary aliphatic alcohols which may comprise aryl substituents and have a total of from four to twelve carbon atoms, for example tert-butanol, 2-methyl-2-butanol (tert-amyl alcohol), 3-methyl-3-pentanol, 3-ethyl-3-pentanol, 2-phenyl-2-pentanol, 2,3-di-methyl-3-pentanol, 2,4,4-trimethyl-2-pentanol and 2,2,3,4,4-pentamethyl-3-pentanol.

The reaction temperature is typically from 50 to 210° C., preferably from 70 to 180° C.

Especially in the absence of an auxiliary base, it may be advantageous initially to select a reaction temperature in the upper range in order to deprotonate the perylene-3,4-dicarboximide VII in the 9 position. The subsequent coupling reaction with the reactant VIII can then generally be carried out at lower temperature, which is advisable especially in the case of reactants VIII with base-labile substituents on the imide nitrogen atom.

The reaction time is generally from 1 to 3 h in the case of halogenated reactants VIII and from 2 to 8 h in the case of unhalogenated reactants VIII.

In process technology terms, the procedure in the case of use of unhalogenated reactants VIII is appropriately as follows:

Perylene-3,4-dicarboximide VII, compound VIII and base are initially charged, solvent and if appropriate auxiliary base are added under protective gas and the mixture is heated to the desired reaction temperature with stirring and under protective gas for the desired time. After cooling to room temperature, the compounds I are precipitated by adding a protic solvent which dissolves the other components, for example $C_1$-$C_3$-alcohols and especially water. The precipitate is filtered off and washed with one of the solvents mentioned, especially with one of the alcohols.

In the case of use of halogenated reactants VIII, the procedure may be analogous. However, it is also possible first to heat just a mixture of perylene-3,4-dicarboximide VII, base, if appropriate auxiliary base and solvent to a temperature in the range from 120 to 210° C. with stirring and under protective gas (deprotonation), and then to add the reactant VIII, if appropriate after lowering the temperature to from 50 to 120° C.

For further purification, the products I can be recrystallized, for example, from a mixture of halogenated solvents, such as chloroform and methylene chloride, and alcohols such as methanol, ethanol and isopropanol. Alternatively, it is also possible to undertake column chromatography on silica gel using methylene chloride or acetone as the eluent.

With the aid of the third variant of the process according to the invention using a 4-chlorinated or -brominated or a 4-unhalogenated naphthalene-1,8-dicarboximide VIII (n'''=0), it is possible to prepare terrylene-3,4:11,12-tetracarboximides I in good yields (generally from 40 to 80%) and high purities (typically from 95 to 99%) in one step in an economically viable manner. Compounds I substituted either symmetrically or unsymmetrically on the imide nitrogen atoms are obtainable in an advantageous manner.

In a second embodiment for preparing quaterrylene derivatives, the reactant VIII used is a 9-chlorinated or 9-brominated or a 9-unhalogenated perylene-3,4-dicarboximide VIII (n'''=1).

With the aid of the process according to the invention, the quaterrylene-3,4:13,14-tetracarboximides I can be prepared in one step by reacting a perylene-3,4-dicarboximide VIII (referred to hereinafter as imide VIII) with a perylene-3,4-dicarboximide VII (referred to hereinafter as imide VII) in the presence of a base-stable, high-boiling, organic solvent and of an alkali metal or alkaline earth metal base.

The imide VIII used may be either a 9-halogenated, i.e. 9-chlorinated or more particularly -brominated, or a 9-unhalogenated imide which may bear, on the imide nitrogen atom, an $X^1(R^i)_x$ radical which corresponds to the $X^2(R^{ii})_y$ radical on the imide nitrogen atom of the imide VII or is different therefrom.

The use of halogenated imide VIII enables the controlled synthesis of unsymmetric quaterrylene-3,4:13,14-tetracarboximides I (R≠R'). In this case, it is advantageous to use a molar ratio of VIII to VII of from 4 to 1:1, especially from 2 to 1:1.

When unhalogenated imide VIII is used, it is generally advisable to undertake the conversion under more severe reaction conditions, i.e. to use a nitrogen-containing auxiliary base in addition to a strong alkali metal base.

Suitable solvents are in principle all high-boiling solvents (boiling point >100° C. and above the selected reaction temperature) which are stable toward bases under the reaction conditions and in which the bases used dissolve completely at reaction temperature and the imides VII and VIII at least partially, preferably fully, such that substantially homogeneous reaction conditions are present. It is possible to use either aprotic (nonpolar aprotic and polar aprotic) or protic solvents. It will be appreciated that it is also possible to use solvent mixtures.

Examples of suitable nonpolar aprotic solvents are hydrocarbons which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or a $C_5$-$C_8$-cycloalkyl radial) and fused aromatics which may be alkyl-substituted and/or partly hydrogenated (especially naphthalene which is substituted by from one to four $C_1$-$C_6$-alkyl groups), and mixtures of these solvents.

Specific examples of preferred nonpolar aprotic solvents include:

octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane;

toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene, 1- and 2-ethylnaphthalene; combinations of the aforementioned solvents, as can be obtained from the high-boiling, partly or fully hydrogenated fractions from thermal and catalytic cracking processes in crude oil or naphtha processing, for example mixtures of the Exxsol® type, and alkylbenzene mixtures of the Solvesso® type.

Particularly preferred nonpolar aprotic solvents are xylene (all isomers), mesitylene and in particular decalin.

Examples of suitable polar aprotic solvents are nitrogen-containing heterocycles and aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers).

Specific examples of preferred polar aprotic solvents include:

quinoline, isoquinoline, quinaldine, pyrimidine, N-methylpiperidine and pyridine;

dimethyl- and tetramethyltetrahydrofuran and dioxane;

diphenyl ether; ethylene glycol diethyl, dipropyl, diisopropyl, di-n-butyl, di-sec-butyl and di-tert-butyl ether and ethylene glycol methyl ethyl ether, di- and triethylene glycol dimethyl, diethyl, dipropyl, diisopropyl, di-n-butyl, di-sec-butyl and di-tert-butyl ether and di- and triethylene glycol methyl ethyl ether.

Particular preference is given to diethylene glycol diethyl ether, diphenyl ether and in particular to diethylene glycol dimethyl ether.

Examples of suitable protic solvents are monohydric and polyhydric, aliphatic and aromatic alcohols which boil at >100° C. (especially monohydric $C_4$-$C_{18}$-alkanols, polyhydric $C_2$-$C_4$-alcohols and oligomers thereof, such as $C_2$-$C_3$-alkylene glycols which may comprise up to 6 alkylene oxide units, and phenols), ether alcohols (especially mono-$C_1$-$C_6$-alkyl and monophenyl ethers of monomeric and oligomeric $C_2$-$C_3$-alkylene glycols which may comprise up to 6 alkylene oxide units, in particular ethylene glycol mono-$C_4$-$C_6$-alkyl ethers) and amino alcohols (especially mono-, di- and tri-$C_2$-$C_4$-alcoholamines).

Specific examples of preferred protic solvents include:

n-butanol, isobutanol, tert-butanol, n-pentanol, isopentanol, 2-methylbutanol, 2-methyl-2-butanol (tert-amyl alcohol), hexanol, 2-methylpentanol, 3-methyl-3-pentanol, heptanol, 1-ethylpentanol, 3-ethyl-3-pentanol, 2,3-dimethyl-3-pentanol, octanol, 2-ethylhexanol, 2,4,4-trimethyl-2-pentanol, isooctyl alcohol, nonanol, isononyl alcohol, decanol, 2,2,3,4,4-pentamethyl-3-pentanol, isodecyl alcohol, undecanol, dodecanol, tridecanol, isotridecyl alcohol, tetradecanol, pentadecanol, hexadecanol, heptadecanol and octadecanol;

ethylene glycol, diethylene glycol, triethylene glycol, tetraethylene glycol, pentaethylene glycol and hexaethylene glycol, propylene glycol, 1,3-propanediol, glycerol and 1,2-, 1,3- and 1,4-butanediol;

ethylene glycol monomethyl, monoethyl, monopropyl, monoisopropyl, mono-n-butyl, mono-sec-butyl, mono-tert-butyl, mono-n-pentyl and mono-n-hexyl ether and ethylene glycol monophenyl ether and di- and triethylene glycol monomethyl, monoethyl, monopropyl, monoisopropyl, mono-n-butyl, mono-sec-butyl, mono-tert-butyl, mono-n-pentyl and mono-n-hexyl ether, and di- and triethylene glycol monophenyl ether;

monoethanolamine, diethanolamine and triethanolamine.

Particularly preferred protic solvents are ethylene glycol and ethanolamine.

The amount of solvent is generally from 1 to 20 g, preferably from 2 to 10 g and more preferably from 2 to 5 g per g of imide VII and VIII.

Suitable bases are strong inorganic and organic alkali metal or alkaline earth metal bases, the alkali metal bases being particularly suitable. Preferred inorganic bases are the alkali metal and alkaline earth metal hydroxides and amides; preferred organic bases are alkali metal and alkaline earth metal alkoxides (especially the $C_1$-$C_{10}$-alkoxides, in particular tert-$C_4$-$C_{10}$-alkoxides), alkali metal and alkaline earth metal (phenyl)alkylamides (especially the bis($C_1$-$C_4$-alkyl)amides) and triphenylmethylmetallates. Particular preference is given to the alkali metal alkoxides. Preferred alkali metals are lithium, sodium and potassium, very particular preference being given to potassium. Particularly suitable alkaline earth metals are magnesium and calcium.

Specific examples of particularly preferred bases include: lithium hydroxide, sodium hydroxide and potassium hydroxide; lithium amide, sodium amide and potassium amide; lithium methoxide, sodium methoxide, potassium methoxide, lithium ethoxide, sodium ethoxide, potassium ethoxide, sodium isopropoxide, potassium isopropoxide, sodium tert-butoxide and potassium tert-butoxide; lithium (1,1-dimethyl)octoxide, sodium (1,1-dimethyl)octoxide, potassium (1,1-dimethyl)octoxide, lithium dimethylamide, lithium diethylamide, lithium diisopropylamide, sodium diisopropylamide, triphenylmethyllithium, triphenylmethylsodium and triphenylmethylpotassium.

Very particularly preferred bases are lithium diisopropylamide, sodium methoxide, sodium tert-butoxide, in particular potassium methoxide and potassium hydroxide and especially potassium tert-butoxide.

In the case of use of the methoxides and of the hydroxides and generally in the case of use of unhalogenated imides VIII, it is advisable to increase the reactivity by adding a nitrogen-containing auxiliary base with low nucleophilic action if a nitrogen-containing heterocycle or an alcoholamine is not already present as a solvent. Suitable bases are alkylamines liquid at the reaction temperatures, especially tri-$C_3$-$C_6$-alkylamines, such as tripropylamine and tributylamine, alcoholamines, especially mono-, di- and tri-$C_2$-$C_4$-alcoholamines, such as mono-, di- and triethanolamine, and especially heterocyclic bases, such as pyridine, N-methylpiperidine, N-methylpiperidone, N-methylmorpholine, N-methyl-2-pyrrolidone, pyrimidine, quinoline, isoquinoline, quinaldine and in particular diazabicyclononene (DBN) and diazabicycloundecene (DBU).

Suitable use amounts for the auxiliary base are generally from 0.5 to 25 g, preferably from 1 to 10 g, more preferably from 1 to 3 g, per g of imide VII and VIII.

The alkali metal or alkaline earth metal base is generally used in amounts of from 2 to 20 mol, especially from 2 to 10 mol, per mole of imide VII and VIII.

The alkali metal base can be used in solid or in dissolved form. When the alkali metal base is used in combination with a nonpolar aprotic reaction solvent in which it is insufficiently soluble, it can be dissolved in an alcohol which has a higher base strength than the alkali metal base. Suitable alcohols are in particular tertiary aliphatic alcohols which may comprise aryl substituents and have a total of from four to twelve carbon atoms, for example tert-butanol, 2-methyl-2-butanol (tert-amyl alcohol), 3-methyl-3-pentanol, 3-ethyl-3-pentanol, 2-phenyl-2-pentanol, 2,3-di-methyl-3-pentanol, 2,4,4-trimethyl-2-pentanol and 2,2,3,4,4-pentamethyl-3-pentanol.

The reaction temperature is typically from 70 to 210° C., preferably from 120 to 180° C.

Especially in the absence of an auxiliary base, it may be advantageous for the preparation of unsymmetric quaterrylene-3,4:13,14-tetracarboximides to initially select a reaction temperature in the upper range in order to deprotonate the imide VII in the 9 position. The subsequent coupling reaction with the halogenated imide VIII can then generally be carried out at lower temperature, which is advisable especially in the presence of base-labile substituents (e.g. cyclohexyl) on the imide nitrogen atom.

The reaction time is generally from 1 to 3 h in the case of use of halogenated imides VIII and from 2 to 12 h in the case of use of unhalogenated imides VIII.

In process technology terms, the procedure in the case of use of unhalogenated imides VIII, i.e. more particularly that of a homocondensation, is appropriately as follows:

Solvent, base and if appropriate auxiliary base are heated under protective gas for homogenization, and imide VII and imide VIII are added under protective gas, if appropriate after preceding cooling, and the mixture is heated to the desired reaction temperature with stirring and under protective gas for the desired time. After cooling to room temperature, the quaterrylene-3,4:13,14-tetracarboximides I are precipitated by adding a protic solvent which dissolves the other components, for example $C_1$-$C_6$-alcohols or water. The precipitate is filtered off and washed with one of the solvents mentioned, especially with one of the alcohols.

In the case of use of halogenated imides VIII, the procedure in process technology terms may be as in the case of use of unhalogenated imides VIII. However, it is also possible first to heat just a mixture of imide VII, base, if appropriate auxiliary base and solvent to a temperature in the range from 120 to 210° C. with stirring and under protective gas (deprotonation) and then to add the imide VIII, if appropriate after lowering the temperature to from 50 to 120° C.

Occasionally, it may be appropriate to subject the reaction product to an oxidation. The simplest way of doing this is by blowing atmospheric oxygen into the still-warm reaction mixture. However, it is also possible to add oxidizing agent, preferably hydrogen peroxide, but also sugars containing aldehyde groups, for example glucose, especially after the reaction.

The invention further provides a process for preparing compounds of the formula I

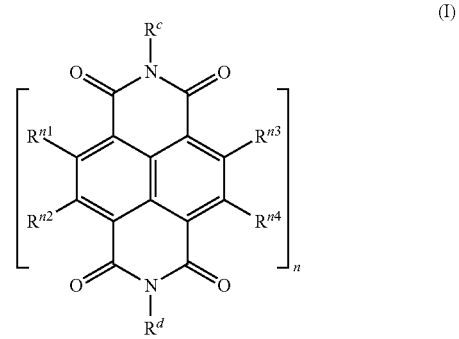

where
n is 1 or 2,
at least one of the $R^{n1}$, $R^{n2}$, $R^{n3}$ and $R^{n4}$ radicals is CN and the $R^{n1}$, $R^{n2}$, $R^{n3}$ and $R^{n4}$ radicals which are not CN are each hydrogen,
the $R^a$ and $R^b$ radicals are each independently selected from hydrogen and alkyl,
the $R^c$ and $R^d$ radicals are each independently selected from groups of the formulae II.1 to II.5:

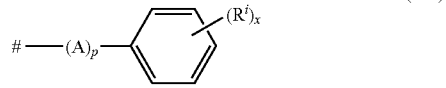

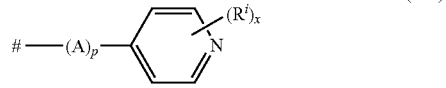

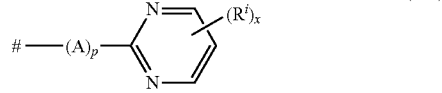

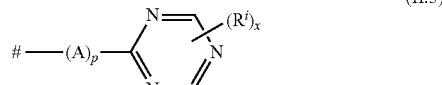

in which
represents the bonding site to the imide nitrogen atom,
p is 0 or 1,
x is 2 or 3,
A where present, is a $C_1$-$C_{10}$-alkylene group which may be interrupted by one or more nonadjacent groups which are selected from —O— and —S—,
where, in the case that x in the compounds of the formula II.1 is 2, the carbon atom which bears the $R^i$ radicals additionally bears a hydrogen atom,
where x in the compounds of the formula II.5 is 2,
the $R^i$ radicals are each independently selected from $C_4$-$C_{30}$-alkyl which may be interrupted by one or more nonadjacent oxygen atom(s), where at least one of the $R^i$ radicals in the compounds of the formula II.1 may also be $C_4$-$C_{30}$-alkyloxy or $C_4$-$C_{30}$-alkylthio,
in which a compound of the formula I in which at least one of the $R^{n1}$, $R^{n2}$, $R^{n3}$ and $R^{n4}$ radicals is Br or Cl, and the $R^{n1}$, $R^{n2}$, $R^{n3}$ and $R^{n4}$ radicals which are not Br or Cl are each hydrogen, is subjected to a substitution of the bromine or of the chlorine for cyano groups in an aromatic hydrocarbon as a solvent.

Suitable compounds for the halogen exchange are alkali metal cyanides, such as KCN and NaCN, and especially zinc cyanide. The reaction is effected preferably in the presence of at least one transition metal catalyst. Suitable transition metal catalysts are especially palladium complexes such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, preference being given to [1,1'-bis(diphenylphosphino)ferrocene]palladium(II) chloride and tetrakis(triphenylphosphine)palladium(0).

It has been found that, surprisingly, the reaction proceeds particularly efficiently in aromatic hydrocarbons as solvents. These preferably include benzene, toluene, xylenes, etc. Particular preference is given to using toluene.

For further purification, the products I can be recrystallized, for example, from a mixture of halogenated solvents, such as chloroform and methylene chloride, and alcohols such as methanol, ethanol and isopropanol. Alternatively, it is also possible to undertake column chromatography on silica gel using methylene chloride or acetone as the eluent.

A further purification method consists in recrystallizing the products I from N, N-disubstituted aliphatic carboxamides, such as N,N-dimethylformamide and N,N-dimethylacetamide, or nitrogen-containing heterocycles such as N-methylpyrrolidone, or mixtures thereof with alcohols, such as methanol, ethanol and isopropanol, or in washing them with these solvents.

Finally, the products I can also be fractionated from sulfuric acid.

With the aid of the process according to the invention, the quaterrylene-3,4:13,14-tetracarboximides I can be prepared in good yields (generally from 30 to 60%) and high purities (typically from 90 to 99%) in one step in an economically viable manner. Quaterrylene-3,4:13,14-tetracarboximides I substituted both symmetrically and unsymmetrically on the imide nitrogen atoms are obtainable in an advantageous manner.

Coronenes of the general formula II in which $R^a$ and $R^b$ are each alkyl are known in principle (Müllen, J. Mater. Chem., 11, 1789 (2001)).

The inventive compounds and those obtainable by the process according to the invention are particularly advantageously suitable as organic semiconductors. They function as n-semiconductors and are notable for their air stability. They also possess a high charge transport mobility and have a high on/off ratio. They are suitable in a particularly advantageous manner for organic field-effect transistors. The inventive compounds are advantageously suitable for producing integrated circuits (ICs) for which the n-channel MOSFETs (metal oxide semiconductor field-effect transistors) customary to date are used. These are CMOS-like semiconductor units, for example for microprocessors, microcontrollers, static RAM and other digital logic circuits. For the production of semiconductor materials, the processes according to the invention can be processed further by one of the following processes: printing (offset, flexographic, gravure, screen, inkjet, electrophotography), evaporation, laser transfer, photolithography, drop-casting. They are suitable in particular for use in displays and RFID tags.

In a suitable embodiment, the deposition of a compound of the general formulae I and II which is convertible to the gas phase is carried out by a gas phase deposition process (physical vapor deposition, PVD). PVD processes are performed under high-vacuum conditions and comprise the following steps: evaporation, transport, deposition.

The resulting semiconductor layers generally have a thickness which is sufficient for ohmic contact between source and drain electrodes. The deposition can be effected under an inert atmosphere, for example under nitrogen, argon or helium. The deposition is effected typically at ambient pressure or under reduced pressure. A suitable pressure range is from about $10^{-7}$ to 1.5 bar. The compound of the formula I or II is preferably deposited on the substrate in a thickness of from 10 to 1000 nm, more preferably from 15 to 250 nm. In a specific embodiment, the compound of the formula I or II is deposited at least partly in crystalline form.

In a preferred embodiment, the deposition of at least one compound of the general formula I or II (and if appropriate further semiconductor materials) is therefore effected by a wet deposition method (wet processing). This includes, for example, spin-coating and drop-casting. The wet processible compounds of the formulae (I) and (II) should thus also be suitable for producing semiconductor elements, especially OFETs or based on OFETs, by a printing process. It is possible for this purpose to use customary printing processes (inkjet, flexographic, offset, gravure; intaglio printing, nanoprinting). Preferred solvents for the use of the compounds of the formulae (I) and (II) in a printing process are aromatic solvents such as toluene, xylene, etc. It is also possible to add thickening substances such as polymers, for example polystyrene, etc., to these "semiconductor inks". In this case, the dielectrics used are the aforementioned compounds.

Organic solar cells based on the inventive compounds of the formulae (I) and (II) and those used in accordance with the invention generally have a layer structure and generally comprise at least the following layers: anode, photoactive layer and cathode. These layers generally consist of a substrate customary therefor. Suitable substrates are, for example, oxidic materials (such as glass, quartz, ceramic, $SiO_2$, etc.), polymers (e.g. polyvinyl chloride, polyolefins such as polyethylene and polypropylene, polyesters, fluoropolymers, polyamides, polyurethanes, polyalkyl (meth)acrylates, polystyrene and mixtures and composites thereof) and combinations thereof.

Suitable electrodes (cathode, anode) are in principle metals (preferably of groups 8, 9, 10 or 11 of the Periodic Table, e.g. Pt, Au, Ag, Cu, Al, In, Mg, Ca), semiconductors (e.g. doped Si, doped Ge, indium tin oxide (ITO), gallium indium tin oxide (GITO), zinc indium tin oxide (ZITO), etc.), metal alloys (e.g. based on Pt, Au, Ag, Cu, etc., especially Mg/Ag alloys), semiconductor alloys, etc. The anode used is preferably a material essentially transparent to incident light. This includes, for example, ITO, doped ITO, ZnO, $TiO_2$, Ag, Au, Pt. The cathode used is preferably a material which essentially reflects the incident light. This includes, for example, metal films, for example of Al, Ag, Au, In, Mg, Mg/Al, Ca, etc.

For its part, the photoactive layer comprises at least one or consists of at least one layer which comprises, as an organic semiconductor material, at least one compound which is selected from compounds of the formulae I and II as defined above. In general, the photoactive layer comprises at least one layer which comprises an organic acceptor material (electron transport layer, ETL) and at least one layer which comprises an organic donor material (hole transport layer, HTL). These two layers may be completely or partly mixed. In addition to the photoactive layer, there may be one or more further layers, for example ETL, HTL (which need not absorb), blocking layers (e.g. exciton-blocking layers, EBLs) (which should not absorb), multiplication layers.

The structure of organic solar cells is described, for example, in US 2005/0098726 A1 and US 2005/0224905 A1, which are fully incorporated here by reference.

The compounds of the formulae (I) and (II) are particularly advantageously suitable for use in organic photovoltaics (OPVs). Preference is given to their use in solar cells which are characterized by diffusion of excited states (exciton diffusion). In this case, one or both of the semiconductor materials utilized is notable for a diffusion of excited states. Also suitable is the combination of at least one semiconductor material which is characterized by diffusion of excited states with polymers which permit conduction of the excited states along the polymer chain. In the context of the invention, such solar cells are referred to as excitonic solar cells. The direct conversion of solar energy to electrical energy in solar cells is based on the internal photo effect of a semiconductor material, i.e. the generation of electron-hole pairs by absorption of photons and the separation of the negative and positive charge carriers at a p-n transition or a Schottky contact. An exciton can form, for example, when a photon penetrates into a semiconductor and excites an electron to transfer from the valence band into the conduction band. In order to generate current, the excited state generated by the absorbed photons must, however, reach a p-n transition in order to generate a hole and an electron which then flows to the anode and cathode. The photovoltage thus generated can bring about a photocurrent in an external circuit, through which the solar cell delivers its power. The semiconductor can absorb only those photons which have an energy which is greater than its band gap. The size of the semiconductor band gap thus determines the proportion of sunlight which can be converted to electrical energy. The excitonic solar cells described consist normally of two absorbing materials with different band gaps in order to very effectively utilize the solar energy. Most organic semiconductors have exciton diffusion lengths of up to 10 nm. There is still a need here for organic semiconductors through which the excited state can be passed on over very large distances. It has now been found that, surprisingly, the compounds of the general formula I described above are particularly advantageously suitable for use in excitonic solar cells.

Suitable organic solar cells generally have a layer structure and generally comprise at least the following layers: anode, photoactive layer and cathode. These layers are generally present on a substrate customary therefor. The structure of organic solar cells is described, for example, in US 2005/0098726 A1 and US 2005/0224905 A1, which are fully incorporated here by reference.

For its part, the photoactive layer comprises at least one or consists of at least one layer which comprises, as an organic semiconductor material, at least one compound which is selected from compounds of the formulae I and II as defined above. In one embodiment, the photoactive layer comprises at least one organic acceptor material. In addition to the photoactive layer, there may be one or more further layers, for example a layer with electron-conducting properties (ETL, electron transport layer) and a layer which comprises a hole-conducting material (hole transport layer, HTL) which need not absorb, exciton- and hole-blocking layers (e.g. EBLs) which should not absorb, multiplication layers. Suitable exciton- and hole-blocking layers are described, for example, in U.S. Pat. No. 6,451,415.

Suitable exciton blocker layers are, for example, bathocuproins (BCPs), 4,4',4"-tris(N-(3-methylphenyl)-N-phenylamino)triphenylamine (m-MTDATA) or polyethylenedioxythiophene (PEDOT), as described in U.S. Pat. No. 7,026,041.

The inventive excitonic solar cells are based on photoactive donor-acceptor heterojunctions. When at least one compound of the formula (I) is used as the HTM, the corresponding ETM must be selected such that, after excitation of the compounds, a rapid electron transfer to the ETM takes place. Suitable ETMs are, for example, C60 and other fullerenes, perylene-3,4:9,10-bis(dicarboximides), PTCDIs, etc. When at least one compound of the formula (I) is used as the ETM, the complementary HTM must be selected such that, after excitation of the compound, a rapid hole transfer to the HTM takes place. The heterojunction may have a flat configuration (cf. Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).) or be implemented as a bulk heterojunction (or interpenetrating donor-acceptor network; cf., for example, C. J. Brabec, N. S. Sariciftci, J. C. Hummelen, Adv. Funct. Mater., 11 (1), 15 (2001).). The photoactive layer based on a heterojunction between at least one compound of the formula (I) and an HTL or ETL can be used in solar cells with MiM, pin, pn, Mip or Min structure (M=metal, p=p-doped organic or inorganic semiconductor, n=n-doped organic or inorganic semiconductor, i=intrinsically conductive system of organic layers; cf., for example, J. Drechsel et al., Org. Eletron., 5 (4), 175 (2004) or Maennig et al., Appl. Phys. A 79, 1-14 (2004)). It can also be used in tandem cells, as described by P. Peumnas, A. Yakimov, S. R. Forrest in J. Appl. Phys, 93 (7), 3693-3723 (2003) (cf. patents U.S. Pat. Nos. 4,461,922, 6,198,091 and 6,198,092). It can also be used in tandem cells composed of two or more MiM, pin, Mip or Min diodes stacked on one another (cf. patent application DE 103 13 232.5) (J. Drechsel et al., Thin Solid Films, 451-452, 515-517 (2004)).

Thin layers of the compounds and of all other layers can be produced by vapor deposition under reduced pressure or in inert gas atmosphere, by laser ablation or by solution- or dispersion-processible methods such as spin-coating, knife-coating, casting methods, spraying, dip-coating or printing (e.g. inkjet, flexographic, offset, gravure; intaglio, nanoimprinting). The layer thicknesses of the M, n, i and p layers are typically from 10 to 1000 nm, preferably from 10 to 400 nm.

The substrates used are, for example, glass, metal foils or polymer films which are generally coated with a transparent conductive layer (for example $SnO_2$:F, $SnO_2$:In, ZnO:Al, carbon nanotubes, thin metal layers).

In addition to the compounds of the general formulae (I) and (II), the following semiconductor materials are suitable for use in organic photovoltaics:

acenes such as anthracene, tetracene, pentacene, each of which may be substituted or unsubstituted. Substituted acenes preferably comprise at least one substituent selected from electron-donating substituents (e.g. alkyl, alkoxy, ester, carboxylate or thioalkoxy), electron-withdrawing substituents (e.g. halogen, nitro or cyano) and combinations thereof. These include 2,9-dialkylpentacenes and 2,10-dialkyl-pentacenes, 2,10-dialkoxypentacenes, 1,4,8,11-tetraalkoxypentacenes and rubrene (5,6,11,12-tetraphenylnaphthacene). Suitable substituted pentacenes are described in US 2003/0100779 and U.S. Pat. No. 6,864,396, which are incorporated here by reference. A preferred acene is rubrene (5,6,11,12-tetraphenylnaphthacene);

phthalocyanines, for example phthalocyanines which bear at least one halogen substituent, such as hexadecachlorophthalocyanines and hexadecafluorophthalo-cyanines, metal-free phthalocyanines or phthalocyanines comprising divalent metals or metal atom-containing groups, especially those of titanyloxy, vanadyloxy, iron, copper, zinc, etc. Suitable phthalocyanines are especially copper phthalocyanine, zinc phthalocyanine, metal-free phthalocyanine, copper hexadecachlorophthalocyanine, zinc hexadecachlorophthalocyanine, metal-free hexadecachlorophthalocyanine, copper hexadecafluorophthalocyanine, hexadecafluorophthalocyanine or metal-free hexadecafluorophthalocyanine;

porphyrins, for example 5,10,15,20-tetra(3-pyridyl)porphyrin (TpyP);

liquid-crystalline (LC) materials, for example coronenes such as hexabenzocoronene (HBC-PhC12), coronenediimides, or triphenylenes such as 2,3,6,7,10,11-hexahexylthiotriphenylene (HTT6), 2,3,6,7,10,11-hexakis(4-n-nonylphenyl)triphenylene (PTP9) or 2,3,6,7,10,11-hexakis (undecyloxy)triphenylene (HAT11). Particular preference is given to liquid-crystalline materials which are discotic;

thiophenes, oligothiophenes and substituted derivatives thereof. Suitable oligothiophenes are quaterthiophenes, quinquethiophenes, sexithiophenes, $\alpha,\omega$-di($C_1$-$C_8$)alkyloligothiophenes such as $\alpha,\omega$-dihexylquaterthiophenes, $\alpha,\omega$-dihexylquinquethiophenes and $\alpha,\omega$-dihexylsexithiophenes, poly(alkylthiophenes) such as poly(3-hexylthiophene), bis(dithienothiophenes), anthradithiophenes and dialkylanthradithiophenes such as dihexylanthradithiophene, phenylene-thiophene (P-T) oligomers and derivatives thereof, especially $\alpha,\omega$-alkyl-substituted phenylene-thiophene oligomers;

also suitable are compounds of the $\alpha,\alpha'$-bis(2,2-dicyanovinyl)quinquethiophene (DCV5T) type, (3-(4-octylphenyl)-2,2'-bithiophene) (PTOPT), poly(3-(4'-(1,4,7-trioxaoctyl)phenyl)thiophene) (PEOPT), poly(3-(Z-methoxy-5'-octylphenyl)thiophene) (POMeOPT), poly(3-octylthiophene) (P3OT), poly(pyridopyrazinevinylene)-polythiophene blends, such as EHH-PpyPz, PTPTB copolymers, BBL, F8BT, PFMO; see Brabec C., Adv. Mater., 2996, 18, 2884, (PCPDTBT) poly[2,6-(4,4-bis(2-ethylhexyl)-4H-cyclopenta[2,1-b;3,4-b']dithiophene)-4,7-(2,1,3-benzothiadiazole)];

paraphenylenevinylene and paraphenylenevinylene-comprising oligomers and polymers, for example polyparaphenylenevinylene, MEH-PPV (poly(2-methoxy-5-(2'-ethylhexyloxy)-1,4-phenylenevinylene)), MDMO-PPV (poly (2-methoxy-5-(3',7'-dimethyloctyloxy)-1,4-phenylenevinylene)), PPV, CN-PPV (with various alkoxy derivatives);

phenyleneethynylene/phenylenevinylene (PPE-PPV) hybrid polymers;

polyfluorenes and alternating polyfluorene copolymers, for example with 4,7-dithien-2'-yl-2,1,3-benzothiadiazole; also suitable are poly(9,9'-dioctylfluorene-co-benzothiadiazole) ($F_8BT$), poly(9,9'-dioctylfluorene-co-bis-N,N'-(4-butylphenyl)-bis-N,N'-phenyl-1,4-phenylenediamine) (PFB);

polycarbazoles, i.e. carbazole-comprising oligomers and polymers, such as (2,7) and (3,6).

Polyanilines, i.e. aniline-comprising oligomers and polymers, such as (2,7) and (3,6).

Triarylamines, polytriarylamines, polycyclopentadienes, polypyrroles, polyfurans, polysiloles, polyphospholes, TPD, CBP, spiro-MeOTAD.

Fullerenes, especially C60 and derivatives thereof such as PCBM (=[6,6]-phenyl-$C_{61}$-butyric acid methyl ester). In such cells, the fullerene derivative is a hole conductor.

Copper(I) iodide, copper(I) thiocyanate.

p-n-Mixed materials, i.e. donor and acceptor in one material, polymer, block polymer, polymers with C60s, C60 azo dyes, triad carotenoid-porphyrin-quinoid LC donor/acceptor systems, as described by S. Kelly in Adv. Mater. 2006, 18, 1754.

All aforementioned semiconductor materials may also be doped. Examples of dopants for p-semiconductors: 2,3,5,6-tetrafluoro-7,7,8,8-tetracyanoquinodimethane ($F_4$-TCNQ), etc.

The inventive (novel) compounds (I) are also suitable particularly advantageously as organic semiconductors. They function generally as n-semiconductors. When the compounds of the formula (I) used in accordance with the invention are combined with other semiconductors and the position of the energy levels causes the other semiconductors to function as n-semiconductors, the compounds (I) can also function as p-semiconductors in exceptional cases. This is the case, for example, for the combination with cyano-substituted perylenetetracarboximides. The compounds of the formula (I) are notable for their air stability. They also possess a high charge transport mobility and have a high on/off ratio. They are suitable in a particularly advantageous manner for organic field-effect transistors. The inventive compounds are advantageously suitable for preparing integrated circuits (ICs) for which the n-channel MOSFETs (metal oxide semiconductor field-effect transistors) customary to date are used. These are CMOS-like semiconductor units, for example for microprocessors, microcontrollers, static RAM and other digital logic units. For the production of semiconductor materials, the processes according to the invention can be processed further by one of the following processes: printing (offset, flexographic, gravure, screen, inkjet, electrophotography), evaporation, laser transfer, photolithography, dropcasting. They are suitable in particular for use in displays (especially large-area and/or flexible displays) and RFID tags.

The inventive compounds are also suitable particularly advantageously for data storage in diodes, especially in OLEDs, in photovoltaics, as UV absorbers, as optical brighteners, as invisible labels and as fluorescent labels for biomolecules such as proteins, DNA, sugars and combinations thereof.

The inventive compounds are also suitable particularly advantageously as a fluorescent dye in a display based on fluorescence conversion; in a light-collecting plastics part which may be combined with a solar cell; as a pigment dye in electrophoretic displays; as a fluorescent dye in an application based on chemoluminescence (for example in glow sticks).

The inventive compounds are also particularly advantageously suitable as a fluorescent dye in a display based on fluorescence conversion. Such displays generally comprise a transparent substrate, a fluorescent dye disposed on the substrate and a radiation source. Customary radiation sources transmit blue (color-by-blue) or UV light (color-by-uv). The dyes absorb either the blue or the UV light and are used as green emitters. In these displays, for example, the red light is generated by virtue of the red emitter being excited by a blue or UV light-absorbing green emitter. Suitable color-by-blue displays are described, for example, in WO 98/28946. Suitable color-by-uv displays are described, for example, by W. A. Crossland, I. D. Sprigle and A. B. Davey in Photoluminescent LCDs (PL-LCD) using phosphors Cambridge University and Screen Technology Ltd., Cambridge, UK.

The inventive compounds are also particularly suitable as fluorescence emitters in OLEDs, in which they are excited either by electroluminescence or by an appropriate phosphorescence emitter via Förster energy transfer (FRET).

The inventive compounds are also particularly suitable in displays which switch colors on and off based on an electrophoretic effect via charged pigment dyes. Such electrophoretic displays are described, for example, in US 2004/0130776.

The inventive compounds are also particularly suitable for use in a light-collecting plastics part which absorbs light over a large surface and at whose edges the light is emitted after multiple refraction (so-called LISAs). Such LISAs may have, at the edges, solar cells, for example silicon solar cells or organic solar cells, which convert the concentrated light to electrical energy. A combination of light-collecting plastics with solar cells is described, for example, in U.S. Pat. No. 4,110,123.

The inventive compounds are also particularly suitable in chemoluminescence applications. These include so-called "glow sticks". They can be produced by dissolving at least one compound of the formula (I), for example in an alkyl phthalate.

The chemoluminescence can be induced by mixing an oxalic ester with hydrogen peroxide, for example after these two initially separate components have been mixed by breaking a piece of glass. The resulting reaction energy leads to the excitation and fluorescence of the dyes. Such glow sticks can be used as emergency light, for example for angling, in lifejackets for emergency sea rescue or other safety applications.

The invention further provides organic field-effect transistors comprising a substrate having at least one gate structure, a source electrode and a drain electrode and at least one compound of the formula I as defined above as an n-semiconductor. The invention further provides substrates comprising a multitude of organic field-effect transistors, wherein at least some of the field-effect transistors comprise at least one compound of the formula I as defined above as an n-semiconductor. The invention also provides semiconductor units which comprise at least one such substrate.

A specific embodiment is a substrate with a pattern (topography) of organic field-effect transistors, each transistor comprising an organic semiconductor disposed on the substrate;
a gate structure for controlling the conductivity of the conductive channel; and
conductive source and drain electrodes at the two ends of the channel the organic semiconductor consisting of at least one compound of the formula (I) or comprising a compound of the formula (I). In addition, the organic field-effect transistor generally comprises a dielectric.

A further specific embodiment is a substrate having a pattern of organic field-effect transistors, each transistor forming an integrated circuit or being part of an integrated circuit and at least some of the transistors comprising at least one compound of the formula (I).

Suitable substrates are in principle the materials known for this purpose. Suitable substrates comprise, for example, metals (preferably metals of groups 8, 9, 10 or 11 of the Periodic Table, such as Au, Ag, Cu), oxidic materials (such as glass, quartz, ceramics, $SiO_2$), semiconductors (e.g. doped Si, doped Ge), metal alloys (for example based on Au, Ag, Cu, etc.), semiconductor alloys, polymers (e.g. polyvinyl chloride, polyolefins such as polyethylene and polypropylene, polyesters, fluoropolymers, polyamides, polyimides, polyurethanes, polyalkyl (meth)acrylates, polystyrene and mixtures and composites thereof), inorganic solids (e.g. ammonium chloride), paper and combinations thereof. The substrates may be flexible or inflexible, and have a curved or planar geometry, depending on the desired use.

A typical substrate for semiconductor units comprises a matrix (for example a quartz or polymer matrix) and, optionally, a dielectric top layer.

Suitable dielectrics are $SiO_2$, polystyrene, poly-α-methylstyrene, polyolefins (such as polypropylene, polyethylene, polyisobutene), polyvinylcarbazole, fluorinated polymers (e.g. Cytop, CYMM), cyanopullulans, polyvinylphenol, poly-p-xylene, polyvinyl chloride, or polymers crosslinkable thermally or by atmospheric moisture. Specific dielectrics are "self-assembled nanodielectrics", i.e. polymers which are obtained from monomers comprising SiCl functionalities, for example $Cl_3SiOSiCl_3$, $Cl_3S(HCH_2)_6$—$SiCl_3$, $Cl_3Si$—$(CH_2)_{12}$—$SiCl_3$, and/or which are crosslinked by atmospheric moisture or by addition of water diluted with solvents (see, for example, Faccietti Adv. Mat. 2005, 17, 1705-1725). Instead of water, it is also possible for hydroxyl-containing polymers such as polyvinylphenol or polyvinyl alcohol or copolymers of vinylphenol and styrene to serve as crosslinking components. It is also possible for at least one further polymer to be present during the crosslinking operation, for example polystyrene, which is then also crosslinked (see Facietti, US patent application 2006/0202195).

The substrate may additionally have electrodes, such as gate, drain and source electrodes of OFETs, which are normally localized on the substrate (for example deposited onto or embedded into a nonconductive layer on the dielectric). The substrate may additionally comprise conductive gate electrodes of the OFETs, which are typically arranged below the dielectric top layer (i.e. the gate dielectric).

In a specific embodiment, an insulator layer (gate insulating layer) is present on at least part of the substrate surface. The insulator layer comprises at least one insulator which is preferably selected from inorganic insulators such as $SiO_2$, SiN, etc., ferroelectric insulators such as $Al_2O_3$, $Ta_2O_5$, $La_2O_5$, $TiO_2$, $Y_2O_3$, etc., organic insulators such as polyimides, benzocyclobutene (BCB), polyvinyl alcohols, polyacrylates, etc., and combinations thereof.

Suitable materials for source and drain electrodes are in principle electrically conductive materials. These include metals, preferably metals of groups 8, 9, 10 or 11 of the Periodic Table, such as Pd, Au, Ag, Cu, Al, Ni, Cr, etc. Also suitable are conductive polymers such as PEDOT (=poly(3,4-ethylenedioxythiophene)); PSS (=poly(styrenesulfonate)), polyaniline, surface-modified gold, etc. Preferred electrically conductive materials have a specific resistance of less than $10^{-3}$ ohm×meter, preferably less than $10^{-4}$ ohm×meter, especially less than $10^{-6}$ or $10^{-7}$ ohm×meter.

In a specific embodiment, drain and source electrodes are present at least partly on the organic semiconductor material. It will be appreciated that the substrate may comprise further components as used customarily in semiconductor materials or ICs, such as insulators, resistors, capacitors, conductor tracks, etc.

The electrodes may be applied by customary processes, such as evaporation, lithographic processes or another structuring process.

The semiconductor materials may also be processed with suitable auxiliaries (polymers, surfactants) in disperse phase by printing.

In a first preferred embodiment, the deposition of at least one compound of the general formula I (and if appropriate further semiconductor materials) is carried out by a gas phase deposition process (physical vapor deposition, PVD). PVD processes are performed under high-vacuum conditions and comprise the following steps: evaporation, transport, deposition. It has been found that, surprisingly, the compounds of the general formula I are suitable particularly advantageously for use in a PVD process, since they essentially do not decompose and/or form undesired by-products. The material deposited is obtained in high purity. In a specific embodiment, the deposited material is obtained in the form of crystals or comprises a high crystalline content. In general, for the PVD, at least one compound of the general formula I is heated to a temperature above its evaporation temperature and deposited on a substrate by cooling below the crystallization temperature. The temperature of the substrate in the deposition is preferably within a range from about 20 to 250° C., more preferably from 50 to 200° C. It has been found that, surprisingly, elevated substrate temperatures in the deposition of the compounds of the formula I can have advantageous effects on the properties of the semiconductor elements achieved.

The resulting semiconductor layers generally have a thickness which is sufficient for ohmic contact between source and drain electrodes. The deposition can be effected under an inert atmosphere, for example under nitrogen, argon or helium.

The deposition is effected typically at ambient pressure or under reduced pressure. A suitable pressure range is from about $10^{-7}$ to 1.5 bar.

The compound of the formula (I) is preferably deposited on the substrate in a thickness of from 10 to 1000 nm, more preferably from 15 to 250 nm. In a specific embodiment, the compound of the formula I is deposited at least partly in crystalline form. For this purpose, especially the above-described PVD process is suitable. Moreover, it is possible to use previously prepared organic semiconductor crystals. Suitable processes for obtaining such crystals are described by R. A. Laudise et al. in "Physical Vapor Growth of Organic Semi-Conductors", Journal of Crystal Growth 187 (1998), pages 449-454, and in "Physical Vapor Growth of Centimeter-sized Crystals of α-Hexathiophene", Journal of Crystal Growth 1982 (1997), pages 416-427, which are incorporated here by reference.

Compounds of the general formula (I) where at least one of the $R''^1$, $R''^2$, $R''^3$ and $R''^4$ radicals has an aryl group or hetaryl group which bears at least two substituents which are each independently selected from $C_4$-$C_{30}$-alkyl, $C_4$-$C_{30}$-alkoxy and $C_4$-$C_{30}$-alkylthio, where the alkyl radicals of the alkyl, alkoxy and alkylthio substituents may also be interrupted by one or more nonadjacent oxygen atom(s), can also particularly advantageously be processed from solution. In a second preferred embodiment, the deposition of at least one such compound of the general formula (I) (and if appropriate further semiconductor materials) is therefore effected by spin-coating. These compounds of the formula (I) should also be suitable for producing semiconductor elements, especially OFETs or based on OFETs, by a printing process. It is possible for this purpose to use customary printing processes (inkjet, flexographic, offset, gravure; intaglio printing, nanoprinting). Preferred solvents for the use of the compounds of the formula (I) in a printing process are aromatic solvents such as toluene, xylene, etc. It is also possible to add thickening substances such as polymers, for example polystyrene, etc., to these "semiconductor inks". In this case, the dielectrics used are the aforementioned compounds.

In a preferred embodiment, the inventive field-effect transistor is a thin-film transistor (TFT). In a customary construction, a thin-film transistor has a gate electrode disposed on the substrate, a gate insulator layer disposed thereon and on the substrate, a semiconductor layer disposed on the gate insulator layer, an ohmic contact layer on the semiconductor layer, and a source electrode and a drain electrode on the ohmic contact layer.

In a preferred embodiment, the surface of the substrate, before the deposition of at least one compound of the general formula (I) (and if appropriate of at least one further semiconductor material), is subjected to a modification. This modification serves to form regions which bind the semiconductor materials and/or regions on which no semiconductor materials can be deposited. The surface of the substrate is preferably modified with at least one compound (C1) which is suitable for binding to the surface of the substrate and to the compounds of the formula (I). In a suitable embodiment, a portion of the surface or the complete surface of the substrate is coated with at least one compound (C1) in order to enable improved deposition of at least one compound of the general formula (I) (and if appropriate further semiconductive compounds). A further embodiment comprises the deposition of a pattern of compounds of the general formula (C1) on the substrate by a corresponding production process. These include the mask processes known for this purpose and so-called "patterning" processes, as described, for example, in U.S. Ser. No. 11/353,934, which is incorporated here fully by reference.

Suitable compounds of the formula (C1) are capable of a binding interaction both with the substrate and with at least one semiconductor compound of the general formula I. The term "binding interaction" comprises the formation of a chemical bond (covalent bond), ionic bond, coordinative interaction, van der Waals interactions, e.g. dipole-dipole interactions etc., and combinations thereof. Suitable compounds of the general formula (C1) are:

Silanes, phosphonic acids, carboxylic acids, hydroxamic acids, such as alkyltrichlorosilanes, e.g. n-octadecyltrichlorosilane; compounds with trialkoxysilane groups, e.g. alkyltrialkoxysilanes such as n-octadecyltrimethoxy-silane, n-octadecyltriethoxysilane, n-octadecyltri(n-propyl)oxysilane, n-octadecyltri(isopropyl)oxysilane; trialkoxyaminoalkylsilanes such as triethoxyaminopropylsilane and N-[(3-triethoxysilyl)propyl]ethylenediamine; trialkoxyalkyl 3-glycidyl ether silanes such as triethoxypropyl 3-glycidyl ether silane; trialkoxyallylsilanes such as allyltrimethoxysilane; trialkoxy(isocyanato-alkyl)silanes; trialkoxysilyl(meth)acryloyloxyalkanes and trialkoxysilyl(meth)-acrylamidoalkanes such as 1-triethoxysilyl-3-acryloyloxypropane.

Amines, phosphines and sulfur-comprising compounds, especially thiols.

The compound (C1) is preferably selected from alkyltrialkoxysilanes, especially n-octadecyltrimethoxysilane, n-octadecyltriethoxysilane; hexaalkyldisilazanes, and especially hexamethyldisilazane (HMDS); $C_8$-$C_{30}$-alkylthiols, especially hexadecanethiol; mercaptocarboxylic acids and mercaptosulfonic acids, especially mercaptoacetic acid, 3-mercaptopropionic acid, mercaptosuccinic acid, 3-mercapto-1-propanesulfonic acid and the alkali metal and ammonium salts thereof.

Various semiconductor architectures comprising the inventive semiconductors are also conceivable, for example top contact, top gate, bottom contact, bottom gate, or else a vertical construction, for example a VOFET (vertical organic field-effect transistor), as described, for example, in US 2004/0046182.

The layer thicknesses are, for example, from 10 nm to 5 µm in semiconductors, from 50 nm to 10 µl in the dielectric; the electrodes may, for example, be from 20 nm to 1 μm thick. The OFETs may also be combined to form other components such as ring oscillators or inverters.

A further aspect of the invention is the provision of electronic components which comprise a plurality of semiconductor components, which may be n- and/or p-semiconductors. Examples of such components are field-effect transistors (FETs), bipolar junction transistors (BJTs), tunnel diodes, converters, light-emitting components, biological and chemical detectors or sensors, temperature-dependent detectors, photodetectors such as polarization-sensitive photodetectors, gates, AND, NAND, NOT, OR, TOR and NOR gates, registers, switches, timer units, static or dynamic stores and other dynamic or sequential, logical or other digital components including programmable circuits.

A specific semiconductor element is an inverter. In digital logic, the inverter is a gate which inverts an input signal. The inverter is also referred to as a NOT gate. Real inverter circuits have an output current which constitutes the opposite of the input current. Typical values are, for example, (0, +5V) for TTL circuits. The performance of a digital inverter reproduces the voltage transfer curve (VTC), i.e. the plot of input current against output current. Ideally, it is a staged function, and the closer the real measured curve approximates to such a stage, the better the inverter is. In a specific embodiment of the invention, the compounds of the formula (I) are used as organic n-semiconductors in an inverter.

The invention will be illustrated in detail with reference to the nonrestricitive examples which follow.

EXAMPLES

Example 1

N,N'-Di(1-heptyloctyl)terrylene-3,4:11,12-tetracarboximide (2)

1.1 N-(1-heptyloctyl)-4-bromonaphthalene-1,8-dicarboximide 5 g (18 mmol) of 4-bromonaphthalene-1,8-dicarboxylic anhydride were heated to 160° C. with 6.1 g (27 mmol) of 1-heptyloctylamine in 50 ml of ethylene glycol for 4 hours. The resulting solution was allowed to cool to room temperature. Thereafter, the solution was diluted with 50 ml of methanol and 50 ml of distilled water. The aqueous solution was extracted with diethyl ether, the solution was dried over $MgSO_4$ and the solvent was evaporated. The resulting yellow oil was purified by column chromatography with dichloromethane as the eluent, which afforded 5.5 g (63%) of the title compound as a colorless oil.

$^1$H NMR (300 MHz, $C_2D_2Cl_4$, 25° C.): δ [ppm]=8.53 (m, 1H), 8.44 (d, 1H, J=8.5 Hz), 8.29 (m, 1H), 7.95 (d, 1H, J=7.9 Hz), 7.76 (t, 1H, J=7.6 Hz), 5.08-4.96 (m, 1H), 2.15-2.06 (m, 2H), 1.77-1.70 (m, 2H), 1.17-1.10 (m, 20 H), 0.77-0.72 (m, 6H).

$^{13}$C NMR (75 MHz, $C_2D_2Cl_4$, 25° C.): δ [ppm]=165.02, 163.88, 133.19, 132.67, 131.38, 131.22, 130.69, 130.21, 129.35, 128.41, 123.98, 123.25, 123.12, 122.39, 54.91, 32.57, 32.15, 29.57, 27.22, 22.98, 14.50.

IR (NaCl): ν (cm$^{-1}$)=2924, 2854, 2362, 1704, 1663, 1619, 1588, 1508, 1461, 1400, 1342, 1239, 783

MS (FD): 486.1 (100%) [M$^+$] (calculated for $C_{27}H_{36}NBrNO_2$ 486.50)

1.2 N-(1-heptyloctyl)perylene-3,4-dicarboximide 6 g (19 mmol) of perylene-3,4-dicarboxylic anhydride were stirred with 10.7 g (47 mmol) of 1-heptyloctylamine in 100 ml of quinoline at 160° C. under argon for 12 hours. Thereafter, the reaction mixture was allowed to cool to room temperature and diluted with hydrochloric acid. The precipitate was filtered off and dried under reduced pressure. The crude product was purified by chromatography on silica gel with dichloromethane as the eluent, which afforded 8.4 g (83%) of a red solid with a melting point of 156° C.

$^1$H NMR (250 MHz, $C_2D_2Cl_4$, 25° C.): δ [ppm]=8.38 (m, 2H), 8.17 (d, 2H, J=7.9 Hz), 8.12 (d, 2H, J=8.2 Hz), 7.75 (d, 2H, J=7.9 Hz), 7.47 (t, 2H, J=7.6 Hz), 5.17-5.05 (m, 1H), 2.23-2.16 (m, 2H), 1.89-1.81 (m, 2H), 1.27-1.20 (m, 20H), 0.82-0.77 (m, 6H).

$^{13}$C NMR (62.5 MHz, $C_2D_2Cl_4$, 25° C.): δ [ppm]=165.24, 164.24, 136.85, 134.22, 131.90, 131.20, 131.00, 129.83, 129.09, 127.79, 127.16, 126.53, 123.77, 121.61, 120.84, 120.21, 54.58, 32.65, 32.15, 29.91, 29.58, 27.39, 22.97, 14.50.

IR (KBr): ν (cm$^{-1}$)=2924, 2853, 2365, 1697, 1653, 1594, 1572, 1450, 1460, 1408, 1355, 1292, 1244, 1172, 1136, 1109, 840, 754.

UV-Vis (CHCl$_3$): λ$_{max}$ (ε)=511 (50000), 489 nm (50000 M$^{-1}$ cm$^{-1}$)

Fluorescence (CHCl$_3$): λ$_{max}$=571, 544 nm.

MS (FD): 531.2 (100%) [α](calculated for $C_{37}H_{41}NO_2$ 531.74)

1.3 N-(1-heptyloctyl)-9-bromoperylene-3,4-dicarboximide 8 g (15.05 mmol) of N-(1-heptyloctyl)perylene-3,4-dicarboximide from Example 1.2 were suspended in 100 ml of acetic acid for 30 minutes. Thereafter, 150 mg (0.6 mmol) of iodine and 9.6 g (60.2 mmol) of bromine were added to the mixture and the resulting mixture was stirred at room temperature with the exclusion of light for 4.5 hours. To remove excess bromine, argon was introduced into the flask and the mixture was precipitated with 100 ml of methanol and stirred overnight. The product was filtered off and washed with 150 ml of methanol. After drying under reduced pressure, 8.9 g (97%) of the title compound with a melting point of 163° C. were obtained.

$^1$H NMR (500 MHz, CD$_2$Cl$_2$, 25° C.): δ [ppm]=8.63 (d, 1H, J=8.2 Hz), 8.61 (d, 1H, J=8.2 Hz), 8.45 (d, 1H, J=8.2 Hz), 8.42 (d, 1H, J=8.2 Hz), 8.36 (d, 1H, J=7.6 Hz), 8.27 (d, 1H, J=8.2 Hz), 8.20 (d, 1H, J=8.2 Hz), 7.87 (d, 1H, J=8.2 Hz), 7.70 (t, 1H, J=7.6 Hz), 5.17-5.05 (m, 1H), 2.23-2.16 (m, 2H), 1.89-1.81 (m, 2H), 1.27-1.20 (m, 20 H), 0.82-0.77 (m, 6H).

$^{13}$C NMR (Spinecho, 125 MHz, CD$_2$Cl$_2$, 25° C.): δ [ppm]=165.16, 164.12, 136.16, 132.73, 132.01, 131.26, 129.90, 129.73, 129.47, 128.93, 128.20, 126.14, 126.08, 124.38, 123.67, 122.06, 121.31, 120.75, 120.48, 54.69, 32.65, 32.15, 29.90, 29.59, 27.40, 22.98, 14.53.

IR (KBr): ν (cm$^{-1}$)=2924, 2853, 2365, 1697, 1653, 1594, 1572, 1450, 1460, 1408, 1355, 1292, 1244, 1172, 1136, 1109, 840, 810, 754.

UV-Vis (CHCl$_3$): λ$_{max}$ (ε)=514 (51000), 489 (52000 M$^{-1}$ cm$^{-1}$)

Fluorescence (CHCl$_3$): λ$_{max}$=571, 544 nm.

MS (FD): 611.1 (100%) [M$^+$] (calculated for $C_{37}H_{40}BrNO_2$ 610.64)

1.4 N-(1-heptyloctyl)-9-(4,4,5,5-tetramethyl-1,3,2-dioxaborolan-2-yl)perylene-3,4-dicarboximide To 1.2 g (2 mmol) of N-(1-heptyloctyl)-9-bromoperylene-3,4-dicarboximide from Example 1.3 and 558 mg (2.5 mmol) of bis(pinacolato)diboron were added, under a gentle argon stream, 588 mg (5.3 mmol) of potassium acetate in 20 ml of dioxane. Subsequently, 44 mg (0.1 mmol) of [1,1'-bis(diphenylphosphino)ferrocene]palladium(II) chloridemethyl chloride ([PdCl$_2$(dppf)]xCH$_2$Cl$_2$) were added and the reaction mixture was stirred under an argon atmosphere at 70° C. for 16 hours. After cooling to room temperature, the mixture was extracted with dichloromethane and the extract was washed twice with distilled water. The organic layer was removed and dried over magnesium sulfate, and the crude product was purified by column chromatography with dichloromethane as the eluent, which afforded 1.0 g (78%) of the title compound as a red solid with a melting point of 213° C.

$^1$H NMR (300 MHz, THF-d$_8$, 25° C.): δ [ppm]=8.87 (d, 1H, J=7.7 Hz), 8.55-8.47 (m, 6H), 8.15 (d, 1H, J=7.7 Hz), 7.59 (t, 1H, J=7.7 Hz), 5.27-5.17 (m, 1 H), 2.40-2.28 (m, 2H), 1.84-1.77 (m, 2H), 1.44 (s, 12H), 1.34-1.24 (m, 20H), 0.85-0.81 (t, 6H, J=6.8 Hz).

$^{13}$C NMR (75 MHz, THF-d8, 25° C.): δ [ppm]=165.24, 164.33, 139.04, 137.83, 137.28, 132.81, 132.20, 131.45, 130.64, 130.02, 128.60, 127.81, 127.40, 124.38, 123.34, 123.25, 122.04, 121.90, 121.28.

IR (KBr): v (cm$^{-1}$)=2925, 2854, 2362, 2337, 1691, 1653, 1592, 1507, 1461, 1416, 1376, 1332, 1272, 1246, 1209, 1142, 1113, 1068, 966, 858, 811, 754, 674

UV-Vis (CHCl$_3$): λ$_{max}$ (ϵ)=514 (47000), 489 nm (45000 M$^{-1}$ cm$^{-1}$).

Fluorescence (CHCl$_3$): λ$_{max}$=577, 546 nm.

MS (FD): 657.2 (100%) [M$^+$] (calculated for C$_{43}$H$_{52}$BN$_2$O$_4$ 657.71)

1.5 N-(1-heptyloctyl)-9-(4-N-(1-heptyloctyl)-naphthalene-1,8-dicarboximide)perylene-3,4-dicarboximide 1.0 g (1.52 mmol) of N-(1-heptyloctyl)-9-(4,4,5,5-tetramethyl-1,3,2-dioxaborolan-2-yl)perylene-3,4-dicarboximide from Example 1.4 and 0.813 g (1.67 mmol) of N-(1-heptyloctyl)-4-bromonaphthalene-1,8-dicarboximide from Example 1.1 were dissolved in 76 ml of toluene. A solution of Na$_2$CO$_3$ in water (63 ml, 1 M) and ethanol (5 ml) was added and the solution was purged with argon. Thereafter, [Pd(PPh$_3$)$_4$] (80 mg, 0.06 mmol) was added and the reaction mixture was stirred at 80° C. for 16 h. The reaction mixture was allowed to cool to room temperature. The organic phase was removed and the solvent was evaporated under reduced pressure. The product was purified by chromatography on silica gel with dichloromethane as the eluent, which afforded 1.1 g (79%) as a red solid having a melting point of 129° C.

$^1$H NMR (700 MHz, C$_2$D$_2$Cl$_4$, 130° C.) δ [ppm]=8.68 (d, 1H, J=6.7 Hz), 8.64-8.56 (m, 3H), 8.53 (d, 1H), 8.47 (d, 1H), 8.45-8.39 (m, 2H), 7.85-7.75 (m, 2H), 7.62 (d, 1H, J=6.8 Hz), 7.59-7.54 (m, 1H), 7.45 (d, 1H, J=7.1 Hz), 7.41 (d, 1H, J=7.8 Hz), 5.22-5.11 (m, 2H), 2.31-2.19 (m, 4H), 1.98-1.86 (m, 4H), 1.41-1.19 (m, 40H), 0.93-0.77 (m, 12H).

$^{13}$C NMR (175 MHz, C$_2$D$_2$Cl$_4$, 130° C.): δ [ppm]=164.77, 164.63, 164.53, 144.02, 139.39, 136.84, 136.57, 133.87, 131.96, 131.64, 131.60, 131.36, 131.33, 130.58, 130.51, 130.27, 130.24, 129.32, 129.09, 129.03, 127.71, 127.32, 127.06, 124.18, 123.91, 123.83, 122.94, 122.64, 122.50, 120.89, 120.80, 55.16, 55.00, 32.93, 32.90, 31.93, 31.90, 29.64, 29.24, 27.24, 22.61, 13.92.

IR (KBr): v (cm$^{-1}$)=2956, 2927, 2850, 1697, 1654, 1590, 1577, 1348, 811.

UV-Vis (CHCl$_3$): λ$_{max}$(ϵ)=508 (40000), 482 (39000), 350 (14.000), 335 nm (16000 M$^{-1}$ cm$^{-1}$)

MS (FD): 937.5 (100%) [M$^+$] (calculated for C$_{64}$H$_{76}$N$_2$O$_4$ 937.33)

1.6 N,N'-di(1-heptyloctyl)terrylene-3,4:11,12-tetracarboximide 0.9 g (0.96 mmol) of N-(1-heptyloctyl)-9-(4-N-(1-heptyloctyl)naphthalene-1,8-dicarboximide)perylene-3,4-dicarboximide, 6.42 g (46.5 mmol) of K$_2$CO$_3$ and 9.0 g (0.147 mol) of ethanolamine were stirred at 160° C. under argon for 3 h. After cooling to room temperature, the solution was poured into methanol (20 ml). The precipitate was filtered off, washed with water, dried under reduced pressure and purified by column chromatography on silica gel (CH$_2$Cl$_2$), which afforded a blue product (0.763 g, 85%) having a melting point of 278.13° C.

$^1$H NMR (250 MHz, THF-d$_8$, 25° C.): δ [ppm]=8.25 (s, 4H), 8.18 (d, 8H, J=8.5 Hz), 5.21 (m, 2H), 2.37 (m, 4H, J=6.95 Hz), 1.92 (m, 4H), 1.42-1.30 (m, 40H), 0.89-0.84 (m, 12 H).

$^{13}$C NMR (125 MHz, THF-d$_8$, 25° C.): δ [ppm]=164.43, 163.52, 135.18, 130.52, 129.77, 127.85, 125.76, 124.35, 122.90, 122.04, 121.34, 54.78, 33.20, 32.79, 30.51, 30.17, 28.06, 23.43, 14.34.

IR (KBr): v (cm$^{-1}$)=2923, 2852, 1694, 1652, 1585, 1379, 1353, 1323, 807.

UV-Vis (CHCl3): λ$_{max}$ (ϵ)=651 (127000), 598 (66000), 547 nm (21000 M$^{-1}$ cm$^{-1}$).

Fluorescence (CHCl$_3$): λ$_{max}$=669, 729 nm

MS (FD): 935.6 (100%) [M$^+$] (calculated for C$_{64}$H$_{74}$N$_2$O$_4$ 935.31)

Example 2

N,N'-di(1-heptyloctyl)quaterrylene-3,4:13,14-tetracarboximide (3)

2.1 N,N'-bis(1-heptyloctyl)-9,9'-biperylene-3, 4:3',4'-bis(dicarboximide)

0.2 g (0.3 mmol) of N-(1-heptyloctyl)-9-(4,4,5,5-tetramethyl-1,3,2-dioxaborolan-2-yl)perylene-3,4-dicarboximide from Example 1.4 and 0.37 g (0.6 mmol) of N-(1-heptyloctyl)-9-bromoperylene-3,4-dicarboximide from Example 1.3 were dissolved in toluene (15 ml). A solution of Na$_2$CO$_3$ in water (10 ml, 1 M) and ethanol (5 ml) was added and the mixture was purged with argon. Thereafter, [Pd(PPh$_3$)$_4$] (16 mg, 0.01 mmol) was added and the reaction mixture was stirred at 80° C. for 16 h. The reaction mixture was allowed to cool to room temperature. The organic phase was removed and the solvent was evaporated under reduced pressure. The crude product was purified by chromatography on silica gel with dichloromethane as the eluent, which afforded 0.24 g (76%) of a red solid having a melting point of 304° C.

$^1$H NMR (700 MHz, C$_2$D$_2$Cl$_4$, 130° C.): δ [ppm]=8.65-8.57 (m, 4H), 8.54 (d, 2H, J=7.4 Hz), 8.47 (d, 2H, J=7.7 Hz), 8.45-8.40 (m, 4H), 7.68 (d, 2H, J=7.3 Hz), 7.55 (d, 2H, J=8.0 Hz), 7.46 (t, 2H, J=8.0 Hz), 5.22-5.11 (m, 2H), 2.30-2.19 (m, 4H), 1.97-1.85 (m, 4H), 1.37-1.19 (m, 40H), 0.94-0.780,84 (m, 12H).

$^{13}$C NMR (75 MHz, C$_2$D$_2$Cl$_4$, 130° C.): δ [ppm]=164.58, 140.68, 137.01, 136.80, 134.15, 131.63, 130.29, 130.19, 130.10, 129.45, 129.24, 128.83, 127.56, 127.08, 123.88, 123.18, 122.46, 122.39, 120.77, 120.65, 54.99, 32.91, 31.91, 29.66, 29.26, 27.26, 22.62, 13.93.

IR (KBr): v (cm$^{-1}$)=2954, 2925, 2854, 1693, 1653, 1593, 1572, 1352, 812

UV-Vis (CHCl$_3$): $\lambda_{max}$ ($\epsilon$)=527 nm (97000 M$^{-1}$ cm$^{-1}$)

MS (FD): 1060.0 (100%) [M$^+$] (calculated for C$_{74}$H$_{80}$N$_2$O$_4$ 1061.47)

2.2 N,N'-di(1-heptyloctyl)quaterrylene-3,4:13,14-tetracarboximide 0.2 g (0.19 mmol) of N,N'-bis(1-heptyloctyl)-9,9'-biperylene-3, 4:3',4'-bis(dicarboximide) from Example 2.1, 1.26 g (9.1 mmol) of K$_2$CO$_3$ and 1.7 g (0.028 mol) of ethanolamine were stirred under argon at 160° C. for 3 h. After cooling to room temperature, the solution was poured into methanol (10 ml). The precipitate was filtered off, washed with water, dried under reduced pressure and purified by column chromatography on silica gel with dichloromethane as the eluent, which afforded a blue-green product (0.165 g, 83%) having a melting point above 350° C.

$^1$H NMR (300 MHz, C$_2$D$_2$Cl$_4$, 120° C.): δ [ppm]=8.47 (m, 16H), 5.17 (m, 2H), 2.25 (m, 4H), 1.93 (m, 4H), 1.32 (m, 40H), 0.84 (m, 12H)

$^{13}$C NMR (75 MHz, THF-d8, 25° C.): δ [ppm]=164.14, 163.79, 140.81, 135.80, 131.51, 130.38, 129.34, 127.99, 127.17, 126.34, 124.15, 123.21, 120.68, 55.03, 33.51, 33.03, 30.81, 30.43, 28.38, 23.65, 14.56

IR (KBr): ν (cm$^{-1}$)=2956, 2925, 2856, 1693, 1652, 1575, 1349, 1286, 809

UV-Vis (CHCl3): $\lambda_{max}$ ($\epsilon$)=762 nm (162000 M$^{-1}$ cm$^{-1}$)

MS (FD): 1058.1 (100%) [M$^+$] (calculated for C$_{74}$H$_{78}$N$_2$O$_4$ 1059.4)

Example 3

N,N'-di(1-heptyloctyl)-5,11-didecylcoronene-2,3:8,9-tetracarboximide (4)

3.1 N,N'-bis(1-heptyloctyl)-1,7-dibromoperylene-3,4:9,10-tetracarboximide

A mixture of 0.5 g (0.909 mmol) of 1,7-dibromoperylene-3,4:9,10-tetracarboxylic dianhydride and 0.75 g (3.298 mmol) of 1-heptyloctylamine in 50 ml of N-methylpyrrolidone was stirred at 150° C. for 4 h. After cooling to room temperature, the solution was poured into dilute hydrochloric acid (400 ml). The precipitate was filtered off, washed with water and methanol, dried under reduced pressure and purified by column chromatography on silica gel (3/2 petroleum ether/CH$_2$Cl), which afforded 0.34 g (39%) of a red product.

$^1$H NMR (300 MHz, CD$_2$Cl, 25° C.): δ [ppm]=9.53 (s, 1H); 9.50 (s, 1H); 8.89 (sb, 2H); 8.66 (dd, J=7.2 Hz, 2H); 5.20-5.12 (m, 2H); 2.25-2.20 (m, 4H); 1.86-1.80 (m, 4H); 1.28-1.22 (m, 40H); 0.85-0.81 (m, 12H).

$^{13}$C NMR (75 MHz, CD$_2$Cl, 25° C.): δ [ppm]=162.55 (C=O); 138.21; 137.13; 132.86; 132.66; 131.52; 130.10; 129.28; 128.48; 127.18; 120.61; 54.75; 41.08; 31.77; 29.44; 29.18; 26.85; 22.59; 13.79.

IR (KBr): ν (cm$^{-1}$)=2956, 2925, 2854, 1703, 1660, 1589, 1381, 1329, 1240, 810, 748

UV-Vis (CHCl3): $\lambda_{max}$ ($\epsilon$)=390 (6000); 460 (15000); 490 (37000); 526 nm (55000 M$^{-1}$ cm$^{-1}$)

MS (FD): 971.3 (100%) [M$^+$] (calculated for C$_{54}$H$_{68}$Br$_2$N$_2$O$_4$ 968.96)

3.2 N,N'-bis(1-heptyloctyl)-1,7-didocen-1-yneperylene-3, 4:9,10-tetracarboximide 0.2 g (0.206 mmol) of N,N'-bis(1-heptyloctyl)-1,7-dibromoperylene-3,4:9,10-tetracarboximide from Example 3.1, 0.14 g (0.824 mmol) of 10 dodec-1-yne, 25 mg (0.021 mmol), 6 mg (0.020 mmol) of [Pd(PPh$_3$)$_2$Cl], triphenylphosphine and copper(I) iodide (4 mg, 0.020 mmol) were stirred at 80° C. in a mixture of 20 ml of triethylamine and 20 ml of tetrahydrofuran for 16 h. After cooling to room temperature, the solution was poured into dilute HCl (100 ml) and the mixture was extracted with CH$_2$Cl. The solvent was evaporated under reduced pressure and the resulting solid was purified by column chromatography on silica gel (3/1 pentane/CH$_2$Cl), which afforded a red product (0.15 g, 64%). The product comprises small amounts of N,N'-di(1-heptyloctyl)-5,11-didecylcoronene-2,3:8,9-tetracarboximide, which were removable by very careful column chromatography on silica gel (3/1 pentane/CH$_2$Cl).

$^1$H NMR (300 MHz, C$_2$D$_2$Cl$_4$, 100° C.): δ [ppm]=10.13 (d, J=8.2 Hz, 2H); 8.72 (s, 2H); 8.60 (d, J=8.2 Hz, 2H); 5.12 (sept, J=6.1 Hz, 2H); 2.63 (t, J=7.1 Hz, 4H); 2.22-2.17 (m, 4H); 1.89-1.74 (m, 8H); 1.58-1.53 (m, 4H); 1.26-1.22 (m, 64H); 0.84-0.79 (m, 18H).

$^{13}$C NMR (75 MHz, C$_2$D$_2$Cl$_4$, 100° C., Spinecho experiment): δ [ppm]=164.11 (C=O); 138.34 (t); 134.44 (q); 134.00 (q); 130.49 (t); 127.97 (q); 127.85 (q); 127.18 (t); 123.66 (q); 122.71 (q); 121.28 (q); 102.06 (q); 82.82 (q); 55.18 (CH); 32.77 (CH$_2$); 32.03 (CH$_2$); 31.96 (CH$_2$); 29.73 (CH$_2$); 29.67 (CH$_2$); 29.43 (CH$_2$); 29.40 (CH$_2$); 29.33 (CH$_2$); 29.29 (CH$_2$); 28.61 (CH$_2$); 27.19 (CH$_2$); 22.76 (CH$_2$); 22.70 (CH$_2$); 20.52 (CH$_2$); 14.12 (CH$_3$); 14.09 (CH$_3$).

IR (KBr): ν (cm$^{-1}$)=2958, 2925, 2856, 2214, 1699, 1657, 1601, 1589, 1466, 1410, 1342, 1327, 1259, 1246, 812, 756, 706

UV-Vis (CHCl$_3$): $\lambda_{max}$ ($\epsilon$)=413 (7000); 477 (13000); 512 (28000); 553 nm (48000 M$^{-1}$ cm$^{-1}$)

MS (FD): 1139.7 (100%) [M$^+$] (calculated for C$_{78}$H$_{110}$N$_2$O$_4$ 1139.76)

3.3 N,N'-di(1-heptyloctyl)-5,11-didecylcoronene-2,3:8,9-tetracarboximide 0.1 g (0.088 mmol) of N,N'-di(1-heptyloctyl)-1,7-di(dodec-1-ynyl)perylene-3,4:9,10-tetracarboximide from Example 3.2 were dissolved in 30 ml of toluene and the oxygen was removed from the solution with argon. Thereafter, 0.1 ml of 1,8-diazabicyclo[5.4.0]undec-7-ene (DBU) was added and the mixture was stirred at 110° C. for 20 h. After cooling to room temperature, the solution was poured into cold dilute HCl (300 ml) and the mixture was extracted with toluene. The solvent was evaporated under reduced pressure and the solid obtained was purified by column chromatography on silica gel (3/1 petroleum ether/CH$_2$Cl), which afforded a yellow product (40 mg, 40%) having a melting point of 285° C.

$^1$H NMR (300 MHz, C$_2$D$_2$Cl$_4$, 100° C.): δ [ppm]=10.14 (s, 2H); 9.88 (s, 2H); 8.96 (s, 2H); 5.40 (sept, J=5.9 Hz, 2H); 3.89 (t, J=7.7 Hz, 4H); 2.47-2.36 (m, 4H); 2.23-2.18 (m, 4H); 2.09-2.02 (m, 4H); 1.71-1.66 (m, 4H); 1.48-1.21 (m, 64H); 0.87-0.76 (m, 18H).

$^{13}$C NMR (75 MHz, C$_2$D$_2$Cl$_4$, 100° C., Spinecho experiment): δ [ppm]=142.09 (C=O); 130.46 (t); 130.20 (q); 129.64 (q); 128.58 (t); 127.16 (q); 126.75 (t); 124.36 (q); 123.16 (q); 123.03 (q); 122.58 (q); 122.35 (q); 121.71 (q); 55.59 (CH); 34.06 (CH$_2$); 33.09 (CH$_2$); 32.04 (CH$_2$); 31.97 (CH$_2$); 31.70 (CH$_2$); 30.02 (CH$_2$); 29.77 (CH$_2$); 29.43 (CH$_2$); 29.34 (CH$_2$); 27.41 (CH$_2$); 22.76 (CH$_2$); 22.69 (CH$_2$); 14.13 (CH$_3$); 14.07 (CH$_3$).

IR (KBr): ν (cm$^{-1}$)=2960, 2927, 2856, 1703, 1660, 1606, 1469, 1335, 926, 810.

UV-Vis (CHCl$_3$): $\lambda_{max}$ ($\epsilon$)=334 (70000); 337 (70000); 382 (8000); 404 (28000); 429 (58000); 477 (10000); 511 nm (18000 M$^{-1}$ cm$^{-1}$).

Fluorescence (CHCl$_3$): $\lambda_{max}$=515, 555, 601 nm.

MS (FD): 1139.8 (100%) [M$^+$] (calculated for C$_{78}$H$_{110}$N$_2$O$_4$ 1139.76).

Example 4

N,N'-di(1-heptyloctyl)perylene-3,4:9,10-tetracarboximide (1)

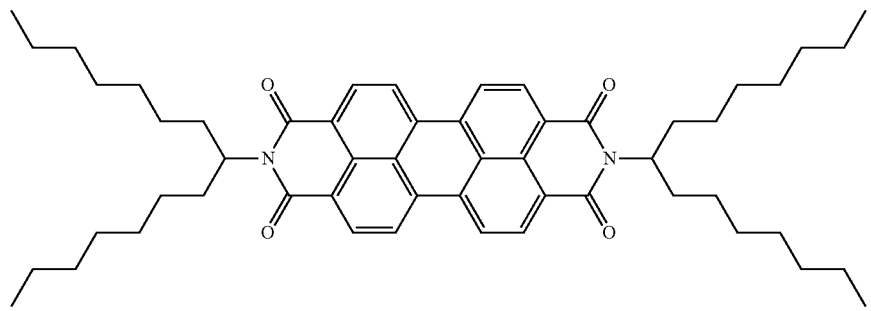 [SMILES: CCCCCCCC(CCCCCCC)N1C(=O)c2ccc3c4ccc5c6c(ccc(c7ccc(c2c37)C1=O)c64)C(=O)N(C(CCCCCCC)CCCCCCC)C5=O]

This compound was prepared according to H. Langhals, S. Demmig, T. Potrawa, J. prakt. Chem. 1991, 333, 733-748.

Example 5

N,N'-di(1-heptyloctyl)terrylene-3,4:11,12-tetracarboximide by one-stage base-induced dimerization To a mixture, heated to 60° C., of 7 ml of diethylene glycol diethyl ether, 2.79 g (29 mmol) of sodium tert-butoxide and 13.7 g (90 mmol) of 1,8-diazabicyclo[5.4.0]undec-7-ene (DBU) were added 0.77 g (1.45 mmol) of N-1-heptyloctylperylene-3,4-dicarboximide and 2.36 (5.8 mmol) of N-1-heptyloctylnapthalene-1,8-dicarboximide. The reaction mixture is heated to 130° C. for 6 hours and then cooled to room temperature, diluted with ethyl acetate and washed repeatedly with dilute hydrochloric acid. After the ethyl acetate phase has been dried over magnesium sulfate, the ethyl acetate is removed under reduced pressure. The residue is chromatographed with a gradient of toluene and petroleum ether. 0.13 g (10%) of a blue solid is obtained. The formation of a quaterrylene diimide is not observed.

Example 6

1,6,9,14-tetrabromo-N,N'-di(1-heptyloctyl)terrylene-3,4:11,12-tetracarboximide

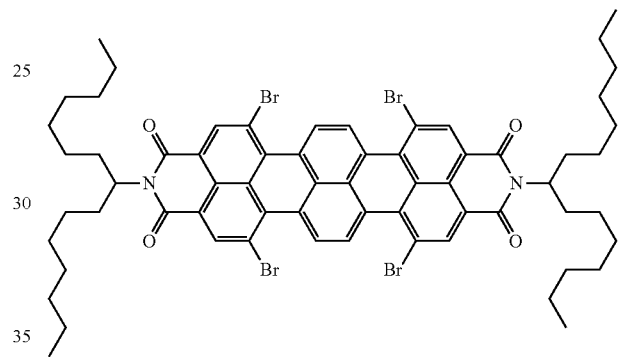

A mixture of 15 ml of chlorobenzene, 5 ml of water, 0.13 g (0.13 mmol) of the above-described compound are admixed with a few drops of bromine and a spatula-tip of iodine, and heated to 90° C. for 7 hours. Subsequently, the reaction mixture is cooled and dichloromethane is added, a sodium sulfite solution is added and the phases are separated. After the organic phases have been dried, the solvent is removed under reduced pressure and the remaining residue is purified by column chromatography purification with a toluene/petroleum ether gradient. 90 mg (52%) of a blue solid are obtained.

$R_f$(toluene)=0.71

Example 7

N,N'-di(1-heptyloctyl)quaterrylene-3,4:13,14-tetracarboximide

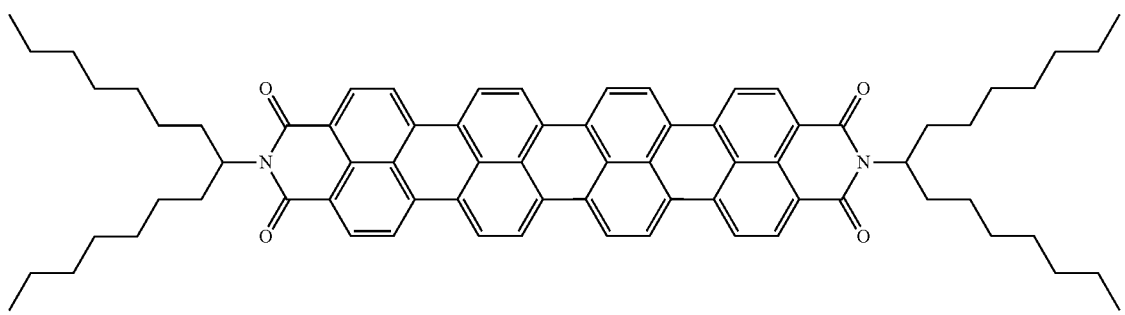 [SMILES: CCCCCCCC(CCCCCCC)N1C(=O)c2ccc3c4ccc5c6ccc7c8ccc9c%10c(ccc(c%11ccc(c%12ccc(c%13ccc(c2c3%13)C1=O)c4c5%12)c6c7%11)c%108)C(=O)N(C(CCCCCCC)CCCCCCC)C9=O]

A mixture of 1.48 g (13 mmol) of potassium tert-butoxide, 2.3 g (15.1 mmol) of DBU, 2.2 g (36.3 mmol) of ethanolamine and 1.0 g (1.9 mmol) of N-(1-heptyloctyl)perylene-3,4-dicarboximide is heated to 170° C. for 6 hours. Subsequently, the reaction mixture is admixed with dilute hydrochloric acid and with dichloromethane, the phases are separated, the aqueous phase is extracted repeatedly with dichloromethane and dried, and the solvent is removed under reduced pressure. 1.8 g of a green oily crude product are obtained, which is purified further by chromatography with dichloromethane. 0.15 g (15%) of the green product is obtained.

Example 8

N,N'-(1-heptyloctyl)-1,6-dibromoperylene-3,4;9,19-tetracarboximide and N,N'-(1-heptyloctyl)-1,7-dibromoperylene-3,4;9,19-tetracarboximide (approx. 15:85)

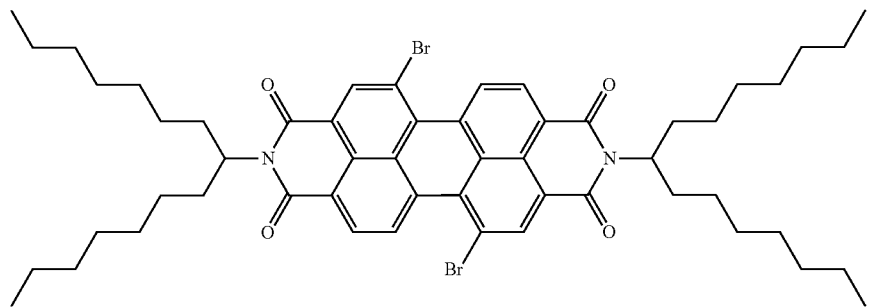

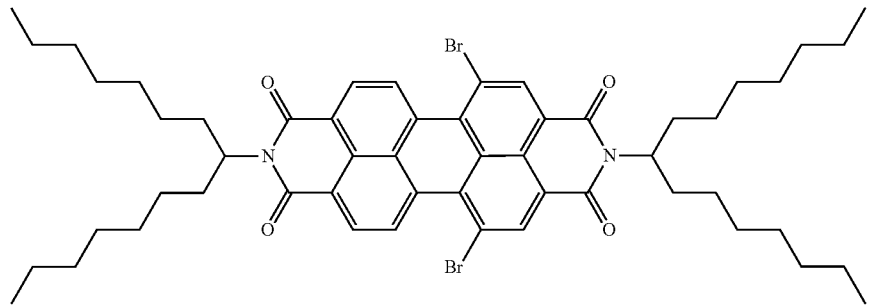

A mixture of 16 ml of quinoline, 2 ml of propionic acid, 1.10 g (2 mmol) of dibromoperylene-3,4:9,10-tetracarboximide and 1.82 g (8 mmol) of 1-heptyloctylamine is heated to 90° C. for 3 hours. The reaction mixture is cooled to room temperature and diluted with 250 ml of dilute hydrochloric acid. After a saturated sodium chloride solution has been added, the product precipitates out and is filtered off and washed with water and dried. The product is purified by chromatography.

$R_f$(toluene)=0.66 (1,6-isomer), 0.74 (1,7-isomer)

Example 9

N,N'-(1-heptyloctyl)-1,6-dibromoperylene-3,4;9,19-tetracarboximide and N,N'-(1-heptyloctyl)-1,7-dibromoperylene-3,4;9,19-tetracarboximide (15:85)

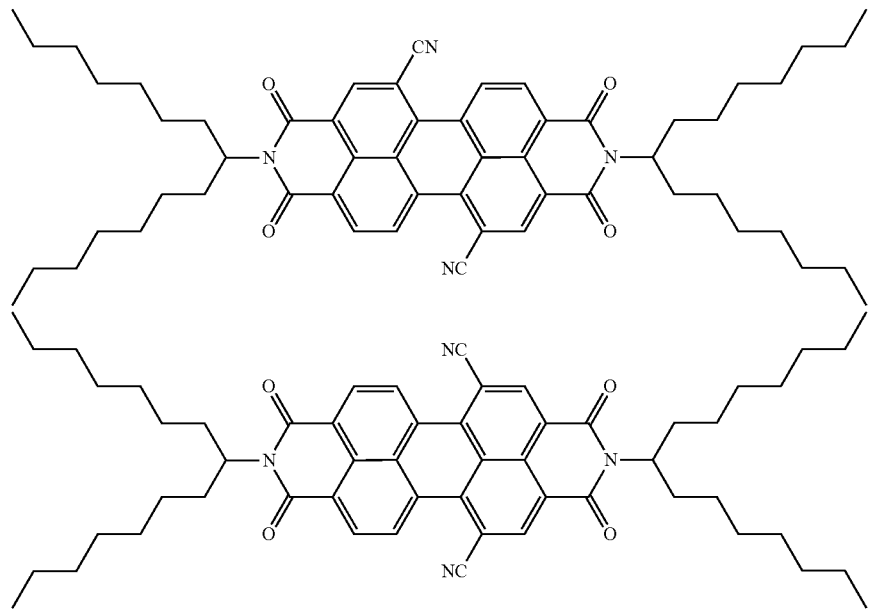

A mixture of 20 ml of toluene, 1.17 g (10 mmol) of zinc cyanide, 242 mg (0.25 mmol) of the dibromoperylene compound from Example 8, 69 mg (0.125 mmol) of 1,1'-bis(diphenylphosphinoferrocene) and 114 mg (0.125 mmol) of tris(dibenzylideneacetone)dipalladium is heated to 100° C. for 6.5 hours. The reaction mixture is allowed to cool to room temperature, and the residue is filtered off, washed with toluene and dried under reduced pressure. The residue is subjected to a first column chromatography with a petroleum ether-toluene gradient and to a second column chromatography with a petroleum ether-THF gradient.

$R_f$ (petroleum ether: THF=10:1)=0.51

Example 10

N,N'-bis(3,4,5-tridodecylphenyl)-1,6-difluoroperyl-3,4;9,10-tetracarboximide and N,N'-bis(3,4,5-tridodecylphenyl)-1,7-difluoroperyl-3,4;9,10-tetracarboximide (approx. 13:87)

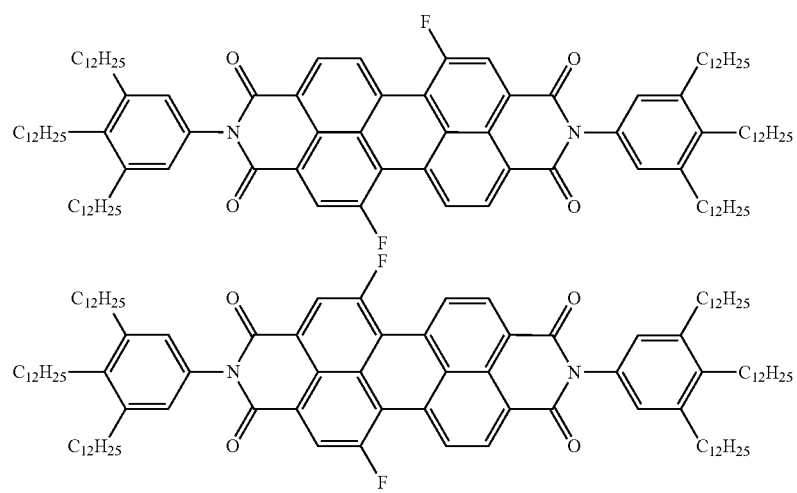

A mixture of 100 mg (233 mmol) of 1,7-difluoroperylene-3,4:9,10 tetracarboxylic bisanhydride which comprises approx. 25% 1,6 difluoro isomer, 550 mg of tridodecylaniline, 51 mg of zinc acetate and 13 ml of quinoline is heated to 180° C. for four hours. After cooling to room temperature, the reaction mixture is poured onto 100 ml of 1 molar hydrochloric acid, and the precipitate is filtered and washed with water and then with methanol. The residue is purified by column chromatography (1:1 petroleum ether/dichloromethane and 3:2 petroleum ether/dichloromethane). 45 mg (12%) of an orange solid are obtained, which, according to $^1$H NMR, comprises 13% of the 1,6-isomer.

Figure 6:
FIG. 6 shows the texture under the polarization microscope of the sample of Example 10.
Figure 7:
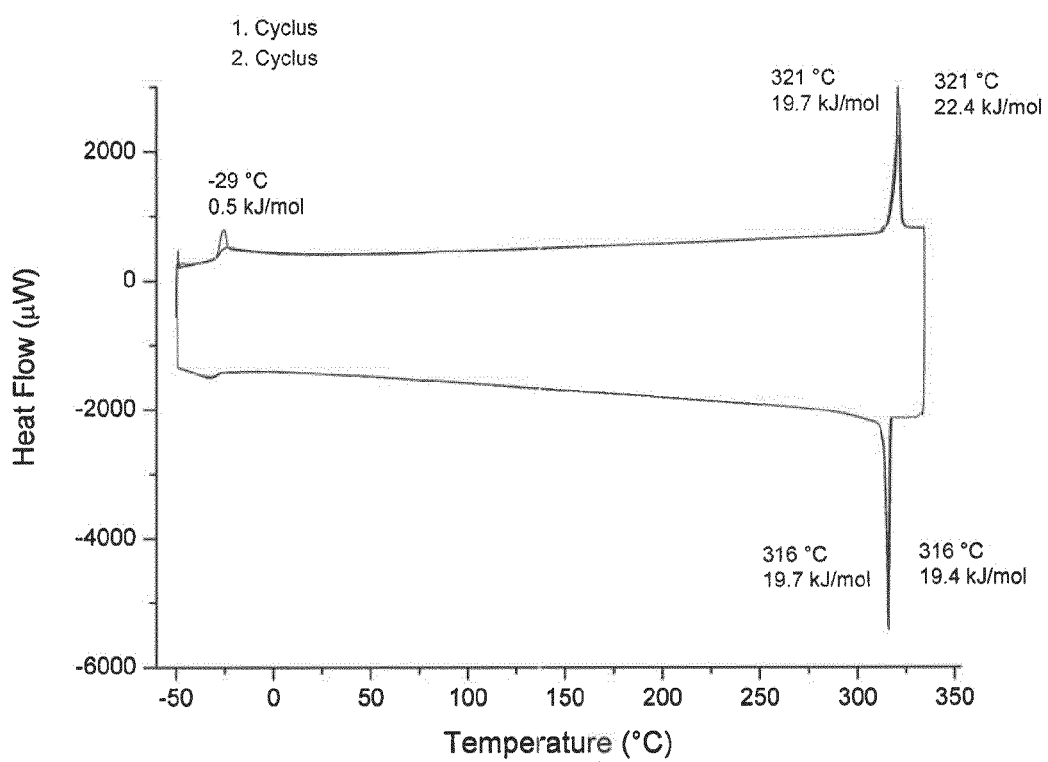
FIG. 7 shows the DSC (differential scanning calorimetry) of the sample of Example 10.

As a sample of the compound was heated above the clearing temperature of 320° C. and subsequently cooled, in a polarization microscope under cross polarizers, the formation of a texture typical of hexagonal columnar mesophases was observed. FIGS. 6 and 7 show the textures under the polarization microscope, and the DSC (differential scanning calorimetry) of the sample. Columnar phases are crucial for the achievement of a high mobility of the charge carriers in organic field-effect transistors and in organic solar cells.

Example 11

N,N'-bis(3,4,5-tridodecylphenyl)quaterrylene-3,4;13,14-tetracarboximide

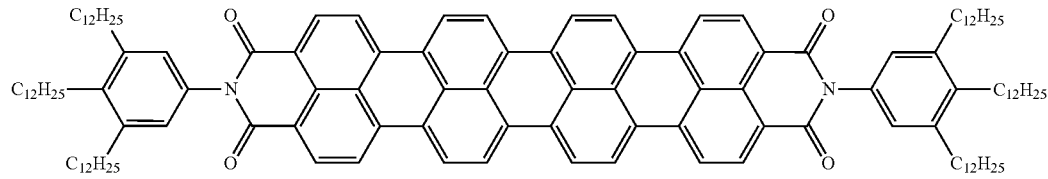

Example 11.1

N-(3,4,5-tridodecylphenyl)-9-bromoperylene-3,4-dicarboximide

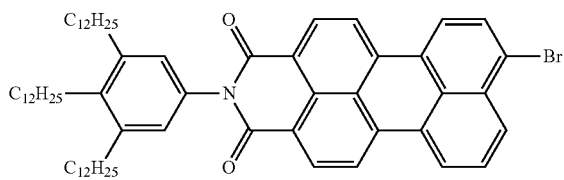

9-bromoperylene-3,4-dicarboxylic monoanhydride is prepared according to WO2004/029028. A mixture of 10 ml of quinoline, 0.53 g (0.83 mmol) of 3,4,5-tridodecylaniline, 0.66 g (3 mmol) of zinc acetate dehydrate and 0.401 g (1 mmol) of 9-bromoperylene-3,4-dicarboxylic monoanhydride is heated to 180° C. for 2 hours. After cooling to room temperature, dilute hydrochloric acid is added, and the product of value is extracted with dichloromethane. The product is purified by chromatography in 1:1 toluene/petroleum ether. 0.71 g (72%) of an orange solid is obtained.

$R_f$(toluene)=0.55

Example 11.2

N-(3,4,5-tridodecylphenyl)-9-(4,4,5,5-tetramethyl-1,3,2-dioxaborolan-2-yl)perylene-3,4-dicarboximide

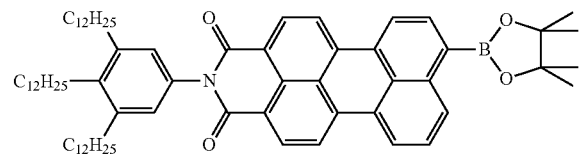

0.276 g (0.281 mmol) of the 9-bromo compound from Example 13.1, 15 ml of toluene, 89.2 mg (0.351 mmol) of bispinacolatodiborane, 30.3 mg (0.31 mmol) of potassium acetate and 11.4 mg (0.014 mmol) of (1,1-bis(diphenylphosphino)ferrocene)-dichloropalladium are heated to reflux for 21 hours. Subsequently, a further 892 mg (3.51 mmol) of bispinacolatodiborane, 61 mg of potassium acetate, 23 mg (0.028 mmol) of (1,1-bis(diphenylphosphino)ferrocene) dichloropalladium and 15 ml of xylene are added thereto. The mixture is heated to 130° C. for a further 28 hours and then cooled to room temperature. The solvent mixture is removed under reduced pressure and the residue is purified by chromatography with petroleum ether and toluene. 0.28 g (quantitative) of a dark red solid is obtained.

$R_f$(toluene)=0.20

Example 11.3

N,N'-bis(3,4,5-tridodecylphenyl)-9,9'-biperylene-3,4:3',4'-bis(dicarboximide)

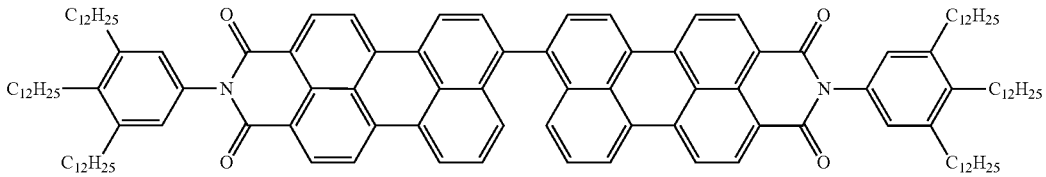

A mixture of 280 mg (0.27 mmol) of the perylene-boron compound from Example 13.2, 184 mg (0.187 mmol) of the 9-bromoperylene compound from Example 13.1, 15 ml of toluene, 5 ml of ethanol, 11 mg (0.01 mmol) of tetrakistriphenylphosphinepalladium and 10 ml (10 mmol) of a 1 M sodium carbonate solution is heated to 80° C. for 16 hours. After cooling to room temperature, the phases are separated, the aqueous phase is extracted repeatedly with toluene and dried, and the solvent of the combined organic phases is removed under reduced pressure. After chromatography with toluene, 230 mg (47%) of the product can be isolated as a violet-black solid.

$R_f$(toluene)=0.24

Example 11.4

N,N'-bis(3,4,5-tridodecylphenyl)quaterrylene-3,4;13,14-tetracarboximide

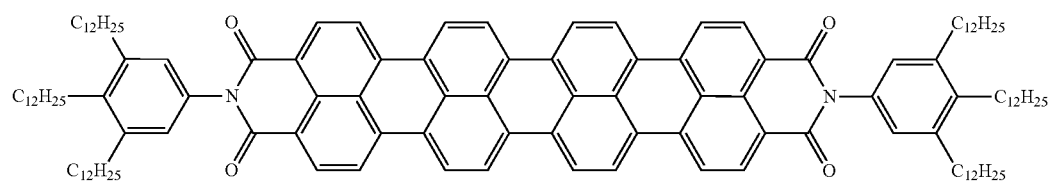

A mixture of 230 mg (0.128 mmol) of the bisperylene compound from Example 13.3, 0.85 g (6.1 mmol) of potassium arbonate, 2 ml of ethanolamine and 15 ml of mesitylene is heated to 160° C. for 2.5 hours. After cooling to room temperature, the solvent is removed under reduced pressure and the residue is purified by chromatography with 50:1 dichloromethane/ethyl acetate. 110 mg (48%) of a green solid are obtained. Further purification can be achieved by chromatography with THF.

$R_f$(CH$_2$Cl$_2$:ethyl acetate=50:1)=0.4

$\lambda_{max}$ (THF)=701 nm (78 l/g cm), 748 nm (44 l/g cm)

Example 12

Production of an Excitonic Solar Cell

The following semiconductor materials were used:

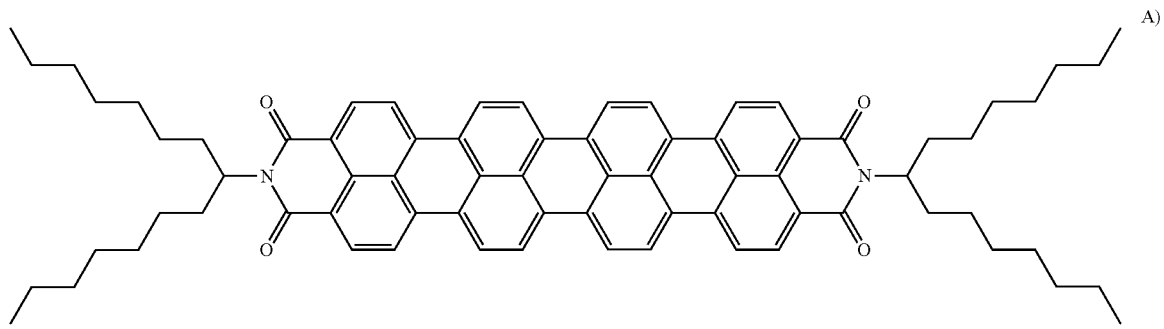

A)

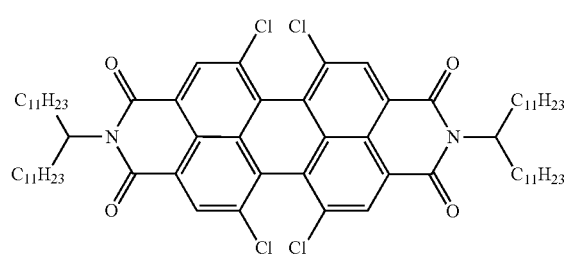

B)

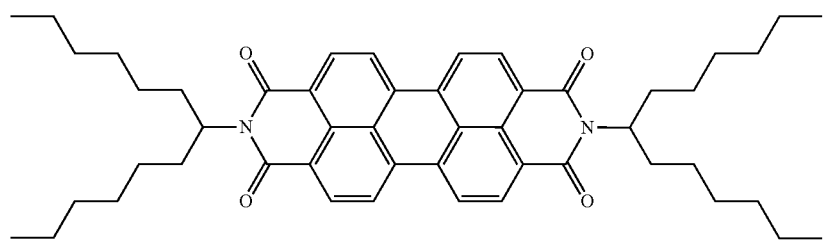

C)

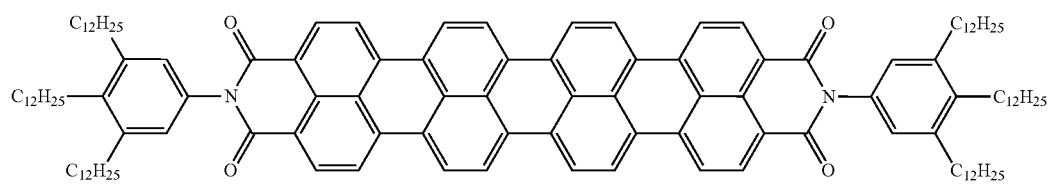

D)

Construction:

The working electrodes used were glass plates coated with indium-doped tin oxide (ITO) of dimensions 25 mm×15 mm×1.2 mm (resistance from 30 to 60 ohms, Sigma-Aldrich). These were cleaned successively with the glass cleaner, water and acetone in an ultrasound bath, after treated in boiling isopropanol and dried in a nitrogen stream. Subsequently, the substrates were coated with a PEDOT layer (=poly(3,4-ethylenedioxythiophene) of thickness about 100 nm by spin-coating. PEDOT was used in aqueous solution (Baytron®P VP AI 4083), the spin-coating frequency was 4500 rpm and the spinning time was 30 s. Thereafter, the sample was dried at 100° C. in a drying cabinet for 15 minutes.

To electrically insulate the metal back electrodes from the working electrode, a strip of polyimide (Pyrrolin Polyimide Coating, Supelco) was applied to each longitudinal edge of the PEDOT layer and hardened at 200° C. in a drying cabinet for 15 minutes.

The active organic layers were applied in the following sequence. First, as the donor, copper phthalocyanine (CuPc, sublimed in a simple gradient) was applied by vapor deposition, then, as the acceptor, the compound A) was applied by means of spin-coating, and finally, as the buffer layer, bathocuproine (BCP) was applied to the PEDOT/polyimide layer by a thermal evaporation under reduced pressure. A pressure of $2\times10^{-6}$ mbar was employed. The evaporation of the CuPc took place at a temperature of 360° C. and a vapor deposition rate of from 0.2 to 1.0 nm/s. The layer thicknesses formed were from 35 to 40 nm for the CuPc, approx. 40 nm for the layer of the compound C) applied by means of spin-coating, and 20 nm for the BCP layer.

The metal back electrode was applied by thermal metal evaporation under reduced pressure. To this end, the sample was provided with a mask, in order to apply eight separate round back electrodes with a diameter of 1 mm to the active region, each of which are connected to a contact area of about 3 mm×2 mm in size through the polyimide layer. The metal used was Ag, which was evaporated at a rate of from 0.5 to 1.5 nm/s at a pressure of approx. $4\times10^{-5}$ mbar, so as to give rise to a layer thickness of 100 nm.

Figure 8:
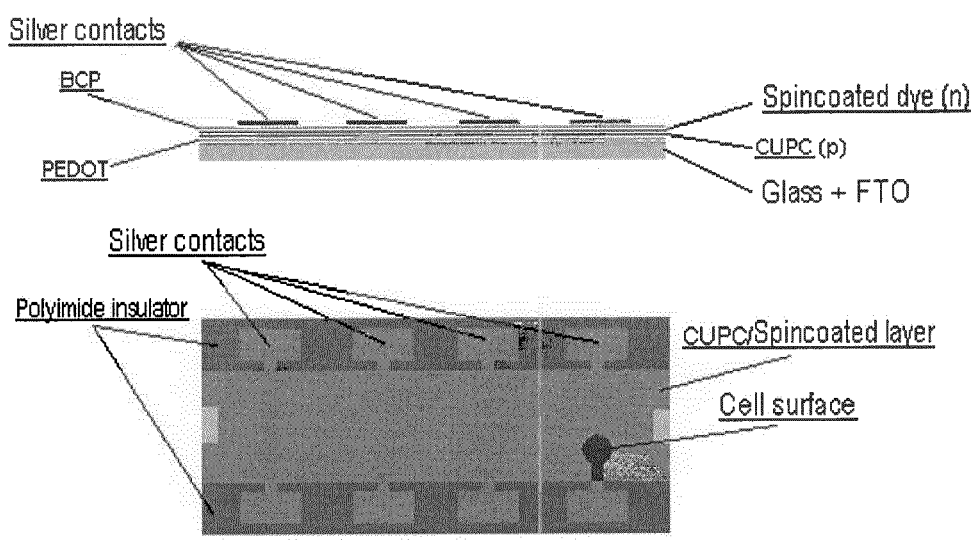
FIG. 8 shows a structure of the solar cell of Example 11.4.

The structure of the solar cell is reproduced in FIG. 8.

Solar cells of compounds B) to D) were produced analogously.

To determine the efficiency η, the particular current/voltage characteristic was measured with a Source Meter Model 2400 (Keithley Instruments Inc.) while irradiating with a halogen lamp field (Xenophot® 64629; Osram) as a sun simulator.

Figure 9:
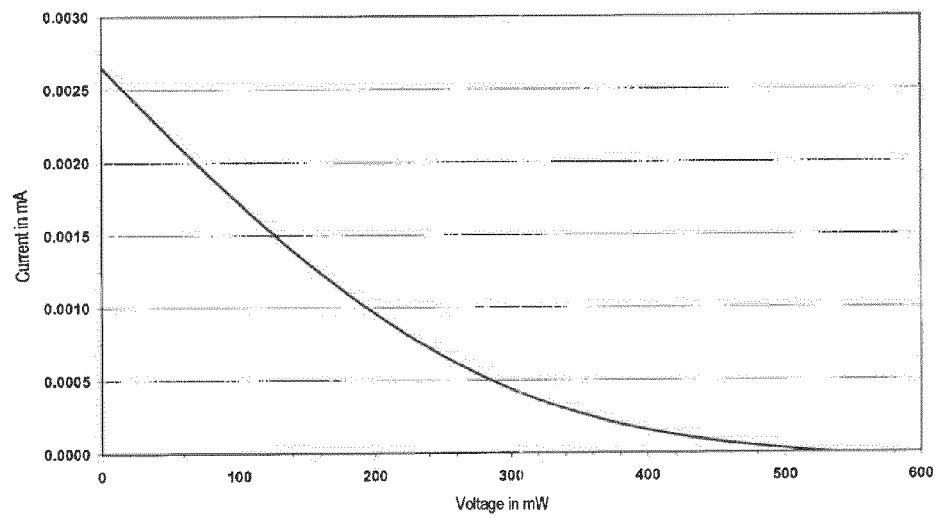
FIG. 9 shows the current-voltage characteristic of compound B).

FIG. 9 shows the current-voltage characteristic of compound B).

Figure 10:
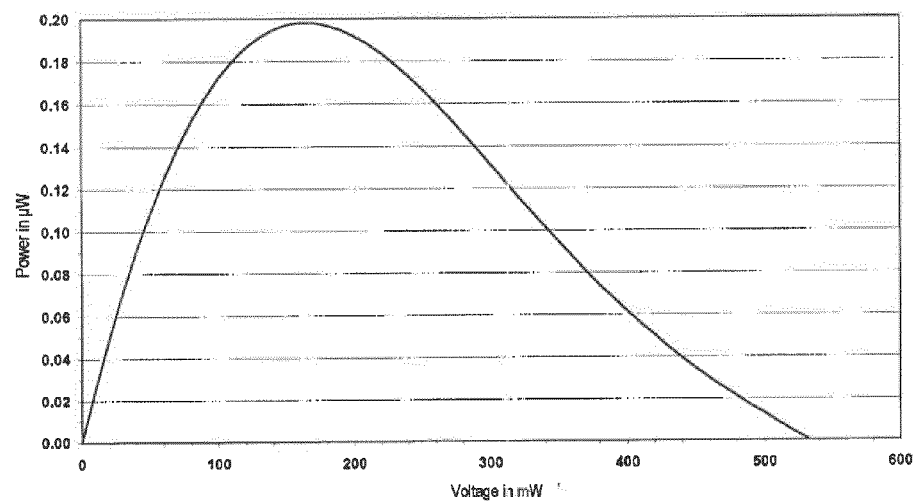
FIG. 10 shows the power-voltage characteristic of compound B).

FIG. 10 shows the power-voltage characteristic of compound B).

Figure 11:
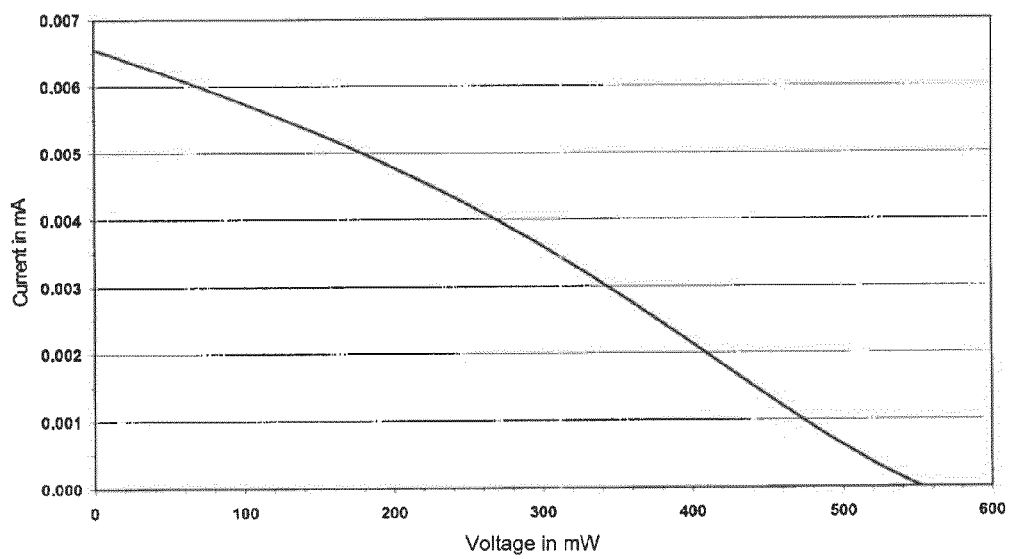
FIG. 11 shows the current-voltage characteristic of compound C).

FIG. 11 shows the current-voltage characteristic of compound C).

Figure 12:
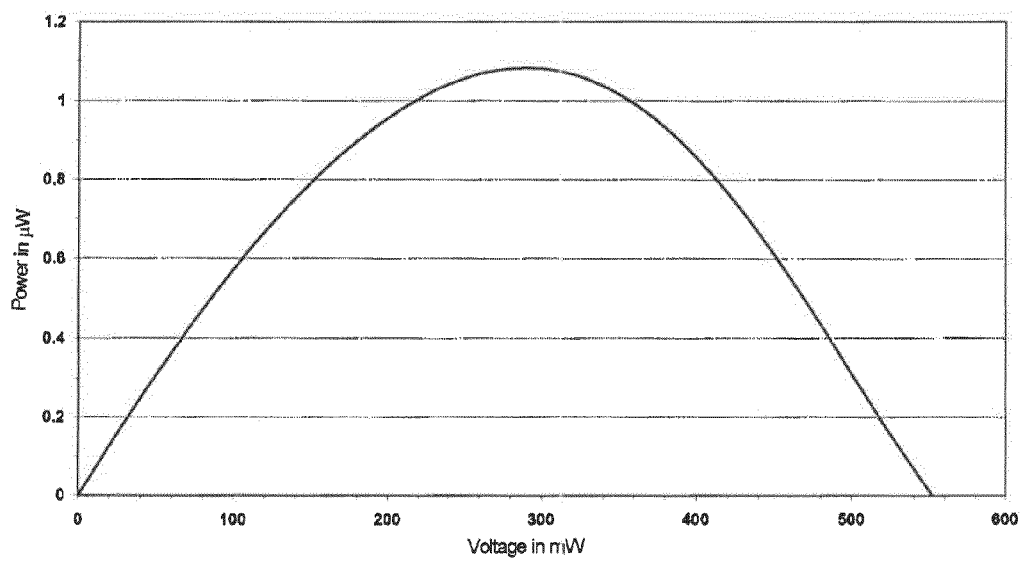
FIG. 12 shows the power-voltage characteristic of compound C).

FIG. 12 shows the power-voltage characteristic of compound C).

The following electrical data were obtained:

| Example | p/n type | % sun | $U_{OC}$ mV | $I_{SC}$ mA/cm2 | FF | Eta % |
|---------|----------|-------|-------------|-----------------|------|-------|
| 13.1    | CuPc/A)  | 100   |             |                 |      | 0.021 |
| 13.2    | CuPc/B)  | 100   | 126         | 0.72            | 26.2 | 0.024 |
| 13.3    | CuPc/C)  | 100   | 552         | 0.819           | 30.0 | 0.135 |
| 13.4    | CuPc/D)  | 100   |             |                 |      | 0.028 |

$U_{OC}$ = open terminal voltage
$I_{SC}$ = short-circuit current
FF = fill factor
Eta = efficiency

Example 13

General Method for Determining Transistor Characteristics

Production of semiconductor substrates by means of drop-casting

The substrates used were n-doped silicon wafers (2.5×2.5 cm, conductivity <0.004 $\Omega^{-1}$ cm) with a thermally deposited oxide layer (300 nm) as a dielectric (capacitance based on area $C_i$=10 nF/cm$^2$). To produce source and drain electrodes of channel length 5 mm and channel width 10 μm, photolithography and gas phase deposition were used to deposit a 60 nm gold layer onto 4 nm of chromium. The surfaces of the substrates were modified by treatment with hexamethyldisilazane (HMDS) at 120° C. for 2 hours. The semiconductor compounds were vapor deposited on the substrate by evaporation of a toluene solution (10 mg/ml). The electrical properties of the OFETs were determined by means of a Keithley 4200-SCS semiconductor parameter analyzer under a dry nitrogen atmosphere.

Figure 13:
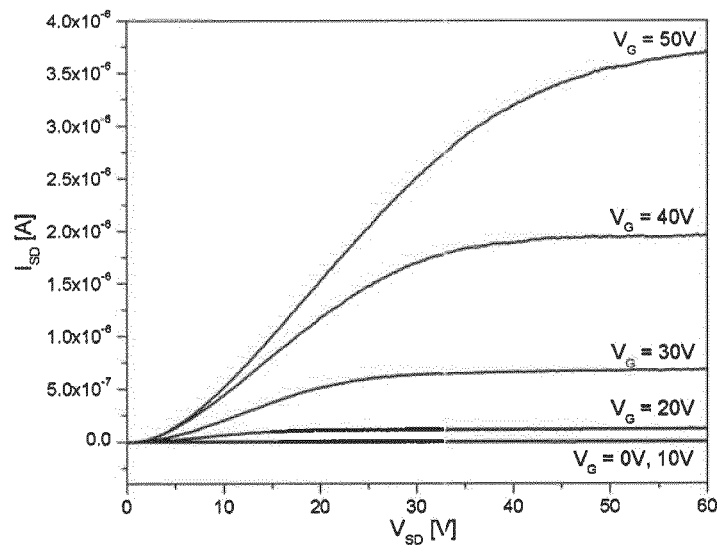
FIG. 13 shows the current-voltage characteristics of the compound in Example 13.

FIG. 13 shows the current-voltage characteristics of

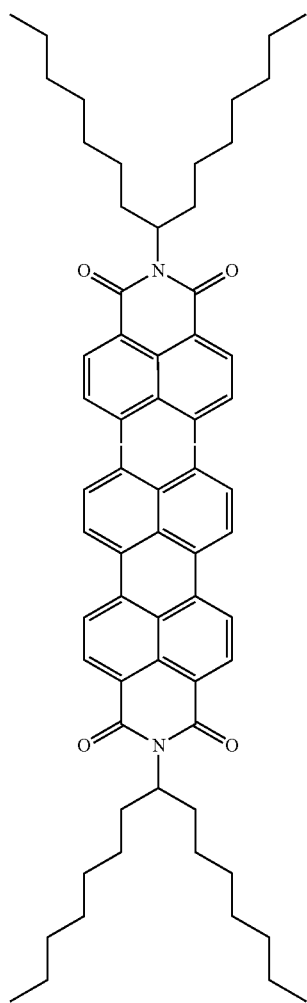 [SMILES: CCCCCCCC(CCCCCCC)N1C(=O)c2ccc3c4ccc5c6ccc7c8c(ccc(c9ccc(c%10ccc(c2c3%10)C1=O)c4c59)c86)C(=O)N(C(CCCCCCC)CCCCCCC)C7=O]

Figure 14:
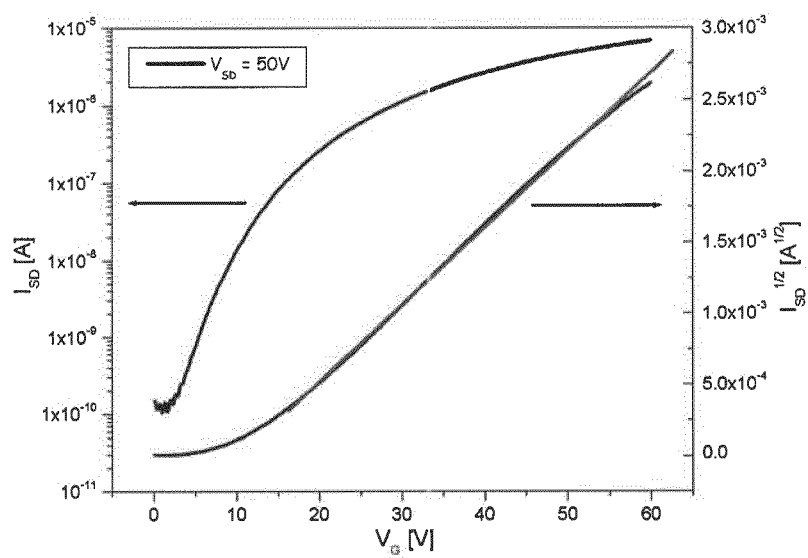
FIG. 14 shows the transfer characteristics of the corresponding field-effect transistor of Example 13.

FIG. 14 shows the transfer characteristics of the corresponding field-effect transistor.

The invention claimed is:

1. A n-semiconductor for organic field-effect transistors or solar cells comprising compounds of the general formula (I):

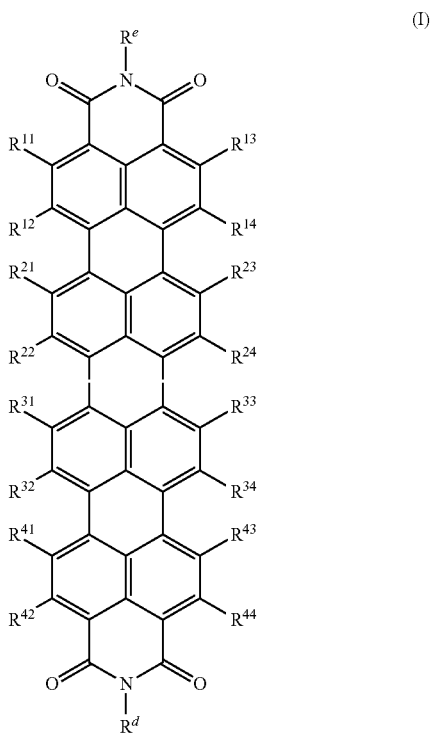

(I)

wherein
the $R^{11}$, $R^{12}$, $R^{13}$, $R^{14}$, $R^{21}$, $R^{22}$, $R^{23}$, $R^{24}$, $R^{31}$, $R^{32}$, $R^{33}$, $R^{34}$, $R^{41}$, $R^{42}$, $R^{43}$, and $R^{44}$ radicals are each independently selected from hydrogen, F, Cl, and Br;
the $R^c$ and $R^d$ radicals are each independently selected from groups of the formulae (II.1) to (II.5):

(II.1)

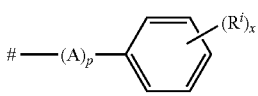

(II.2)

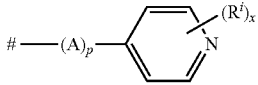

(II.3)

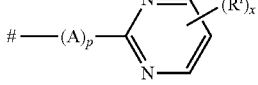

(II.4)

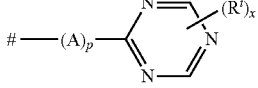

(II.5)

in which
represents the bonding site to the imide nitrogen atom,
p is 0 or 1,
x is 2 or 3, A where present, is a $C_1$-$C_{10}$-alkylene group which may be interrupted by one or more nonadjacent groups which are selected from —O— and —S—, where, in the case that x in the compounds of the formula (II.1) is 2, the carbon atom which bears the $R^i$ radicals additionally bears a hydrogen atom, and where x in the compounds of the formula (II.5) is 2, and the $R^i$ radicals are each independently selected from $C_4$-$C_{30}$-alkyl which may be interrupted by one or more nonadjacent oxygen atom(s), where at least one of the $R^i$ radicals in the compounds of the formula (II.1) may also be $C_4$-$C_{30}$-alkyloxy or $C_4$-$C_{30}$-alkylthio.

2. The n-semiconductor according to claim 1, wherein the $R^i$ radicals are each independently selected from linear $C_4$-$C_{30}$-alkyl which may be interrupted by one or more nonadjacent oxygen atom(s).

3. The n-semiconductor according to claim 1, wherein the $R^{11}, R^{12}, R^{13}, R^{14}, R^{21}, R^{22}, R^{23}, R^{24}, R^{31}, R^{32}, R^{33}, R^{34}, R^{41}, R^{42}, R^{43}$, and $R^{44}$ radicals in the compounds of the formula (I) are all hydrogen.

in which

\# represents the bonding site to the imide nitrogen atom, and the $R^i$ radicals are selected from $C_4$-$C_8$-alkyl.

7. The n-semiconductor according to claim 1 comprising at least one compound of the formula (I) where the $R^c$ and $R^d$ radicals are each independently selected from groups of the formulae (II.2) to (II.5).

8. The n-semiconductor according to claim 7 comprising at least one compound of the formula (I) where the $R^c$ and $R^d$ radicals are each independently selected from groups of the formula (II.2) and x in the groups of the formula (II.2) is 3.

9. The n-semiconductor according to claim 1 at least one compound which is selected from:

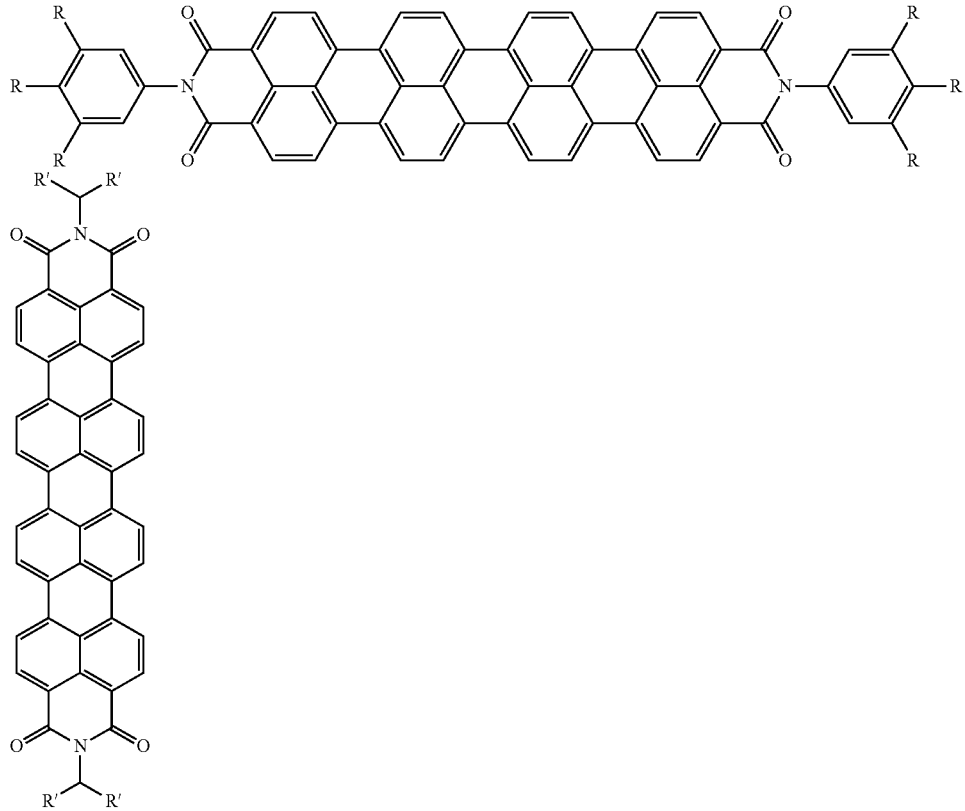

4. The n-semiconductor according to claim 1, wherein at least one of the $R^{11}, R^{12}, R^{13}, R^{14}, R^{21}, R^{22}, R^{23}, R^{24}, R^{31}, R^{32}, R^{33}, R^{34}, R^{41}, R^{42}, R^{43}$, and $R^{44}$ radicals in the compounds of the formula (I) is a radical other than hydrogen.

5. The n-semiconductor according to claim 1, wherein the $R^i$ radicals are selected from $C_4$-$C_{18}$-alkyl.

6. The n-semiconductor according to claim 1 comprising compounds of the formula (I) where the $R^c$ and $R^d$ groups are each groups of the formula (II.1)

in which R and R' are each $C_4$-$C_{18}$-alkyl.

10. The n-semiconductor for organic field-effect transistors comprising compounds of the general formula (I) as defined in claim 1.

11. The n-semiconductor for excitonic solar cells comprising compounds of the general formula (I) as defined in claim 1.

12. A process for preparing compounds of the formula (I)

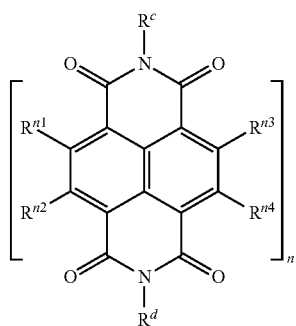
(I)

wherein n is 4, and the $R^c$ and $R^d$ radicals are each independently selected from groups of the formulae (II.1) to (II.5):

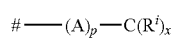
(II.1)

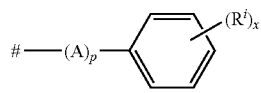
(II.2)

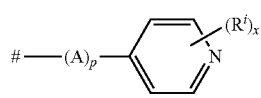
(II.3)

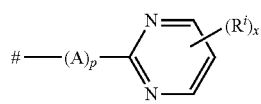
(II.4)

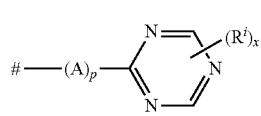
(II.5)

in which

\# represents the bonding site to the imide nitrogen atom, p is 0 or 1, x is 2 or 3, A where present, is a $C_1$-$C_{10}$-alkylene group which may be interrupted by one or more nonadjacent groups which are selected from —O— and —S—, where, in the case that x in the compounds of the formula (II.1) is 2, the carbon atom which bears the $R^i$ radicals additionally bears a hydrogen atom, and where x in the compounds of the formula (II.5) is 2, and the $R^i$ radicals are each independently selected from $C_4$-$C_{30}$-alkyl which may be interrupted by one or more nonadjacent oxygen atom(s), in which α) a compound of the formula (IIIa)

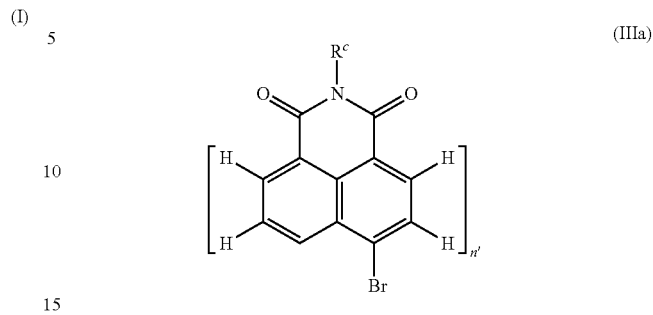
(IIIa)

where
n' is 2
is reacted with a diborane of the formula (IV)

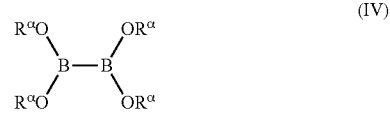
(IV)

in which $R^\alpha$ are the same or different and are each independently hydrogen, $C_1$-$C_{30}$-alkyl, $C_5$-$C_8$-cycloalkyl, aryl or hetaryl, where the $R^\alpha$ radicals may also be bonded to one another to form a five-membered ring which comprises the two oxygen atoms and the boron atom and may be substituted on the carbon atoms by up to 4 $C_1$-$C_{30}$-alkyl, $C_5$-$C_8$-cycloalkyl, aryl or hetaryl groups, to obtain a compound of the formula (V)

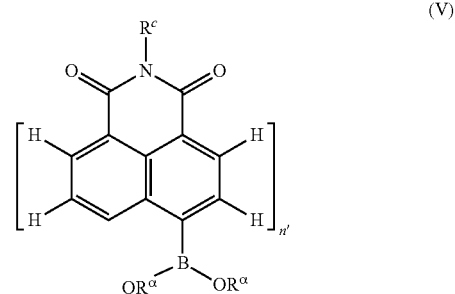
(V)

β) the compound of the formula (V) is subjected to a Suzuki coupling reaction with a compound of the formula (IIIb)

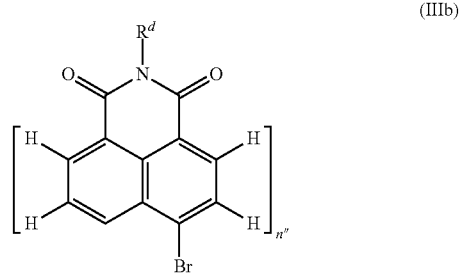
(IIIb)

where
n" is 2,
in the presence of a transition metal catalyst and of a base to obtain a compound of the formula (VI)

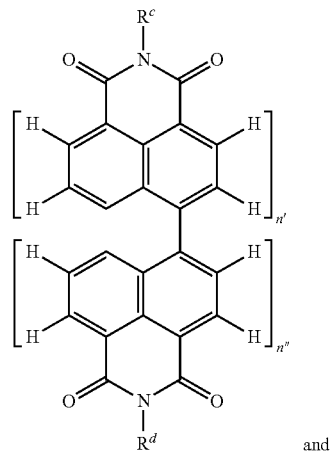

(VI)

γ) the compound of the formula (VI) is converted by cyclodehydrogenation in an organic reaction medium which has hydroxyl and amino functions and comprises an essentially undissolved base to a compound of the formula (I) where n represents the sum of n' and n".

13. A process for preparing compounds of the formula (I)

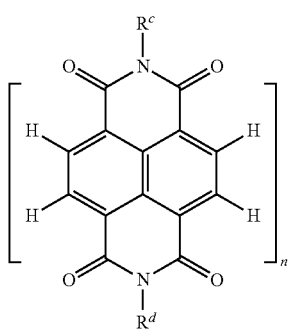

(I)

wherein
n is 4, and
the $R^c$ and $R^d$ radicals are each independently selected from groups of the formulae (II.1) to (II.5):

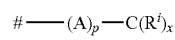

(II.1)

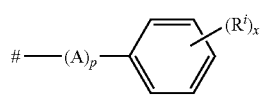

(II.2)

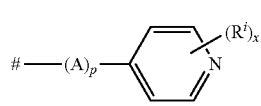

(II.3)

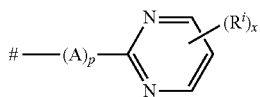

(II.4)

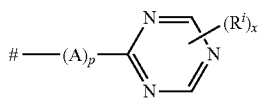

(II.5)

in which
represents the bonding site to the imide nitrogen atom,
p is 0 or 1,
x is 2 or 3,
A where present, is a $C_1$-$C_{10}$-alkylene group which may be interrupted by one or more nonadjacent groups which are selected from —O— and —S—,
where, in the case that x in the compounds of the formula (II.1) is 2, the carbon atom which bears the $R^i$ radicals additionally bears a hydrogen atom, and
where x in the compounds of the formula (II.5) is 2, and
the $R^i$ radicals are each independently selected from $C_4$-$C_{30}$-alkyl which may be interrupted by one or more nonadjacent oxygen atom(s),
in which a perylene-3,4-dicarboximide of the general formula (VII)

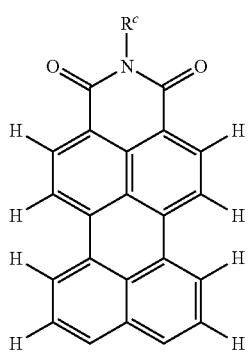

(VII)

in the presence of a base-stable solvent and of an alkali metal base or alkaline earth metal base, is reacted with a compound of the general formula (VIII)

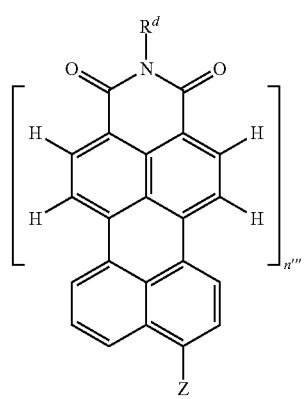

(VIII)

where n'" is 1 and Z is hydrogen, bromine or chlorine.

14. A compound of the general formula (I)

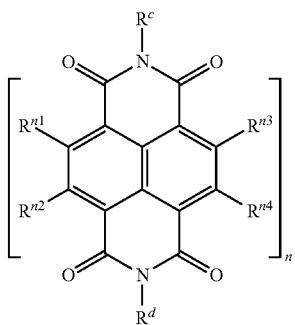

wherein
n is 4,
the $R^{n1}$, $R^{n2}$, $R^{n3}$ and $R^{n4}$ radicals are each independently selected from hydrogen, F, Cl and Br, and
the $R^c$ and $R^d$ radicals are each independently selected from groups of the formulae (II.1) to (II.5):

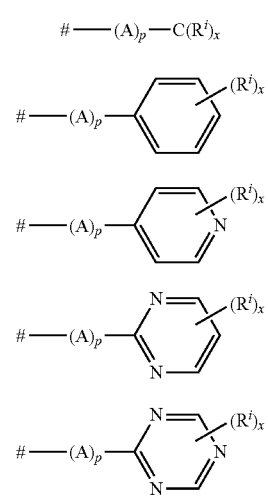

in which
represents the bonding site to the imide nitrogen atom,
p is 0 or 1,
x is 2 or 3,
A where present, is a $C_1$-$C_{10}$-alkylene group which may be interrupted by one or more nonadjacent groups which are selected from —O— and —S—,
where, in the case that x in the compounds of the formula (II.1) is 2, the carbon atom which bears the $R^i$ radicals additionally bears a hydrogen atom, and
where x in the compounds of the formula (II.5) is 2, and the $R^i$ radicals are each independently selected from $C_4$-$C_{30}$-alkyl which may be interrupted by one or more nonadjacent oxygen atom(s), where at least one of the $R^i$ radicals in the compounds of the formula (II.1) may also be $C_4$-$C_{30}$-alkyloxy or $C_4$-$C_{30}$-alkylthio, excluding:
compounds of the formula (I) in which n is 4, the $R^{n1}$, $R^{n2}$, $R^{n3}$ and $R^{n4}$ radicals are all hydrogen, and the $R^c$ and $R^d$ radicals are each a radical of the formula (II.1) or (II.2);
wherein the compound has n-semiconductor properties.

15. A compound according to claim 14 where at least one of the $R^{n1}$, $R^{n2}$, $R^{n3}$ and $R^{n4}$ radicals is a radical other than hydrogen.

16. A compound of the formula

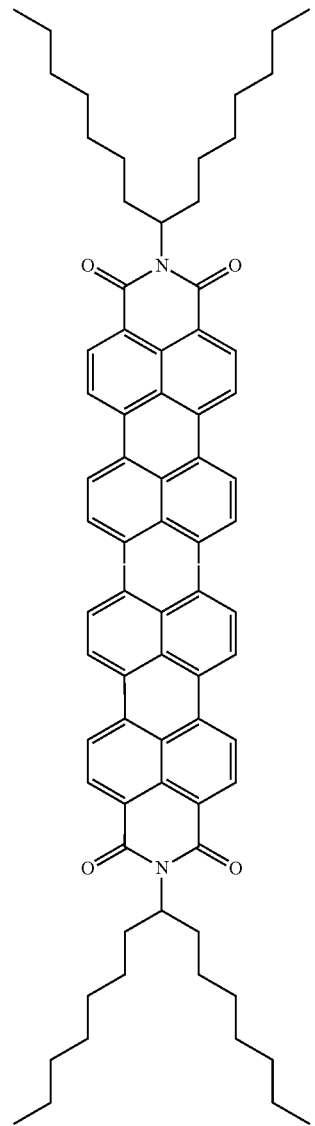 [SMILES: CCCCCCCC(CCCCCCC)N1C(=O)c2ccc3c4ccc5c6ccc7c8ccc9c%10c(ccc(c%11ccc(c%12ccc(c%13ccc(c2c3%13)C1=O)c4c5%12)c6c7%11)c%108)C(=O)N(C(CCCCCCC)CCCCCCC)C9=O]

wherein the compound has n-semiconductor properties.

17. An organic field-effect transistor comprising a substrate having at least one gate structure, a source electrode and a drain electrode, and at least one compound of the formula I as defined in claim 14 or claim 16 as an n-semiconductor.

18. A substrate comprising a multitude of organic field-effect transistors, wherein at least some of the field-effect transistors comprise at least one compound of the formula I as defined in claim 14 or claim 16 as an n-semiconductor.

19. A semiconductor unit comprising at least one substrate as defined in claim 18.

20. A method of using at least one compound of the general formula (I) as defined in claim 14 or claim 16 in organic field-effect transistors.

21. A method of using at least one compound of the general formula (I) as defined in claim 14 or claim 16 for optical labels, for invisible marking of products, as fluorescent dyes, as a fluorescent label for biomolecules and as pigments.

22. A method of using at least one compound of the general formula (I) as defined in claim 14 or claim 16 as a fluorescent dye in a display based on fluorescence conversion; in a light-collecting plastics part which may be combined with a solar cell; as a pigment dye in electrophoretic displays; and as a fluorescent dye in an application based on chemoluminescence.

* * * * *